United States Patent
Gnanasambandam et al.

(10) Patent No.: US 12,159,113 B2
(45) Date of Patent: Dec. 3, 2024

(54) SYSTEM AND METHOD FOR DIAGNOSING DISEASE THROUGH COGNIFICATION OF UNSTRUCTURED DATA

(71) Applicant: HEALTHPOINTE SOLUTIONS, INC., Austin, TX (US)

(72) Inventors: Nathan Gnanasambandam, Irvine, CA (US); Mark Henry Anderson, Newport Coast, CA (US)

(73) Assignee: Healthpointe Solutions, Inc., Austin, TX (US)

( * ) Notice: Subject to any disclaimer, the term of this patent is extended or adjusted under 35 U.S.C. 154(b) by 82 days.

(21) Appl. No.: 17/638,148

(22) PCT Filed: Aug. 21, 2020

(86) PCT No.: PCT/US2020/047482
§ 371 (c)(1),
(2) Date: Feb. 24, 2022

(87) PCT Pub. No.: WO2021/041243
PCT Pub. Date: Mar. 4, 2021

(65) Prior Publication Data
US 2022/0300713 A1    Sep. 22, 2022

Related U.S. Application Data

(63) Continuation of application No. 16/593,491, filed on Oct. 4, 2019, now Pat. No. 11,263,405.
(Continued)

(51) Int. Cl.
*G06F 17/00* (2019.01)
*G06F 40/295* (2020.01)
(Continued)

(52) U.S. Cl.
CPC ............ *G06F 40/30* (2020.01); *G06F 40/295* (2020.01); *G06N 5/04* (2013.01); *G16H 10/20* (2018.01); *G16H 50/20* (2018.01); *G16H 70/00* (2018.01)

(58) Field of Classification Search
None
See application file for complete search history.

(56) References Cited

U.S. PATENT DOCUMENTS 5,839,438 A * 11/1998 Graettinger .............. A61B 5/00
600/300
8,271,415 B2 * 9/2012 Iliff ........................ G16H 10/60
706/46
(Continued)

FOREIGN PATENT DOCUMENTS

JP    2001273362 A    10/2001

OTHER PUBLICATIONS

International Searching Authority, Search Report and Written Opinion for International Application No. PCT/US19/55615, mailed on Jan. 8, 2020; 10 pages.
(Continued)

*Primary Examiner* — Satwant K Singh
(74) *Attorney, Agent, or Firm* — Dickinson Wright PLLC

(57) ABSTRACT

A method for diagnosing a medical condition through cognification of unstructured data is disclosed. The method may include receiving, at a server, an electronic medical record including notes pertaining to a patient. The method may also include generating cognified data using the notes, where the cognified data includes a health summary of the medical condition. The method may also include generating, based on the cognified data, a diagnosis of the medical condition of the patient, where the diagnosis at least identifies a type of the medical condition. The method may also include
(Continued)

providing the diagnosis to a computing device for presentation on the computing device.

18 Claims, 37 Drawing Sheets

Related U.S. Application Data

(60) Provisional application No. 62/891,661, filed on Aug. 26, 2019.

(51) Int. Cl.
*G06F 40/30* (2020.01)
*G06N 5/04* (2023.01)
*G16H 10/20* (2018.01)
*G16H 50/20* (2018.01)
*G16H 70/00* (2018.01)

(56) References Cited

U.S. PATENT DOCUMENTS

| | | | |
|---|---|---|---|
| 8,337,409 B2* | 12/2012 | Iliff | G16H 50/70 128/923 |
| 8,579,812 B2 | 11/2013 | Causevic | |
| 8,666,926 B1 | 3/2014 | Nease et al. | |
| 9,536,052 B2* | 1/2017 | Amarasingham | G16H 50/30 |
| 10,431,337 B2 | 10/2019 | Allen et al. | |
| 10,431,338 B2 | 10/2019 | Allen et al. | |
| 10,541,053 B2 | 1/2020 | Sheffer et al. | |
| 11,263,405 B2* | 3/2022 | Gnanasambandam | G16H 10/20 |
| 2009/0083231 A1 | 3/2009 | Eberholst et al. | |
| 2010/0278420 A1 | 11/2010 | Shet et al. | |
| 2012/0029361 A1 | 2/2012 | Addison et al. | |
| 2012/0047105 A1 | 2/2012 | Saigal et al. | |
| 2012/0129139 A1 | 3/2012 | Partovi | |
| 2012/0158633 A1 | 6/2012 | Eder | |
| 2012/0239560 A1 | 9/2012 | Pourfallah et al. | |
| 2014/0074454 A1 | 3/2014 | Brown et al. | |
| 2014/0188511 A1* | 7/2014 | Gaylis | G16H 20/00 705/2 |
| 2015/0019248 A1 | 1/2015 | Anand et al. | |
| 2015/0193583 A1 | 7/2015 | McNair et al. | |
| 2015/0332283 A1 | 11/2015 | Witchey | |
| 2016/0171119 A1 | 6/2016 | Bufe et al. | |
| 2016/0321406 A1 | 11/2016 | Timmerman et al. | |
| 2016/0364534 A1 | 12/2016 | Naji | |
| 2017/0076053 A1 | 3/2017 | Sysko et al. | |
| 2017/0091397 A1 | 3/2017 | Shah | |
| 2017/0091423 A1* | 3/2017 | Kumar | G16H 20/60 |
| 2017/0132393 A1 | 5/2017 | Natarajan et al. | |
| 2017/0235906 A1* | 8/2017 | Dorris | G16H 20/70 705/2 |
| 2017/0277841 A1* | 9/2017 | Shankar | G16Z 99/00 |
| 2017/0286618 A1* | 10/2017 | Abelseth | G16H 40/67 |
| 2018/0025127 A1 | 1/2018 | Bagchi et al. | |
| 2018/0032514 A1 | 2/2018 | Venkataraman et al. | |
| 2018/0089383 A1 | 3/2018 | Allen et al. | |
| 2018/0285879 A1 | 10/2018 | Gadnis et al. | |
| 2018/0336317 A1 | 11/2018 | Carbonell et al. | |
| 2019/0171958 A1* | 6/2019 | Sudharsan | G06N 7/01 |
| 2019/0252074 A1* | 8/2019 | Datla | G06F 17/10 |
| 2019/0392547 A1 | 12/2019 | Katouzian et al. | |
| 2021/0241906 A1* | 8/2021 | Zhang | G16H 80/00 |
| 2022/0171944 A1* | 6/2022 | Gnanasambandam | G06F 40/295 |

OTHER PUBLICATIONS

International Searching Authority, Search Report and Written Opinion for International Application No. PCT/US19/55614, mailed on Jan. 8, 2020; 10 pages.

International Searching Authority, Search Report and Written Opinion for International Application No. PCT/US19/55617, mailed on Jan. 8, 2020; 10 pages.

International Searching Authority, Search Report and Written Opinion for International Application No. PCT/US19/55619, mailed on Jan. 8, 2020; 15 pages.

International Searching Authority, Search Report and Written Opinion for International Application No. PCT/US20/33284, mailed on Jul. 29, 2020; nine pages.

International Searching Authority, Search Report and Written Opinion for International Application No. PCT/US20/33634, mailed on Aug. 6, 2020; nine pages.

International Searching Authority, Search Report and Written Opinion for International Application No. PCT/US20/47477, mailed on Nov. 20, 2020; nine pages.

International Searching Authority, Search Report and Written Opinion for International Application No. PCT/US20/47480, mailed on Nov. 23, 2020; nine pages.

International Searching Authority, Search Report and Written Opinion for International Application No. PCT/US20/47482, mailed on Nov. 23, 2020; 10 pages.

* cited by examiner

FIG. 12

SYSTEM AND METHOD FOR DIAGNOSING DISEASE THROUGH COGNIFICATION OF UNSTRUCTURED DATA

CROSS-REFERENCE TO RELATED APPLICATIONS

This application claims the benefit of U.S. patent application Ser. No. 16/593,491 filed Oct. 4, 2019 titled "System and Method for Answering Natural Language Questions Posed by a User," which claims the benefit of U.S. Provisional Application Ser. No. 62/743,985 filed Oct. 10, 2018 titled "Population Management for Health," and U.S. Provisional Application Ser. No. 62/801,777 filed Feb. 6, 2019 titled "System and Method for Answering Natural Language Questions Posed by a User." This application also claims the benefit of U.S. Provisional Application Ser. No. 62/891,661 filed Aug. 26, 2019 titled "System and Method for Diagnosing Disease Through Cognification of Unstructured Data." All applications are incorporated by reference herein as if reproduced in full below.

BACKGROUND

Population health management entails aggregating patient data across multiple health information technology resources, analyzing the data with reference to a single patient, and generating actionable items through which care providers can improve both clinical and financial outcomes. A population health management service seeks to improve the health outcomes of a group by improving clinical outcomes while lowering costs.

SUMMARY

Representative embodiments set forth herein disclose various techniques for enabling a system and method for diagnosing disease through cognification of unstructured data.

In some embodiments, a method for diagnosing a medical condition through cognification of unstructured data is disclosed. The method may include receiving, at a server, an electronic medical record including notes pertaining to a patient. The method may also include generating cognified data using the notes, where the cognified data includes a health summary of the medical condition. The method may also include generating, based on the cognified data, a diagnosis of the medical condition of the patient, where the diagnosis at least identifies a type of the medical condition. The method may also include providing the diagnosis to a computing device for presentation on the computing device.

In some embodiments, a system includes a memory storing instructions and a processor communicatively coupled with the memory. The processor may execute the instructions to perform one or more of the operations of the method described above.

In some embodiments, a tangible, non-transitory computer-readable medium stores instructions. A process may execute the instructions to perform one or more of the operations of the method described above.

BRIEF DESCRIPTION OF THE DRAWINGS

For a detailed description of example embodiments, reference will now be made to the accompanying drawings in which:

FIG. 12 shows aspects of a feed, in accordance with various embodiments.

NOTATION AND NOMENCLATURE

Figure 1:
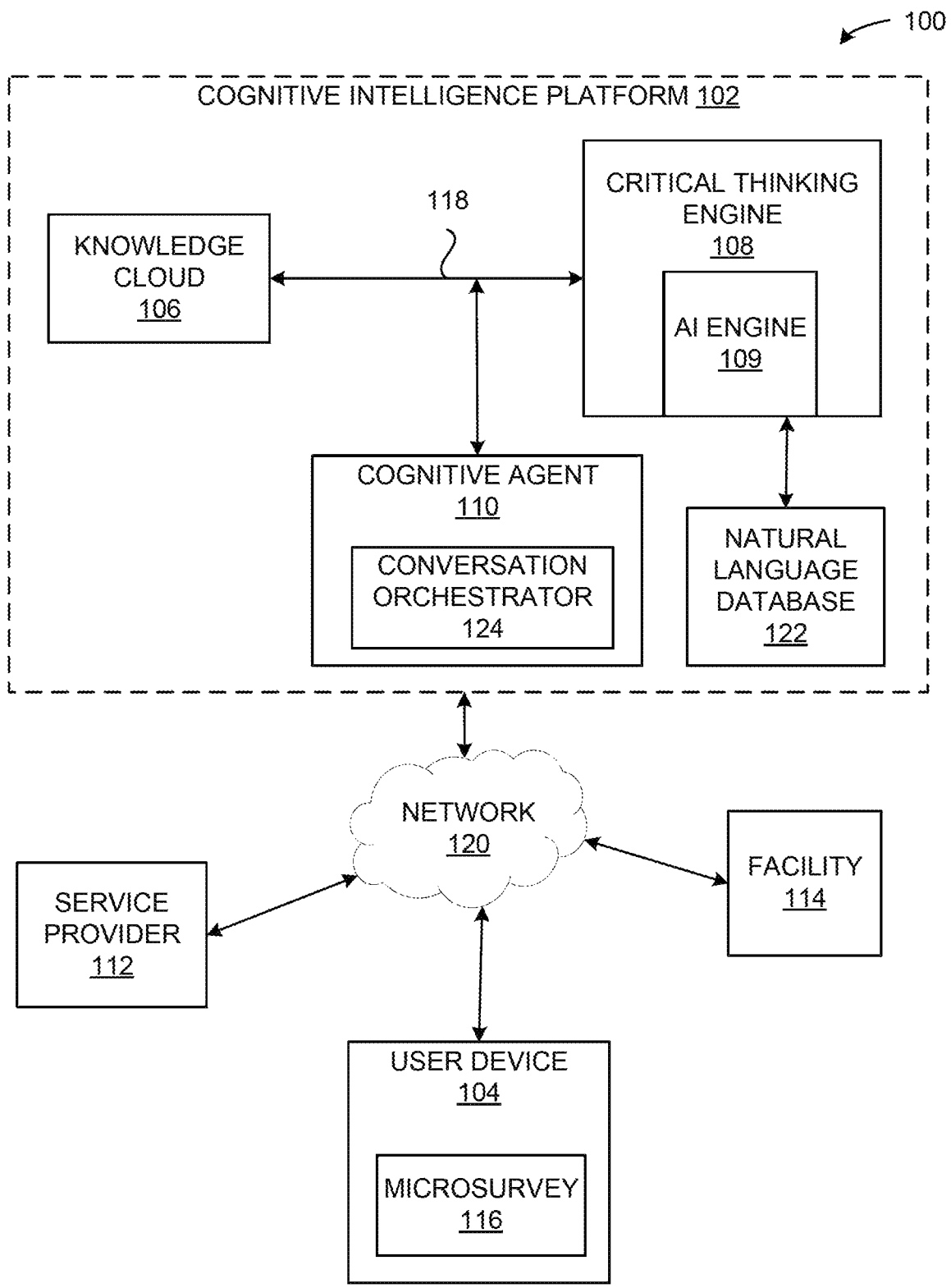
FIG. 1 illustrates, in block diagram form, a system architecture 100 that can be configured to provide a population health management service, in accordance with various embodiments.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . " Also, the term "couple" or "couples" is intended to mean either an indirect or direct connection. Thus, if a first device couples to a second device, that connection may be through a direct connection or through an indirect connection via other devices and connections.

DETAILED DESCRIPTION

The following discussion is directed to various embodiments of the invention. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

According to some embodiments, a cognitive intelligence platform integrates and consolidates data from various sources and entities and provides a population health management service. The cognitive intelligence platform has the ability to extract concepts, relationships, and draw conclusions from a given text posed in natural language (e.g., a passage, a sentence, a phrase, and a question) by performing conversational analysis which includes analyzing conversational context. For example, the cognitive intelligence platform has the ability to identify the relevance of a posed question to another question.

The benefits provided by the cognitive intelligence platform, in the context of healthcare, include freeing up physicians from focusing on day to day population health management. Thus a physician can focus on her core competency—which includes disease/risk diagnosis and prognosis and patient care. The cognitive intelligence platform provides the functionality of a health coach and includes a physician's directions in accordance with the medical community's recommended care protocols and also builds a systemic knowledge base for health management.

Accordingly, the cognitive intelligence platform implements an intuitive conversational cognitive agent that engages in a question and answering system that is human-like in tone and response. The described cognitive intelligence platform endeavors to compassionately solve goals, questions and challenges.

In addition, physicians often generate patient notes before, during, and/or after consultation with a patient. The patient notes may be included in an electronic medical record (EMR). When a patient returns for a subsequent visit, the physician may review numerous EMRs for the patient. Such a review process may be time consuming and inefficient. Insights may be hidden in the various EMRs and may result in the physician making an incorrect diagnosis. Further, it may involve the physician accessing numerous screens and performing multiple queries on a database to obtain the various EMRs. As a result, the computing device of the physician may waste computing resources by loading various screens and sending requests for EMR data to a server. The server that receives the requests may also waste computing resources by processing the numerous requests and transmitting numerous responses. In addition, network resources may be wasted by transmitting the requests and responses between the server and the client.

Accordingly, some embodiments of the present disclosure address the issues of reviewing the EMRs, by cognifying unstructured data. Unstructured data may include patient notes entered into one or more EMRs by a physician. The patient notes may explain symptoms described by the patient or detected by the physician, vital signs, recommended treatment, risks, prior health conditions, familial health history, and the like. The patient notes may include numerous strings of characters arranged into sentences. The sentences may be organized in one or more paragraphs. The sentences may be parsed and indicia may be identified. The indicia may include predicates, objectives, nouns, verbs, cardinals, ranges, keywords, phrases, numbers, concepts, or some combination thereof.

The indicia may be compared to one or more knowledge graphs that each represents health related information (e.g., a disease) and various characteristics of the health related information. The knowledge graph may also include how the various diseases are related to one another (e.g., bronchitis can lead to pneumonia). The knowledge graph may represent a model that includes individual elements (nodes) and predicates that describe properties and/or relationships between those individual elements. A logical structure (e.g., Nth order logic) may underlie the knowledge graph that uses the predicates to connect various individual elements. The knowledge graph and the logical structure may combine to form a language that recites facts, concepts, correlations, conclusions, propositions, and the like. The knowledge graph and the logical structure may be generated and updated continuously or on a periodic basis by an artificial intelligence engine with evidence-based guidelines, physician research, patient notes in EMRs, physician feedback, and so forth. The predicates and individual elements may be generated based on data that is input to the artificial intelligence engine. The data may include evidence-based guidelines that is obtained from a trusted source, such as a physician. The artificial intelligence engine may continuously learn based on input data (e.g., evidence-based guidelines, clinical trials, physician research, electronic medical records, etc.) and modify the individual elements and predicates.

For example, a physician may indicate that if a person has a blood sugar level of a certain amount and various other symptoms (e.g., unexplained weight loss, sweating, etc.), then that person has type 2 diabetes mellitus. Such a conclusion may be modeled in the knowledge graph and the logical structure as "Type 2 diabetes mellitus has symptoms of a blood sugar level of the certain amount and various other symptoms," where "Type 2 diabetes mellitus," "a blood sugar level of the certain amount," and "various other symptoms" are individual elements in the knowledge graph, and "has symptoms of" is a predicate of the logical structure that relates the individual element "Type 2 diabetes mellitus" to the individual elements of "a blood sugar level of the certain amount" and "various other symptoms".

The indicia extracted from the unstructured data may be correlated with one or more closely matching knowledge graphs by comparing similarities between the indicia and the individual elements. Tags related to possible health related information may be generated and associated with the indicia in the unstructured data. For example, the tags may specify "A leads to B" (where A is a health related information and B is another health related information), "B causes C" (where C is yet another health related information), "C has complications of D" (where D is yet another health related information), and so forth. These tags associated with the indicia may be correlated with the logical structure (e.g., predicates of the logical structure) based on structural similarity to generate cognified data. For example, if a person exhibits certain symptoms and has certain laboratory tests performed, then that person may have a certain medical condition (e.g., type 2 diabetes mellitus) that is identified in the knowledge graphs using the logical structures.

A pattern may be detected by identifying structural similarities between the tags and the logical structure in order to generate the cognified data. Cognification may refer to instilling intelligence into something. In the present disclosure, unstructured data may be cognified into cognified data by instilling intelligence into the unstructured data using the knowledge graph and the logical structure. The cognified data may include a summary of a health related condition of a patient, where the summary includes insights, conclusions, recommendations, identified gaps (e.g., in treatment, risk, quality of care, guidelines, etc.), and so forth.

The cognified data may be presented on a computing device of a physician. Instead of reading pages and pages of digital medical charts (EMRs) for a patient, the physician may read the cognified data that presents pointed summarized information that can be utilized to more efficiently and effectively treat the patient. As a result, computing resources may be saved by preventing numerous searches for EMRs and preventing accessing numerous screens displaying the EMRs. In some embodiments, the physician may submit feedback pertaining to whether or not the cognified data is accurate for the patient. The feedback may be used to update the artificial intelligence engine that uses the knowledge graph and logical structure to generate the cognified data.

In some embodiments, the cognified data may be used to diagnose a medical condition of the patient. For example, the medical condition may be diagnosed if a threshold criteria is satisfied. The threshold criteria may include matching a certain number of predicates and tags for a particular medical condition represented by a particular knowledge graph. The computing device of the physician and/or the patient may present the diagnosis and a degree of certainty based on the threshold criteria. In some embodiments, the physician may submit feedback pertaining to whether or not the diagnosis is accurate for the patient. The feedback may be used to update the artificial intelligence engine that uses the knowledge graph and logical structure to generate the diagnosis using the cognified data.

Further, patients may be inundated with information about a particular medical condition with which they are diagnosed and/or inquiring about. The information may not be relevant to a particular stage of the medical condition. The amount of information may waste memory resources of the computing device of the patient. Also, the use may have a bad experience using the computing device due to the overwhelming amount of information.

In some embodiments, user experience of using a computing device may be enhanced by running an application that performs various techniques described herein. The user may be interacting with the cognitive agent and the cognitive agent may be steering the conversation as described herein. In some embodiments, the cognitive agent may provide recommendations based on the text entered by the user, and/or patient notes in EMRs, which may be transformed into cognified data. The application may present health related information, such as the cognified data, pertaining to the medical condition to the computing device of the patient and/or the physician.

Instead of overwhelming the patient with massive amounts of information about the medical condition, the distribution of information may be regulated to the computing device of the patient and/or the physician. For example, if the patient is diagnosed as having type 2 diabetes mellitus, a controlled traversing of the knowledge graph associated with type 2 diabetes mellitus may be performed to provide information to the patient. The traversal may begin at a root node of the knowledge graph and first health related information may be provided to the computing device of the patient at a first time. The first health related information may pertain to a name of the medical condition, a definition of the possible medical condition, or some combination thereof. At a second time, health related information associated with a second node of the knowledge graph may be provided to the computing device of the patient. The second health related information may pertain to how the medical condition affects people, signs and symptoms of the medical condition, a way to treat the medical condition, complications of the medical condition, a progression of the medical condition, or some combination thereof. The health related information associated with the remaining nodes in the knowledge graph may be distributed to the computing device of the patient at different respective times. In some embodiments, the health related information to be provided and/or the times at which the health related information is provided may be selected based on relevancy to a stage of the medical condition of the patient.

The described methods and systems are described as occurring in the healthcare space, though other areas are also contemplated.

FIG. 1 shows a system architecture 100 that can be configured to provide a population health management service, in accordance with various embodiments. Specifically, FIG. 1 illustrates a high-level overview of an overall architecture that includes a cognitive intelligence platform 102 communicably coupled to a user device 104. The cognitive intelligence platform 102 includes several computing devices, where each computing device, respectively, includes at least one processor, at least one memory, and at least one storage (e.g., a hard drive, a solid-state storage device, a mass storage device, and a remote storage device). The individual computing devices can represent any form of a computing device such as a desktop computing device, a rack-mounted computing device, and a server device. The foregoing example computing devices are not meant to be limiting. On the contrary, individual computing devices implementing the cognitive intelligence platform 102 can represent any form of computing device without departing from the scope of this disclosure.

The several computing devices work in conjunction to implement components of the cognitive intelligence platform 102 including: a knowledge cloud 106; a critical thinking engine 108; a natural language database 122; and a cognitive agent 110. The cognitive intelligence platform 102 is not limited to implementing only these components, or in the manner described in FIG. 1. That is, other system architectures can be implemented, with different or additional components, without departing from the scope of this disclosure. The example system architecture 100 illustrates one way to implement the methods and techniques described herein.

The knowledge cloud 106 represents a set of instructions executing within the cognitive intelligence platform 102 that implement a database configured to receive inputs from several sources and entities. For example, some of the sources and entities include a service provider 112, a facility 114, and a microsurvey 116—each described further below.

The critical thinking engine 108 represents a set of instructions executing within the cognitive intelligence platform 102 that execute tasks using artificial intelligence, such as recognizing and interpreting natural language (e.g., performing conversational analysis), and making decisions in a linear manner (e.g., in a manner similar to how the human left brain processes information). Specifically, an ability of the cognitive intelligence platform 102 to understand natural language is powered by the critical thinking engine 108. In various embodiments, the critical thinking engine 108 includes a natural language database 122. The natural language database 112 includes data curated over at least thirty years by linguists and computer data scientists, including data related to speech patterns, speech equivalents, and algorithms directed to parsing sentence structure.

Furthermore, the critical thinking engine 108 is configured to deduce causal relationships given a particular set of data, where the critical thinking engine 108 is capable of taking the individual data in the particular set, arranging the individual data in a logical order, deducing a causal relationship between each of the data, and drawing a conclusion. The ability to deduce a causal relationship and draw a conclusion (referred to herein as a "causal" analysis) is in direct contrast to other implementations of artificial intelligence that mimic the human left brain processes. For example, the other implementations can take the individual data and analyze the data to deduce properties of the data or statistics associated with the data (referred to herein as an "analytical" analysis). However, these other implementations are unable to perform a causal analysis—that is, deduce a causal relationship and draw a conclusion from the particular set of data. As described further below—the critical thinking engine 108 is capable of performing both types of analysis: causal and analytical.

In some embodiments, the critical thinking engine 108 includes an artificial intelligence engine 109 ("AI Engine" in FIG. 1) that uses one or more machine learning models. The one or more machine learning models may be generated by a training engine and may be implemented in computer instructions that are executable by one or more processing device of the training engine, the artificial intelligence engine 109, another server, and/or the user device 104. To generate the one or more machine learning models, the training engine may train, test, and validate the one or more machine learning models. The training engine may be a rackmount server, a router computer, a personal computer, a portable digital assistant, a smartphone, a laptop computer, a tablet computer, a camera, a video camera, a netbook, a desktop computer, a media center, or any combination of the above. The one or more machine learning models may refer to model artifacts that are created by the training engine using training data that includes training inputs and corresponding target outputs. The training engine may find patterns in the training data that map the training input to the target output, and generate the machine learning models that capture these patterns.

The one or more machine learning models may be trained to generate one or more knowledge graphs each pertaining to a particular medical condition. The knowledge graphs may include individual elements (nodes) that are linked via predicates of a logical structure. The logical structure may use any suitable order of logic (e.g., higher order logic and/or Nth order logic). Higher order logic may be used to admit quantification over sets that are nested arbitrarily deep. Higher order logic may refer to a union of first-, second-, third, . . . , Nth order logic. Clinical-based evidence, clinical trials, physician research, and the like that includes various information (e.g., knowledge) pertaining to different medical conditions may be input as training data to the one or more machine learning models. The information may pertain to facts, properties, attributes, concepts, conclusions, risks, correlations, complications, etc. of the medical conditions. Keywords, phrases, sentences, cardinals, numbers, values, objectives, nouns, verbs, concepts, and so forth may be specified (e.g., labeled) in the information such that the machine learning models learn which ones are associated with the medical conditions. The information may specify predicates that correlates the information in a logical structure such that the machine learning models learn the logical structure associated with the medical conditions.

In some embodiments, the one or more machine learning models may be trained to transform input unstructured data (e.g., patient notes) into cognified data using the knowledge graph and the logical structure. The machine learning models may identify indicia in the unstructured data and compare the indicia to the knowledge graphs to generate possible health related information (e.g., tags) pertaining to the patient. The possible health related information may be associated with the indicia in the unstructured data. The one or more machine learning models may also identify, using the logical structure, a structural similarity of the possible health related information and a known predicate in the logical structure. The structural similarity between the possible health related information and the known predicate may enable identifying a pattern (e.g., treatment patterns, education and content patterns, order patterns, referral patterns, quality of care patterns, risk adjustment patterns, etc.). The one or more machine learning models may generate the cognified data based on the structural similarity and/or the pattern identified. Accordingly, the machine learning models may use a combination of knowledge graphs, logical structures, structural similarity comparison mechanisms, and/or pattern recognition to generate the cognified data. The cognified data may be output by the one or more trained machine learning models.

The cognified data may provide a summary of the medical condition of the patient. A diagnosis of the patient may be generated based on the cognified data. The summary of the medical condition may include one or more insights not present in the unstructured data. The summary may identify gaps in the unstructured data, such as treatment gaps (e.g., should prescribe medication, should provide different medication, should change dosage of medication, etc.), risk gaps (e.g., the patient is at risk for cancer based on familial history and certain lifestyle behaviors), quality of care gaps (e.g., need to check-in with the patient more frequently), and so forth. The summary of the medical condition may include one or more conclusions, recommendations, complications, risks, statements, causes, symptoms, etc. pertaining to the medical condition. In some embodiments, the summary of the medical condition may indicate another medical condition that the medical condition can lead to. Accordingly, the cognified data represents intelligence, knowledge, and logic cognified from unstructured data.

In some embodiments, the cognified data may be reviewed by physicians and the physicians may provide feedback pertaining to whether or not the cognified data is accurate. Also, the physicians may provide feedback pertaining to whether or not the diagnosis generated using the cognified data is accurate. This feedback may be used to update the one or more machine learning models to improve their accuracy.

The cognitive agent 110 represents a set of instructions executing within the cognitive intelligence platform 102 that implement a client-facing component of the cognitive intelligence platform 102. The cognitive agent 110 is an interface between the cognitive intelligence platform 102 and the user device 104. And in some embodiments, the cognitive agent 110 includes a conversation orchestrator 124 that determines pieces of communication that are presented to the user device 104 (and the user). When a user of the user device 104 interacts with the cognitive intelligence platform 102, the user interacts with the cognitive agent 110. The several references herein, to the cognitive agent 110 performing a method, can implicate actions performed by the critical thinking engine 108, which accesses data in the knowledge cloud 106 and the natural language database 122.

In various embodiments, the several computing devices executing within the cognitive intelligence platform are communicably coupled by way of a network/bus interface. Furthermore, the various components (e.g., the knowledge cloud 106, the critical thinking engine 108, and the cognitive agent 110), are communicably coupled by one or more inter-host communication protocols 118. In one example, the knowledge cloud 106 is implemented using a first computing device, the critical thinking engine 108 is implemented using a second computing device, and the cognitive agent 110 is implemented using a third computing device, where each of the computing devices are coupled by way of the inter-host communication protocol 118. Although in this example, the individual components are described as executing on separate computing devices this example is not meant to be limiting, the components can be implemented on the same computing device, or partially on the same computing device, without departing from the scope of this disclosure.

The user device 104 represents any form of a computing device, or network of computing devices, e.g., a personal computing device, a smart phone, a tablet, a wearable computing device, a notebook computer, a media player device, and a desktop computing device. The user device 104 includes a processor, at least one memory, and at least one storage. A user uses the user device 104 to input a given text posed in natural language (e.g., typed on a physical keyboard, spoken into a microphone, typed on a touch screen, or combinations thereof) and interacts with the cognitive intelligence platform 102, by way of the cognitive agent 110.

The architecture 100 includes a network 120 that communicatively couples various devices, including the cognitive intelligence platform 102 and the user device 104. The network 120 can include local area network (LAN) and wide area networks (WAN). The network 102 can include wired technologies (e.g., Ethernet®) and wireless technologies (e.g., Wi-Fi®, code division multiple access (CDMA), global system for mobile (GSM), universal mobile telephone service (UMTS), Bluetooth®, and ZigBee®. For example, the user device 104 can use a wired connection or a wireless technology (e.g., Wi-Fi®) to transmit and receive data over the network 120.

Still referring to FIG. 1, the knowledge cloud 106 is configured to receive data from various sources and entities and integrate the data in a database. An example source that provides data to the knowledge could 106 is the service provider 112, an entity that provides a type of service to a user. For example, the service provider 112 can be a health service provider (e.g., a doctor's office, a physical therapist's office, a nurse's office, or a clinical social worker's office), and a financial service provider (e.g., an accountant's office). For purposes of this discussion, the cognitive intelligence platform 102 provides services in the health industry, thus the examples discussed herein are associated with the health industry. However, any service industry can benefit from the disclosure herein, and thus the examples associated with the health industry are not meant to be limiting.

Throughout the course of a relationship between the service provider 112 and a user (e.g., the service provider 112 provides healthcare to a patient), the service provider 112 collects and generates data associated with the patient or the user, including health records that include doctor's notes about the patient and prescriptions, billing records, and insurance records. The service provider 112, using a computing device (e.g., a desktop computer or a tablet), provides the data associated with the user to the cognitive intelligence platform 102, and more specifically the knowledge cloud 106.

Another example source that provides data to the knowledge cloud 106 is the facility 114. The facility 114 represents a location owned, operated, or associated with any entity including the service provider 112. As used herein, an entity represents an individual or a collective with a distinct and independent existence. An entity can be legally recognized (e.g., a sole proprietorship, a partnership, a corporation) or less formally recognized in a community. For example, the entity can include a company that owns or operates a gym (facility). Additional examples of the facility 114 include, but is not limited to, a hospital, a trauma center, a clinic, a dentist's office, a pharmacy, a store (including brick and mortar stores and online retailers), an out-patient care center, a specialized care center, a birthing center, a gym, a cafeteria, and a psychiatric care center.

As the facility 114 represents a large number of types of locations, for purposes of this discussion and to orient the reader by way of example, the facility 114 represents the doctor's office or a gym. The facility 114 generates additional data associated with the user such as appointment times, an attendance record (e.g., how often the user goes to the gym), a medical record, a billing record, a purchase record, an order history, and an insurance record. The facility 114, using a computing device (e.g., a desktop computer or a tablet), provides the data associated with the user to the cognitive intelligence platform 102, and more specifically the knowledge cloud 106.

An additional example source that provides data to the knowledge cloud 106 is the microsurvey 116. The microsurvey 116 represents a tool created by the cognitive intelligence platform 102 that enables the knowledge cloud 106 to collect additional data associated with the user. The microsurvey 116 is originally provided by the cognitive intelligence platform 102 (by way of the cognitive agent 110) and the user provides data responsive to the microsurvey 116 using the user device 104. Additional details of the microsurvey 116 are described below.

Yet another example source that provides data to the knowledge cloud 106, is the cognitive intelligence platform 102, itself. In order to address the care needs and well-being of the user, the cognitive intelligence platform 102 collects, analyzes, and processes information from the user, healthcare providers, and other eco-system participants, and consolidates and integrates the information into knowledge. For example, clinical-based evidence and guidelines may be obtained by the cognitive intelligence platform 102 and used as knowledge. The knowledge can be shared with the user and stored in the knowledge cloud 106.

In various embodiments, the computing devices used by the service provider 112 and the facility 114 are communicatively coupled to the cognitive intelligence platform 102, by way of the network 120. While data is used individually by various entities including: a hospital, practice group, facility, or provider, the data is less frequently integrated and seamlessly shared between the various entities in the current art. The cognitive intelligence platform 102 provides a solution that integrates data from the various entities. That is, the cognitive intelligence platform 102 ingests, processes, and disseminates data and knowledge in an accessible fashion, where the reason for a particular answer or dissemination of data is accessible by a user.

In particular, the cognitive intelligence platform 102 (e.g., by way of the cognitive agent 110 interacting with the user) holistically manages and executes a health plan for durational care and wellness of the user (e.g., a patient or consumer). The health plan includes various aspects of durational management that is coordinated through a care continuum.

The cognitive agent 110 can implement various personas that are customizable. For example, the personas can include knowledgeable (sage), advocate (coach), and witty friend (jester). And in various embodiments, the cognitive agent 110 persists with a user across various interactions (e.g., conversations streams), instead of being transactional or transient. Thus, the cognitive agent 110 engages in dynamic conversations with the user, where the cognitive intelligence platform 102 continuously deciphers topics that a user wants to talk about. The cognitive intelligence platform 102 has relevant conversations with the user by ascertaining topics of interest from a given text posed in a natural language input by the user. Additionally the cognitive agent 110 connects the user to healthcare service providers, hyperlocal health communities, and a variety of services and tools/devices, based on an assessed interest of the user.

As the cognitive agent 110 persists with the user, the cognitive agent 110 can also act as a coach and advocate while delivering pieces of information to the user based on tonal knowledge, human-like empathies, and motivational dialog within a respective conversational stream, where the conversational stream is a technical discussion focused on a specific topic. Overall, in response to a question—e.g., posed by the user in natural language—the cognitive intelligence platform 102 consumes data from and related to the user and computes an answer. The answer is generated using a rationale that makes use of common sense knowledge, domain knowledge, evidence-based medicine guidelines, clinical ontologies, and curated medical advice. Thus, the content displayed by the cognitive intelligence platform 102 (by way of the cognitive agent 110) is customized based on the language used to communicate with the user, as well as factors such as a tone, goal, and depth of topic to be discussed.

Overall, the cognitive intelligence platform 102 is accessible to a user, a hospital system, and physician. Additionally, the cognitive intelligence platform 102 is accessible to paying entities interested in user behavior—e.g., the outcome of physician-consumer interactions in the context of disease or the progress of risk management. Additionally, entities that provides specialized services such as tests, therapies, and clinical processes that need risk based interactions can also receive filtered leads from the cognitive intelligence platform 102 for potential clients.

Conversational Analysis

In various embodiments, the cognitive intelligence platform 102 is configured to perform conversational analysis in a general setting. The topics covered in the general setting is driven by the combination of agents (e.g., cognitive agent 110) selected by a user. In some embodiments, the cognitive intelligence platform 102 uses conversational analysis to identify the intent of the user (e.g., find data, ask a question, search for facts, find references, and find products) and a respective micro-theory in which the intent is logical.

For example, the cognitive intelligence platform 102 applies conversational analysis to decode what the user is asking or stated, where the question or statement is in free form language (e.g., natural language). Prior to determining and sharing knowledge (e.g., with the user or the knowledge cloud 106), using conversational analysis, the cognitive intelligence platform 102 identifies an intent of the user and overall conversational focus.

The cognitive intelligence platform 102 responds to a statement or question according to the conversational focus and steers away from another detected conversational focus so as to focus on a goal defined by the cognitive agent 110. Given an example statement of a user, "I want to fly out tomorrow," the cognitive intelligence platform 102 uses conversational analysis to determine an intent of the statement. Is the user aspiring to be bird-like or does he want to travel? In the former case, the micro-theory is that of human emotions whereas in the latter case, the micro-theory is the world of travel. Answers are provided to the statement depending on the micro-theory in which the intent logically falls.

The cognitive intelligence platform 102 utilize a combination of linguistics, artificial intelligence, and decision trees to decode what a user is asking or stating. The discussion includes methods and system design considerations and results from an existing embodiment. Additional details related to conversational analysis are discussed next.

Analyzing Conversational Context as Part of Conversational Analysis

For purposes of this discussion, the concept of analyzing conversational context as part of conversational analysis is now described. To analyze conversational context, the following steps are taken: 1) obtain text (e.g., receive a question) and perform translations; 2) understand concepts, entities, intents, and micro-theory; 3) relate and search; 4) ascertain the existence of related concepts; 5) logically frame concepts or needs; 6) understand the questions that can be answered from available data; and 7) answer the question. Each of the foregoing steps is discussed next, in turn.

Step 1: Obtain Text/Question and Perform Translations In various embodiments, the cognitive intelligence platform 102 (FIG. 1) receives a text or question and performs translations as appropriate. The cognitive intelligence platform 102 supports various methods of input including text received from a touch interface (e.g., options presented in a microsurvey), text input through a microphone (e.g., words spoken into the user device), and text typed on a keyboard or on a graphical user interface. Additionally, the cognitive intelligence platform 102 supports multiple languages and auto translation (e.g., from English to Traditional/Simplified Chinese or vice versa).

The example text below is used to described methods in accordance with various embodiments herein:

"One day in January 1913. G. H. Hardy, a famous Cambridge University mathematician received a letter from an Indian named Srinivasa Ramanujan asking him for his opinion of 120 mathematical theorems that Ramanujan said he had discovered. To Hardy, many of the theorems made no sense. Of the others, one or two were already well-known. Ramanujan must be some kind of trickplayer, Hardy decided, and put the letter aside. But all that day the letter kept hanging round Hardy. Might there by something in those wild-looking theorems?

That evening Hardy invited another brilliant Cambridge mathematician, J. E. Littlewood, and the two men set out to assess the Indian's worth. That incident was a turning point in the history of mathematics.

At the time, Ramanujan was an obscure Madras Port Trust clerk. A little more than a year later, he was at Cambridge University, and beginning to be recognized as one of the most amazing mathematicians the world has ever known. Though he died in 1920, much of his work was so far in advance of his time that only in recent years is it beginning to be properly understood.

Indeed, his results are helping solve today's problems in computer science and physics, problems that he could have had no notion of.

For Indians, moreover, Ramanujan has a special significance. Ramanujan, through born in poor and ill-paid accountant's family 100 years ago, has inspired many Indians to adopt mathematics as career.

Much of Ramanujan's work is in number theory, a branch of mathematics that deals with the subtle laws and relationships that govern numbers.

Mathematicians describe his results as elegant and beautiful but they are much too complex to be appreciated by laymen.

His life, though, is full of drama and sorrow. It is one of the great romantic stories of mathematics, a distressing reminder that genius can surface and rise in the most unpromising circumstances."

The cognitive intelligence platform 102 analyzes the example text above to detect structural elements within the example text (e.g., paragraphs, sentences, and phrases). In some embodiments, the example text is compared to other sources of text such as dictionaries, and other general fact databases (e.g., Wikipedia) to detect synonyms and common phrases present within the example text.

Step 2: Understand Concept, Entity, Intent, and Micro-Theory

In step 2, the cognitive intelligence platform 102 parses the text to ascertain concepts, entities, intents, and micro-theories. An example output after the cognitive intelligence platform 102 initially parses the text is shown below, where concepts, and entities are shown in bold.

"One day in January 1913. G. H. Hardy, a famous Cambridge University mathematician received a letter from an Indian named Srinivasa Ramanujan asking him for his opinion of 120 mathematical theorems that Ramanujan said he had discovered. To Hardy, many of the theorems made no sense. Of the others, one or two were already well-known. Ramanujan must be some kind of trickplayer, Hardy decided, and put the letter aside. But all that day the letter kept hanging round Hardy. Might there by something in those wild-looking theorems?

That evening Hardy invited another brilliant Cambridge mathematician, J. E. Littlewood, and the two men set out to assess the Indian's worth. That incident was a turning point in the history of mathematics.

At the time, Ramanujan was an obscure Madras Port Trust clerk. A little more than a year later, he was at Cambridge University, and beginning to be recognized as one of the most amazing mathematicians the world has ever known. Though he died in 1920, much of his work was so far in advance of his time that only in recent years is it beginning to be properly understood.

Indeed, his results are helping solve today's problems in computer science and physics, problems that he could have had no notion of.

For Indians, moreover, Ramanujan has a special significance. Ramanujan, through born in poor and ill-paid accountant's family 100 years ago, has inspired many Indians to adopt mathematics as career. Much of Ramanujan's work is in number theory, a branch of mathematics that deals with the subtle laws and relationships that govern numbers. Mathematicians describe his results as elegant and beautiful but they are much too complex to be appreciated by laymen.

His life, though, is full of drama and sorrow. It is one of the great romantic stories of mathematics, a distressing reminder that genius can surface and rise in the most unpromising circumstances."

For example, the cognitive intelligence platform 102 ascertains that Cambridge is a university—which is a full understanding of the concept. The cognitive intelligence platform (e.g., the cognitive agent 110) understands what humans do in Cambridge, and an example is described below in which the cognitive intelligence platform 102 performs steps to understand a concept.

For example, in the context of the above example, the cognitive agent 110 understands the following concepts and relationships:

Cambridge employed John Edensor Littlewood (1)
Cambridge has the position Ramanujan's position at Cambridge University (2)
Cambridge employed G. H. Hardy. (3)

The cognitive agent 110 also assimilates other understandings to enhance the concepts, such as:

Cambridge has Trinity College as a suborganization. (4)
Cambride is located in Cambridge. (5)
Alan Turing is previously enrolled at Cambridge. (6)
Stephen Hawking attended Cambridge. (7)

The statements (1)-(7) are not picked at random. Instead the cognitive agent 110 dynamically constructs the statements (1)-(7) from logic or logical inferences based on the example text above. Formally, the example statements (1)-(7) are captured as follows:

(#$subOrganizations #$UniversityOfCambridge #$TrinityCollege-Cambridge-England) (8)

(#$placeInCity #$UniversityOfCambridge #$CityofCambridgeEngland) (9)

(#$schooling #$AlanTuring #$UniversityOfCambridge #$PreviouslyEnrolled)(10)

(#$hasAlumni #$UniversityOfCambridge #$StephenHawking) (11)

Step 3: Relate and Search

Next, in step 3, the cognitive agent 110 relates various entities and topics and follows the progression of topics in the example text. Relating includes the cognitive agent 110 understanding the different instances of Hardy are all the same person, and the instances of Hardy are different from the instances of Littlewood. The cognitive agent 110 also understands that the instances Hardy and Littlewood share some similarities—e.g., both are mathematicians and they did some work together at Cambridge on Number Theory. The ability to track this across the example text is referred to as following the topic progression with a context.

Step 4: Ascertain the Existence of Related Concepts

Next, in Step 4, the cognitive agent 110 asserts non-existent concepts or relations to form new knowledge. Step 4 is an optional step for analyzing conversational context. Step 4 enhances the degree to which relationships are understood or different parts of the example text are understood together. If two concepts appear to be separate—e.g., a relationship cannot be graphically drawn or logically expressed between enough sets of concepts—there is a barrier to understanding. The barriers are overcome by expressing additional relationships. The additional relationships can be discovered using strategies like adding common sense or general knowledge sources (e.g., using the common sense data 208) or adding in other sources including a lexical variant database, a dictionary, and a thesaurus.

One example of concept progression from the example text is as follows: the cognitive agent 110 ascertains the phrase "theorems that Ramanujan said he had discovered" is related to the phrase "his results", which is related to "Ramanujan's work is in number theory, a branch of mathematics that deals with the subtle laws and relationships that govern numbers."

Step 5: Logically Frame Concepts or Needs

In Step 5, the cognitive agent 110 determines missing parameters—which can include for example, missing entities, missing elements, and missing nodes—in the logical framework (e.g., with a respective micro-theory). The cognitive agent 110 determines sources of data that can inform the missing parameters. Step 5 can also include the cognitive agent 110 adding common sense reasoning and finding logical paths to solutions.

With regards to the example text, some common sense concepts include:

Mathematicians develop Theorems. (12)
Theorems are hard to comprehend. (13)
Interpretations are not apparent for years. (14)
Applications are developed over time. (15)
Mathematicians collaborate and assess work. (16)

With regards to the example text, some passage concepts include:

Ramanujan did Theorems in Early 20th Century. (17)
Hardy assessed Ramanujan's Theorems. (18)
Hardy collaborated with Littlewood. (19)
Hardy and Littlewood assessed Ramanujan's work (20)

Within the micro-theory of the passage analysis, the cognitive agent 110 understands and catalogs available paths to answer questions. In Step 5, the cognitive agent 110 makes the case that the concepts (12)-(20) are expressed together.

Step 6: Understand the Questions that can be Answered from Available Data

In Step 6, the cognitive agent 110 parses sub-intents and entities. Given the example text, the following questions are answerable from the cognitive agent's developed understanding of the example text, where the understanding was developed using information and context ascertained from the example text as well as the common sense data 208 (FIG. 2):

What situation causally contributed to Ramanujan's position at Cambridge? (21)

Does the author of the passage regret that Ramanujan died prematurely? (22)

Does the author of the passage believe that Ramanujan is a mathematical genius?(23)

Based on the information that is understood by the cognitive agent 110, the questions (21)-(23) can be answered.

By using an exploration method such as random walks, the cognitive agent 110 makes a determination as the paths that are plausible and reachable with the context (e.g., micro-theory) of the example text. Upon explorations, the cognitive agent 110 catalogs a set of meaningful questions. The set of meaningful questions are not asked, but instead explored based on the cognitive agent's understanding of the example text.

Given the example text, an example of exploration that yields a positive result is: "a situation X that caused Ramanujan's position." In contrast, an example of exploration that causes irrelevant results is: "a situation Y that caused Cambridge." The cognitive agent 110 is able to deduce that the latter exploration is meaningless, in the context of a micro-theory, because situations do not cause universities. Thus the cognitive agent 110 is able to deduce, there are no answers to Y, but there are answers to X.

Step 7: Answer the Question

In Step 7, the cognitive agent 110 provides a precise answer to a question. For an example question such as: "What situation causally contributed to Ramanujan's position at Cambridge?" the cognitive agent 110 generates a precise answer using the example reasoning:

HardyandLittlewoodsEvaluatingOfRamanujansWork (24)
HardyBeliefThatRamanujanIsAnExpertInMathematics (25)
HardysBeliefThatRamanujanIsAnExpertInMathematicsAndAGenius (26)

In order to generate the above reasoning statements (24)-(26), the cognitive agent 110 utilizes a solver or prover in the context of the example text's micro-theory—and associated facts, logical entities, relations, and assertions. As an additional example, the cognitive agent 110 uses a reasoning library that is optimized for drawing the example conclusions above within the fact, knowledge, and inference space (e.g., work space) that the cognitive agent 110 maintains.

By implementing the steps 1-7, the cognitive agent 110 analyzes conversational context. The described method for analyzing conversation context can also be used for recommending items in conversations streams. A conversational stream is defined herein as a technical discussion focused on specific topics. As related to described examples herein, the specific topics relate to health (e.g., diabetes). Throughout the lifetime of a conversational stream, a cognitive agent 110 collect information over may channels such as chat, voice, specialized applications, web browsers, contact centers, and the like.

By implementing the methods to analyze conversational context, the cognitive agent 110 can recommend a variety of topics and items throughout the lifetime of the conversational stream. Examples of items that can be recommended by the cognitive agent 110 include: surveys, topics of interest, local events, devices or gadgets, dynamically adapted health assessments, nutritional tips, reminders from a health events calendar, and the like.

Accordingly, the cognitive intelligence platform 102 provides a platform that codifies and takes into consideration a set of allowed actions and a set of desired outcomes. The cognitive intelligence platform 102 relates actions, the sequences of subsequent actions (and reactions), desired sub-outcomes, and outcomes, in a way that is transparent and logical (e.g., explainable). The cognitive intelligence platform 102 can plot a next best action sequence and a planning basis (e.g., health care plan template, or a financial goal achievement template), also in a manner that is explainable. The cognitive intelligence platform 102 can utilize a critical thinking engine 108 and a natural language database 122 (e.g., a linguistics and natural language understanding system) to relate conversation material to actions.

For purposes of this discussion, several examples are discussed in which conversational analysis is applied within the field of durational and whole-health management for a user. The discussed embodiments holistically address the care needs and well-being of the user during the course of his life. The methods and systems described herein can also be used in fields outside of whole-health management, including: phone companies that benefits from a cognitive agent; hospital systems or physicians groups that want to coach and educate patients; entities interested in user behavior and the outcome of physician-consumer interactions in terms of a progress of disease or risk management; entities that provide specialized services (e.g., test, therapies, clinical processes) to filter leads; and sellers, merchants, stores and big box retailers that want to understand which product to sell.

In addition, the conversational analysis may include cognifying the text input by the user. For example, if the user states (e.g., text, voice) they have various symptoms, the cognification techniques disclosed herein may be performed to construct cognified data using the text input. The user may input text specifying that they have a level of 5.7 mmol/L blood sugar. The cognitive intelligence platform 102 may cognify the text to output that the level of blood sugar is within acceptable limits, and that blood sugar testing was used to measure the blood sugar level. In some embodiments, the cognification techniques may be performed to generate a diagnosis of a medical condition of the patient. Further, the cognitive intelligence platform 102 may provide information to the user pertaining to the medical condition at a regulated pace.

Figure 2:
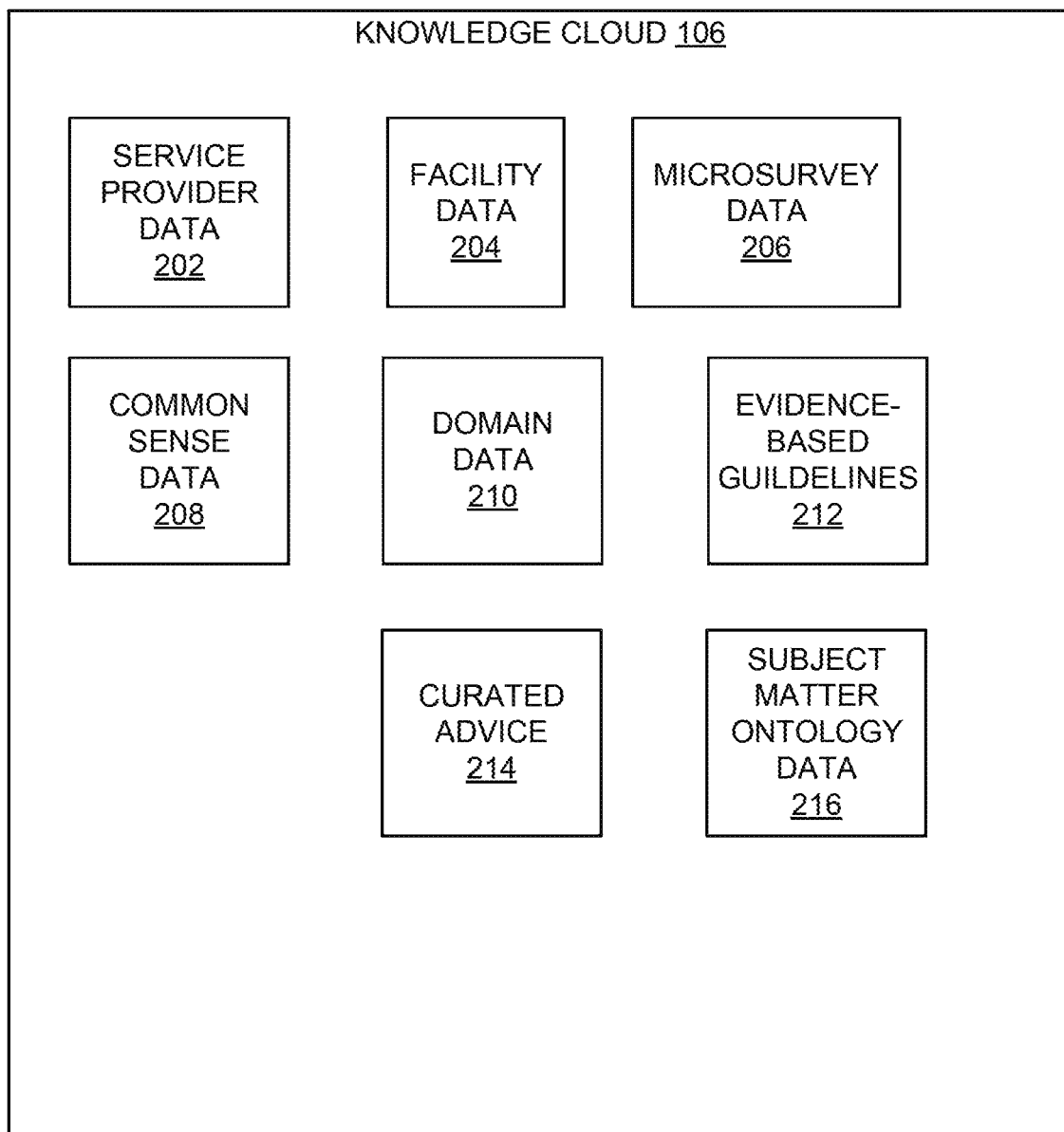
FIG. 2 shows additional details of a knowledge cloud, in accordance with various embodiments.

FIG. 2 shows additional details of a knowledge cloud, in accordance with various embodiments. In particular, FIG. 2 illustrates various types of data received from various sources, including service provider data 202, facility data 204, microsurvey data 206, commonsense data 208, domain data 210, evidence-based guidelines 212, subject matter ontology data 214, and curated advice 216. The types of data represented by the service provider data 202 and the facility data 204 include any type of data generated by the service provider 112 and the facility 114, and the above examples are not meant to be limiting. Thus, the example types of data are not meant to be limiting and other types of data can also be stored within the knowledge cloud 106 without departing from the scope of this disclosure.

The service provider data 202 is data provided by the service provider 112 (described in FIG. 1) and the facility data 204 is data provided by the facility 114 (described in FIG. 1). For example, the service provider data 202 includes medical records of a respective patient of a service provider 112 that is a doctor. In another example, the facility data 204 includes an attendance record of the respective patient, where the facility 114 is a gym. The microsurvey data 206 is data provided by the user device 104 responsive to questions presented in the microsurvey 116 (FIG. 1).

Common sense data 208 is data that has been identified as "common sense", and can include rules that govern a respective concept and used as glue to understand other concepts.

Domain data 210 is data that is specific to a certain domain or subject area. The source of the domain data 210 can include digital libraries. In the healthcare industry, for example, the domain data 210 can include data specific to the various specialties within healthcare such as, obstetrics, anesthesiology, and dermatology, to name a few examples. In the example described herein, the evidence-based guidelines 212 include systematically developed statements to assist practitioner and patient decisions about appropriate health care for specific clinical circumstances.

Curated advice 214 includes advice from experts in a subject matter. The curated advice 214 can include peer-reviewed subject matter, and expert opinions. Subject matter ontology data 216 includes a set of concepts and categories in a subject matter or domain, where the set of concepts and categories capture properties and relationships between the concepts and categories.

Figure 3:
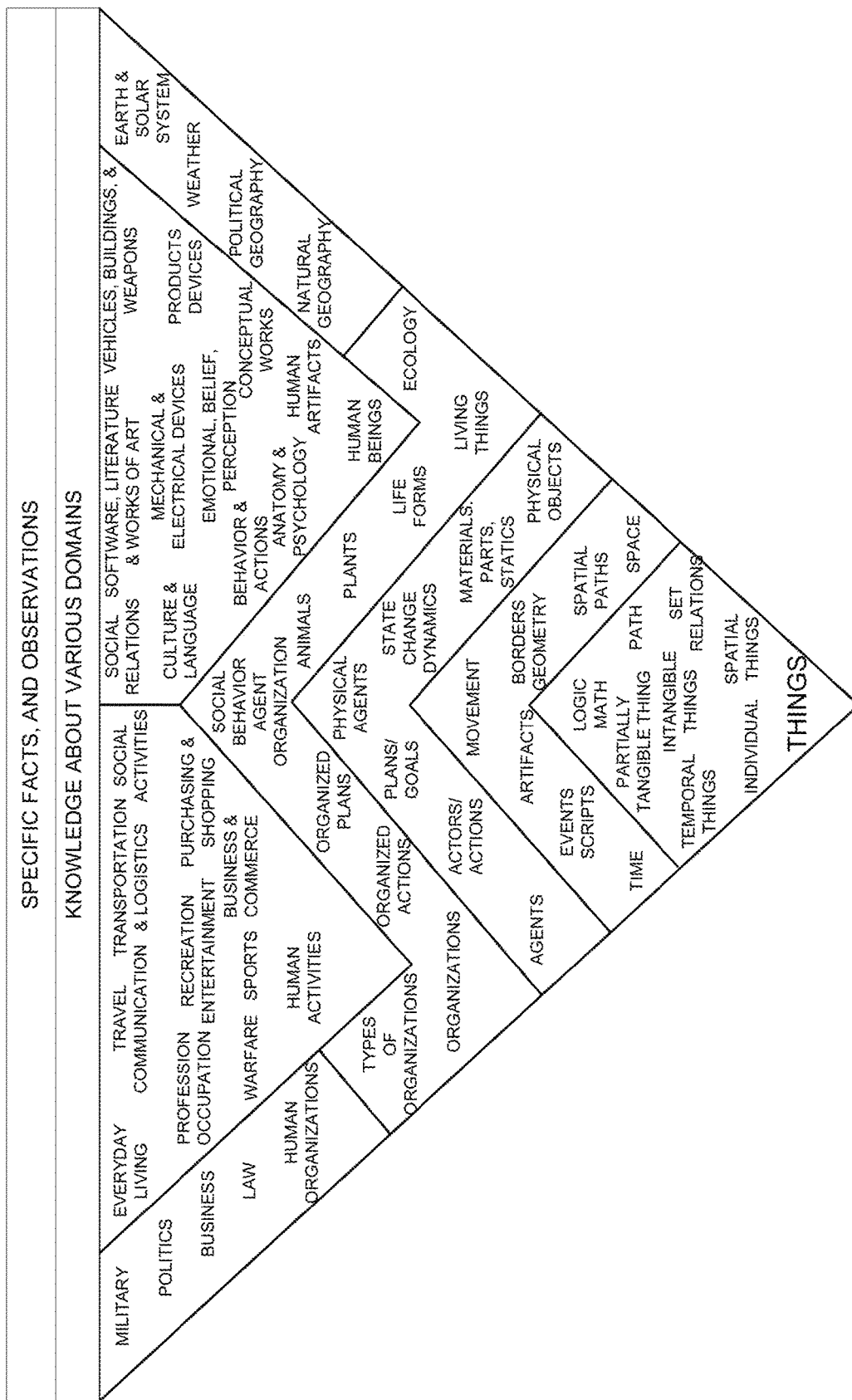
FIG. 3 shows an example subject matter ontology, in accordance with various embodiments.

In particular, FIG. 3 illustrates an example subject matter ontology 300 that is included as part of the subject matter ontology data 216.

Figure 4:
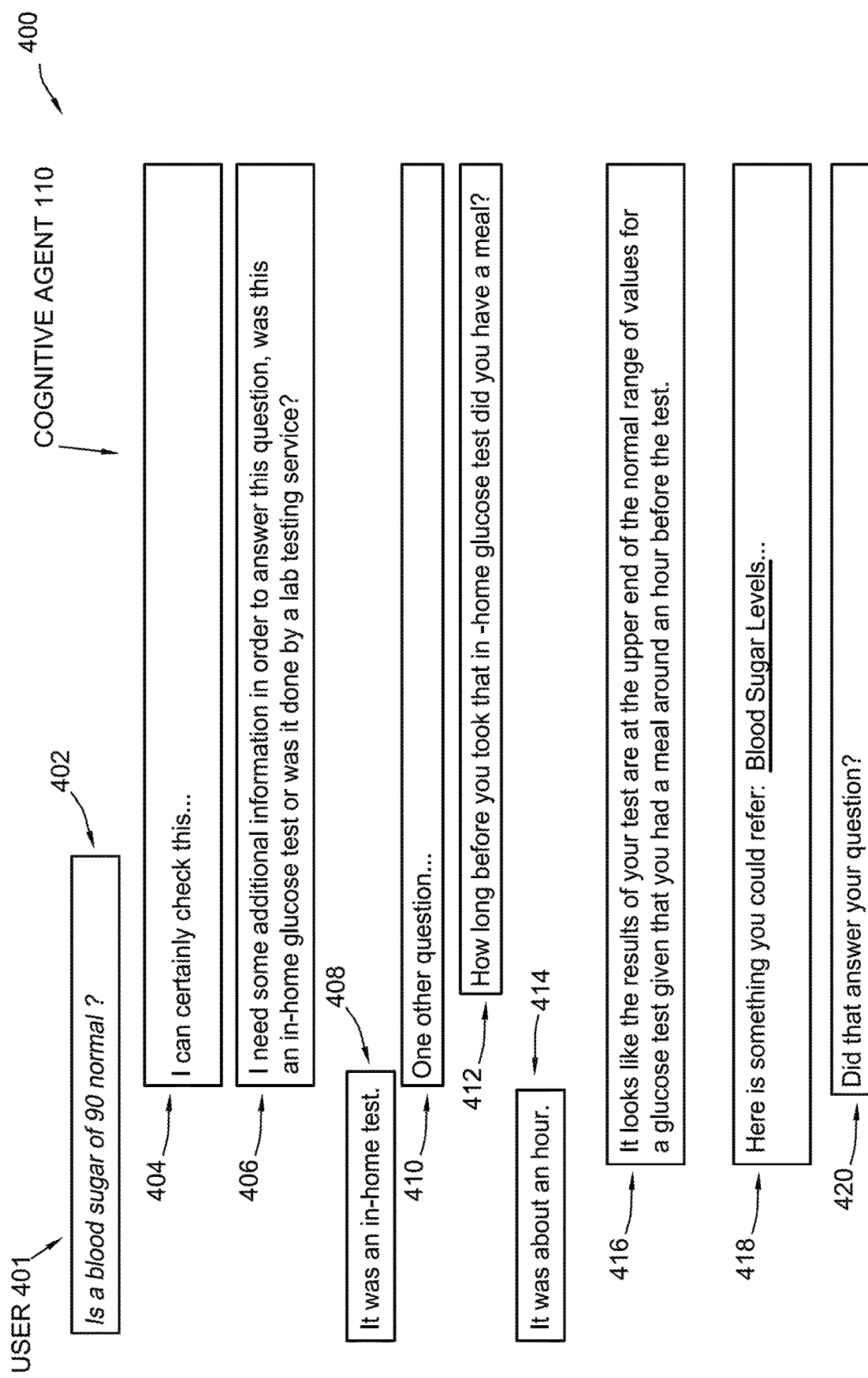
FIG. 4 shows aspects of a conversation, in accordance with various embodiments.

FIG. 4 illustrates aspects of a conversation 400 between a user and the cognitive intelligence platform 102, and more specifically the cognitive agent 110. For purposes of this discussion, the user 401 is a patient of the service provider 112. The user interacts with the cognitive agent 110 using a computing device, a smart phone, or any other device configured to communicate with the cognitive agent 110 (e.g., the user device 104 in FIG. 1). The user can enter text into the device using any known means of input including a keyboard, a touchscreen, and a microphone. The conversation 400 represents an example graphical user interface (GUI) presented to the user 401 on a screen of his computing device.

Initially, the user asks a general question, which is treated by the cognitive agent 110 as an "originating question." The originating question is classified into any number of potential questions ("pursuable questions") that are pursued during the course of a subsequent conversation. In some embodiments, the pursuable questions are identified based on a subject matter domain or goal. In some embodiments, classification techniques are used to analyze language (e.g., such as those outlined in HPS ID20180901-01_method for conversational analysis). Any known text classification technique can be used to analyze language and the originating question. For example, in line 402, the user enters an originating question about a subject matter (e.g., blood sugar) such as: "Is a blood sugar of 90 normal"? I In response to receiving an originating question, the cognitive intelligence platform 102 (e.g., the cognitive agent 110 operating in conjunction with the critical thinking engine 108) performs a first round of analysis (e.g., which includes conversational analysis) of the originating question and, in response to the first round of analysis, creates a workspace and determines a first set of follow up questions.

In various embodiments, the cognitive agent 110 may go through several rounds of analysis executing within the workspace, where a round of analysis includes: identifying parameters, retrieving answers, and consolidating the answers. The created workspace can represent a space where the cognitive agent 110 gathers data and information during the processes of answering the originating question. In various embodiments, each originating question corresponds to a respective workspace. The conversation orchestrator 124 can assess data present within the workspace and query the cognitive agent 110 to determine if additional data or analysis should be performed.

In particular, the first round of analysis is performed at different levels, including analyzing natural language of the text, and analyzing what specifically is being asked about the subject matter (e.g., analyzing conversational context). The first round of analysis is not based solely on a subject matter category within which the originating question is classified. For example, the cognitive intelligence platform 102 does not simply retrieve a predefined list of questions in response to a question that falls within a particular subject matter, e.g., blood sugar. That is, the cognitive intelligence platform 102 does not provide the same list of questions for all questions related to the particular subject matter. Instead, for example, the cognitive intelligence platform 102 creates dynamically formulated questions, curated based on the first round of analysis of the originating question.

In particular, during the first round of analysis, the cognitive agent 110 parses aspects of the originating question into associated parameters. The parameters represent variables useful for answering the originating question. For example, the question "is a blood sugar of 90 normal" may be parsed and associated parameters may include, an age of the inquirer, the source of the value 90 (e.g., in home test or a clinical test), a weight of the inquirer, and a digestive state of the user when the test was taken (e.g., fasting or recently eaten). The parameters identify possible variables that can impact, inform, or direct an answer to the originating question.

For purposes of the example illustrated in FIG. 4, in the first round of analysis, the cognitive intelligence platform 102 inserts each parameter into the workspace associated with the originating question (line 402). Additionally, based on the identified parameters, the cognitive intelligence platform 102 identifies a customized set of follow up questions ("a first set of follow-up questions). The cognitive intelligence platform 102 inserts first set of follow-up questions in the workspace associated with the originating question.

The follow up questions are based on the identified parameters, which in turn are based on the specifics of the originating question (e.g., related to an identified microtheory). Thus the first set of follow-up questions identified in response to, if a blood sugar is normal, will be different from a second set of follow up questions identified in response to a question about how to maintain a steady blood sugar.

After identifying the first set of follow up questions, in this example first round of analysis, the cognitive intelligence platform 102 determines which follow up question can be answered using available data and which follow-up question to present to the user. As described over the next few paragraphs, eventually, the first set of follow-up questions is reduced to a subset ("a second set of follow-up questions") that includes the follow-up questions to present to the user.

In various embodiments, available data is sourced from various locations, including a user account, the knowledge cloud 106, and other sources. Other sources can include a service that supplies identifying information of the user, where the information can include demographics or other characteristics of the user (e.g., a medical condition, a lifestyle). For example, the service can include a doctor's office or a physical therapist's office.

Another example of available data includes the user account. For example, the cognitive intelligence platform 102 determines if the user asking the originating question, is identified. A user can be identified if the user is logged into an account associated with the cognitive intelligence platform 102. User information from the account is a source of available data. The available data is inserted into the workspace of the cognitive agent 110 as a first data.

Another example of available data includes the data stored within the knowledge cloud 106. For example, the available data includes the service provider data 202 (FIG. 2), the facility data 204, the microsurvey data 206, the common sense data 208, the domain data 210, the evidence-based guidelines 212, the curated advice 214, and the subject matter ontology data 216. Additionally data stored within the knowledge cloud 106 includes data generated by the cognitive intelligence platform 102, itself.

Follow up questions presented to the user (the second set of follow-up questions) are asked using natural language and are specifically formulated ("dynamically formulated question") to elicit a response that will inform or fulfill an identified parameter. Each dynamically formulated question can target one parameter at a time. When answers are received from the user in response to a dynamically formulated question, the cognitive intelligence platform 102 inserts the answer into the workspace. In some embodiments, each of the answers received from the user and in response to a dynamically formulated question, is stored in a list of facts. Thus the list of facts include information specifically received from the user, and the list of facts is referred to herein as the second data.

With regards to the second set of follow-up questions (or any set of follow-up questions), the cognitive intelligence platform 102 calculates a relevance index, where the relevance index provides a ranking of the questions in the second set of follow-up questions. The ranking provides values indicative of how relevant a respective follow-up question is to the originating question. To calculate the relevance index, the cognitive intelligence platform 102 can use conversations analysis techniques described in HPS ID20180901-01_method. In some embodiments, the first set or second set of follow up questions is presented to the user in the form of the microsurvey 116.

In this first round of analysis, the cognitive intelligence platform 102 consolidates the first and second data in the workspace and determines if additional parameters need to be identified, or if sufficient information is present in the workspace to answer the originating question. In some embodiments, the cognitive agent 110 (FIG. 1) assesses the data in the workspace and queries the cognitive agent 110 to determine if the cognitive agent 110 needs more data in order to answer the originating question. The conversation orchestrator 124 executes as an interface For a complex originating question, the cognitive intelligence platform 102 can go through several rounds of analysis. For example, in a first round of analysis the cognitive intelligence platform 102 parses the originating question. In a subsequent round of analysis, the cognitive intelligence platform 102 can create a sub question, which is subsequently parsed into parameters in the subsequent round of analysis. The cognitive intelligence platform 102 is smart enough to figure out when all information is present to answer an originating question without explicitly programming or pre-programming the sequence of parameters that need to be asked about.

In some embodiments, the cognitive agent 110 is configured to process two or more conflicting pieces of information or streams of logic. That is, the cognitive agent 110, for a given originating question can create a first chain of logic and a second chain of logic that leads to different answers. The cognitive agent 110 has the capability to assess each chain of logic and provide only one answer. That is, the cognitive agent 110 has the ability to process conflicting information received during a round of analysis.

Additionally, at any given time, the cognitive agent 110 has the ability to share its reasoning (chain of logic) to the user. If the user does not agree with an aspect of the reasoning, the user can provide that feedback which results in affecting change in a way the critical thinking engine 108 analyzed future questions and problems.

Subsequent to determining enough information is present in the workspace to answer the originating question, the cognitive agent 110 answers the question, and additionally can suggest a recommendation or a recommendation (e.g., line 418). The cognitive agent 110 suggests the reference or the recommendation based on the context and questions being discussed in the conversation (e.g., conversation 400). The reference or recommendation serves as additional handout material to the user and is provided for informational purposes. The reference or recommendation often educates the user about the overall topic related to the originating question.

In the example illustrated in FIG. 4, in response to receiving the originating questions (line 402), the cognitive intelligence platform 102 (e.g., the cognitive agent 110 in conjunction with the critical thinking engine 108) parses the originating question to determine at least one parameter: location. The cognitive intelligence platform 102 categorizes this parameter, and a corresponding dynamically formulated question in the second set of follow-up questions. Accordingly, in lines 404 and 406, the cognitive agent 110 responds by notifying the user "I can certainly check this . . . " and asking the dynamically formulated question "I need some additional information in order to answer this question, was this an in-home glucose test or was it done by a lab or testing service?"

The user 401 enters his answer in line 408: "It was an in-home test," which the cognitive agent 110 further analyzes to determine additional parameters: e.g., a digestive state, where the additional parameter and a corresponding dynamically formulated question as an additional second set of follow-up questions. Accordingly, the cognitive agent 110 poses the additional dynamically formulated question in lines 410 and 412: "One other question . . . " and "How long before you took that in-home glucose test did you have a meal?" The user provides additional information in response "it was about an hour" (line 414).

The cognitive agent 110 consolidates all the received responses using the critical thinking engine 108 and the knowledge cloud 106 and determines an answer to the initial question posed in line 402 and proceeds to follow up with a final question to verify the user's initial question was answered. For example, in line 416, the cognitive agent 110 responds: "It looks like the results of your test are at the upper end of the normal range of values for a glucose test given that you had a meal around an hour before the test." The cognitive agent 110 provides additional information (e.g., provided as a link): "Here is something you could refer," (line 418), and follows up with a question "Did that answer your question?" (line 420).

As described above, due to the natural language database 108, in various embodiments, the cognitive agent 110 is able to analyze and respond to questions and statements made by a user 401 in natural language. That is, the user 401 is not restricted to using certain phrases in order for the cognitive agent 110 to understand what a user 401 is saying. Any phrasing, similar to how the user would speak naturally can be input by the user and the cognitive agent 110 has the ability to understand the user.

Figure 5:
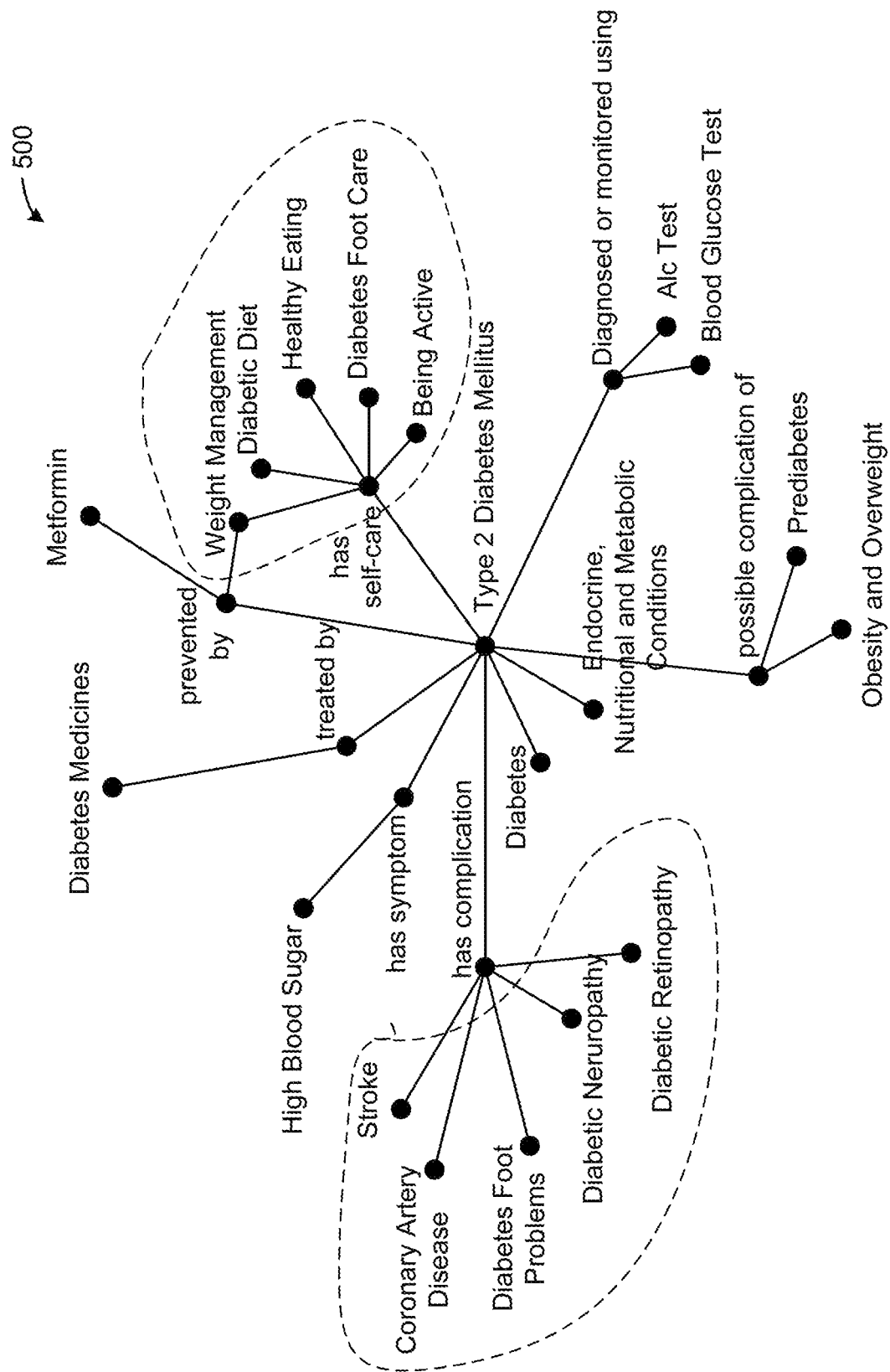
FIG. 5 shows a cognitive map or "knowledge graph", in accordance with various embodiments.

FIG. 5 illustrates a cognitive map or "knowledge graph" 500, in accordance with various embodiments. In particular, the knowledge graph represents a graph traversed by the cognitive intelligence platform 102, when assessing questions from a user with Type 2 diabetes. Individual nodes in the knowledge graph 500 represent a health artifact (health related information) or relationship (predicate) that is gleaned from direct interrogation or indirect interactions with the user (by way of the user device 104).

In one embodiment, the cognitive intelligence platform 102 identified parameters for an originating question based on a knowledge graph illustrated in FIG. 5. For example, the cognitive intelligence platform 102 parses the originating question to determine which parameters are present for the originating question. In some embodiments, the cognitive intelligence platform 102 infers the logical structure of the parameters by traversing the knowledge graph 500, and additionally, knowing the logical structure enables the cognitive agent 110 to formulate an explanation as to why the cognitive agent 110 is asking a particular dynamically formulated question.

In some embodiments, the individual elements or nodes are generated by the artificial intelligence engine based on input data (e.g., evidence-based guidelines, patient notes, clinical trials, physician research or the like). The artificial intelligence engine may parse the input data and construct the relationships between the health artifacts.

For example, a root node may be associated with a first health related information "Type 2 Diabetes Mellitus", which is a name of a medical condition. In some embodiments, the root node may also be associated with a definition of the medical condition. An example predicate, "has symptom", is represented by an individual node connected to the root node, and another health related information, "High Blood Sugar", is represented by an individual node connected to the individual node representing the predicate. A logical structure may be represented by these three nodes, and the logical structure may indicate that "Type 2 Diabetes Mellitus has symptom High Blood Sugar".

In some embodiments, the health related information may correspond to known facts, concepts, and/or any suitable health related information that are discovered or provided by a trusted source (e.g., a physician having a medical license and/or a certified/accredited healthcare organization), such as evidence-based guidelines, clinical trials, physician research, patient notes entered by physicians, and the like. The predicates may be part of a logical structure (e.g., sentence) such as a form of subject-predicate-direct object, subject-predicate-indirect object-direct object, subject-predicate-subject complement, or any suitable simple, compound, complex, and/or compound/complex logical structure. The subject may be a person, place, thing, health artifact, etc. The predicate may express an action or being within the logical structure and may be a verb, modifying words, phrases, and/or clauses. For example, one logical structure may be the subject-predicate-direct object form, such as "A has B" (where A is the subject and may be a noun or a health artifact, "has" is the predicate, and B is the direct object and may be a health artifact).

The various logical structures in the depicted knowledge graph may include the following: "Type 2 Diabetes Mellitus has symptom High Blood Sugar"; "Type 2 Diabetes Mellitus has complication Stroke"; "Type 2 Diabetes Mellitus has complication Coronary Artery Disease"; "Type 2 Diabetes Mellitus has complication Diabetes Foot Problems"; "Type 2 Diabetes Mellitus has complication Diabetic Neuropathy"; "Type 2 Diabetes Mellitus has complication Diabetic Retinopathy"; "Type 2 Diabetes Mellitus diagnosed or monitored using Blood Glucose Test"; just to name a few examples. It should be understood that there are other logical structures and represented in the knowledge graph 500.

In some embodiments, the information depicted in the knowledge graph may be represented as a matrix. The health artifacts may be represented as quantities and the predicates may be represented as expressions in a rectangular array in rows and columns of the matrix. The matrix may be treated as a single entity and manipulated according to particular rules.

The knowledge graph 500 or the matrix may be generated for each known medical condition and stored by the cognitive intelligence platform 102. The knowledge graphs and/or matrices may be updated continuously or on a periodic basis using subject data pertaining to the medical conditions received from the trusted sources. For example, additional clinical trials may lead to new discoveries about particular medical condition treatments, which may be used to update the knowledge graphs and/or matrices.

The knowledge graph 500 including the logical structures may be used to transform unstructured data (patient notes in an EMR entered by a physician) into cognified data. The cognified data may be used to generate a diagnosis of the patient. Also, the cognified data may be used to determine which information pertaining to the medical condition to provide to the patient and when to provide the information to the patient to improve the user experience using the computing device. The disclosed techniques may also save computing resources by providing the cognified data to the physician to review, improve diagnosis accuracy, and/or regulate the amount of information provided to the patient.

Figure 6:
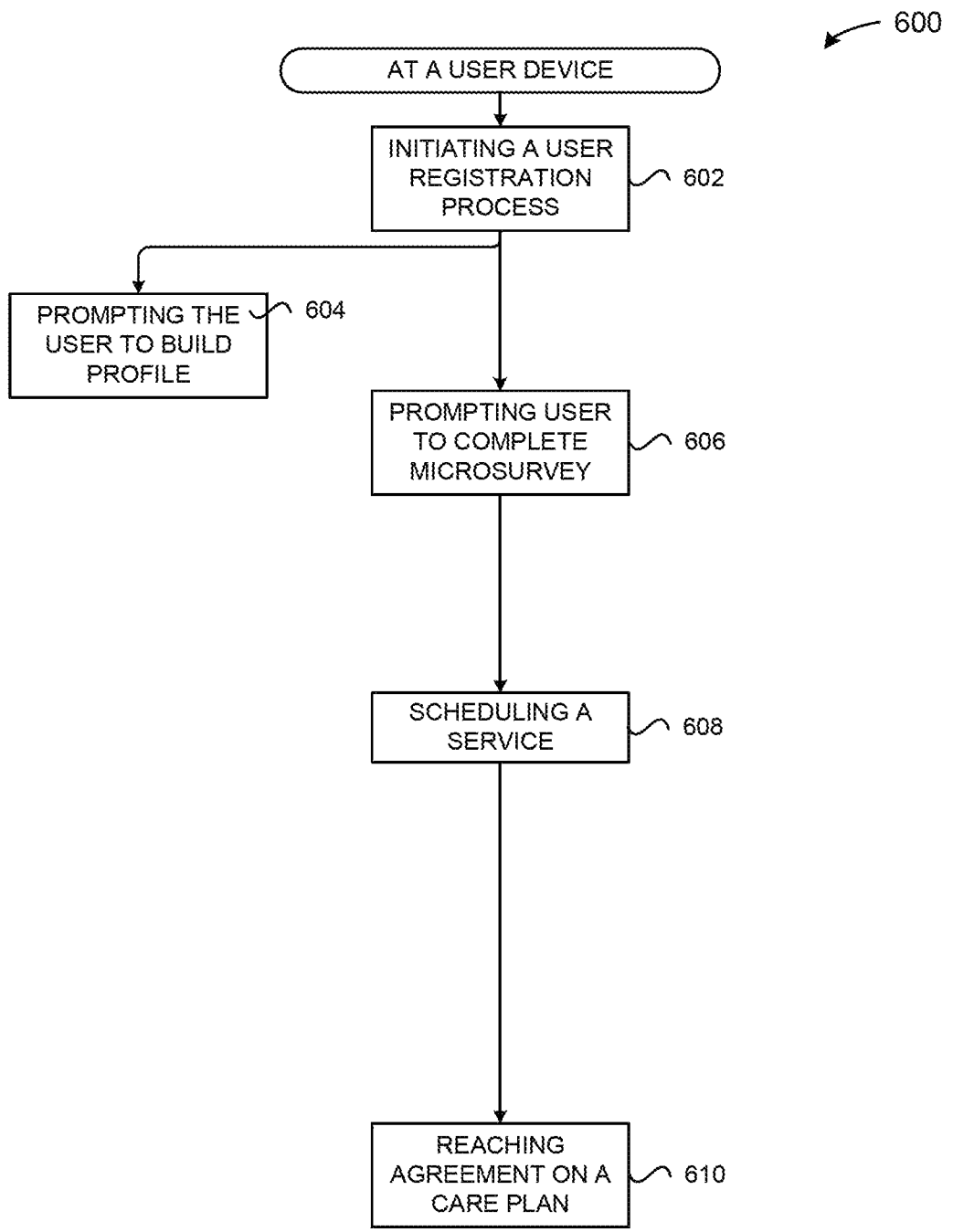
FIG. 6 shows a method, in accordance with various embodiments.

FIG. 6 shows a method, in accordance with various embodiments. The method is performed at a user device (e.g., the user device 102) and in particular, the method is performed by an application executing on the user device 102. The method begins with initiating a user registration process (block 602). The user registration can include tasks such as displaying a GUI asking the user to enter in personal information such as his name and contact information.

Next, the method includes prompting the user to build his profile (block 604). In various embodiments, building his profile includes displaying a GUI asking the user to enter in additional information, such as age, weight, height, and health concerns. In various embodiments, the steps of building a user profile is progressive, where building the user profile takes place over time. In some embodiments, the process of building the user profile is presented as a game. Where a user is presented with a ladder approach to create a "star profile". Aspects of a graphical user interface presented during the profile building step are additionally discussed in FIGS. 8A-8B.

The method contemplates the build profile (block 604) method step is optional. For example, the user may complete building his profile at this method step 604, the user may complete his profile at a later time, or the cognitive intelligence platform 102 builds the user profile over time as more data about the user is received and processed. For example, the user is prompted to build his profile, however, the user fails to enter in information or skips the step. The method proceeds to prompting a user to complete a microsurvey (block 606). In some embodiments, the cognitive agent 110 uses answers received in response to the microsurvey to build the profile of the user. Overall, the data collected through the user registration process is stored and used later as available data to inform answers to missing parameters.

Next, the cognitive agent 110 proceeds to scheduling a service (block 608). The service can be scheduled such that it aligns with a health plan of the user or a protocol that results in a therapeutic goal. Next, the cognitive agent 110 proceeds to reaching agreement on a care plan (block 610).

Figure 7A:
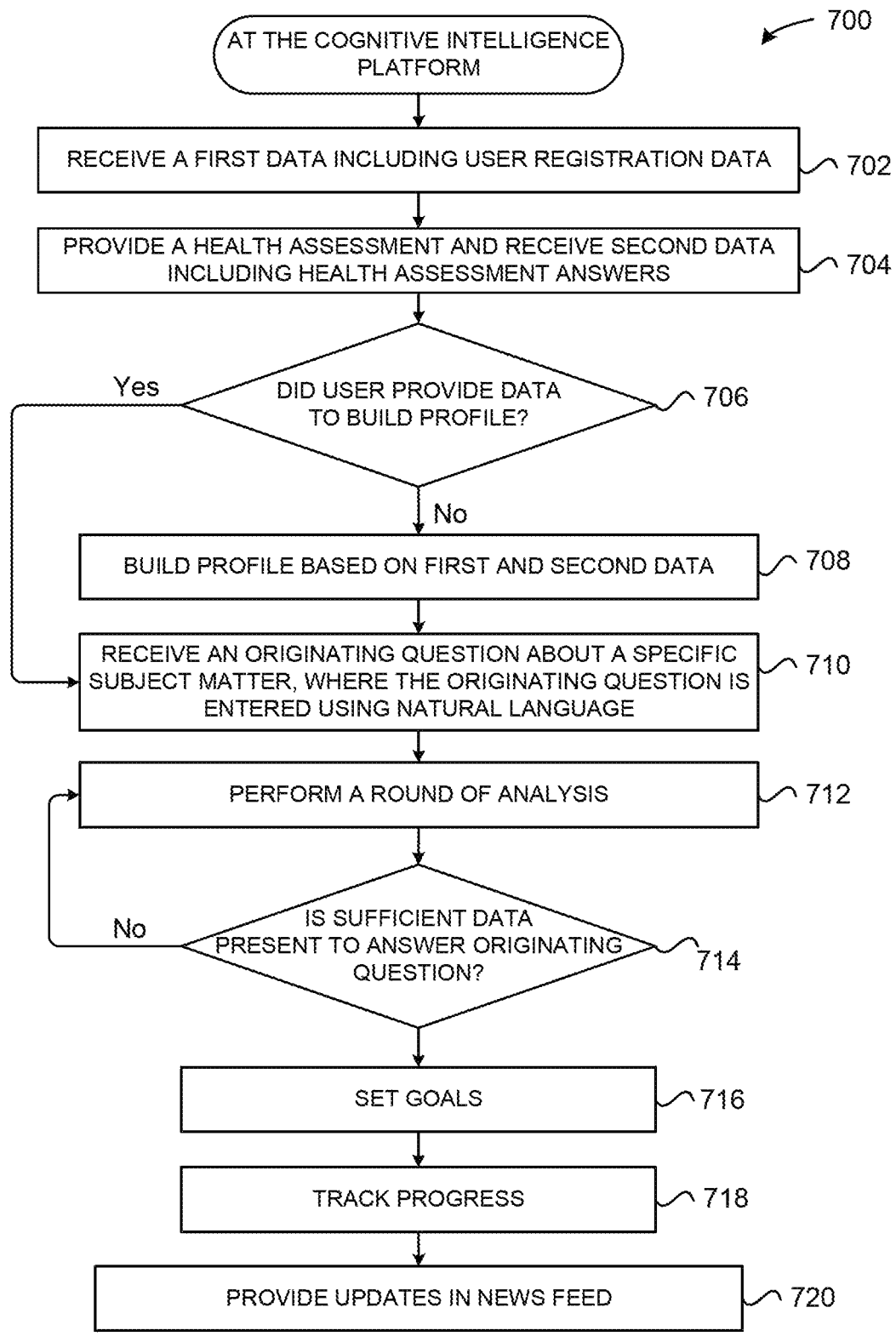
FIGS. 7A, 7B, and 7C show methods, in accordance with various embodiments.
Figure 7B:
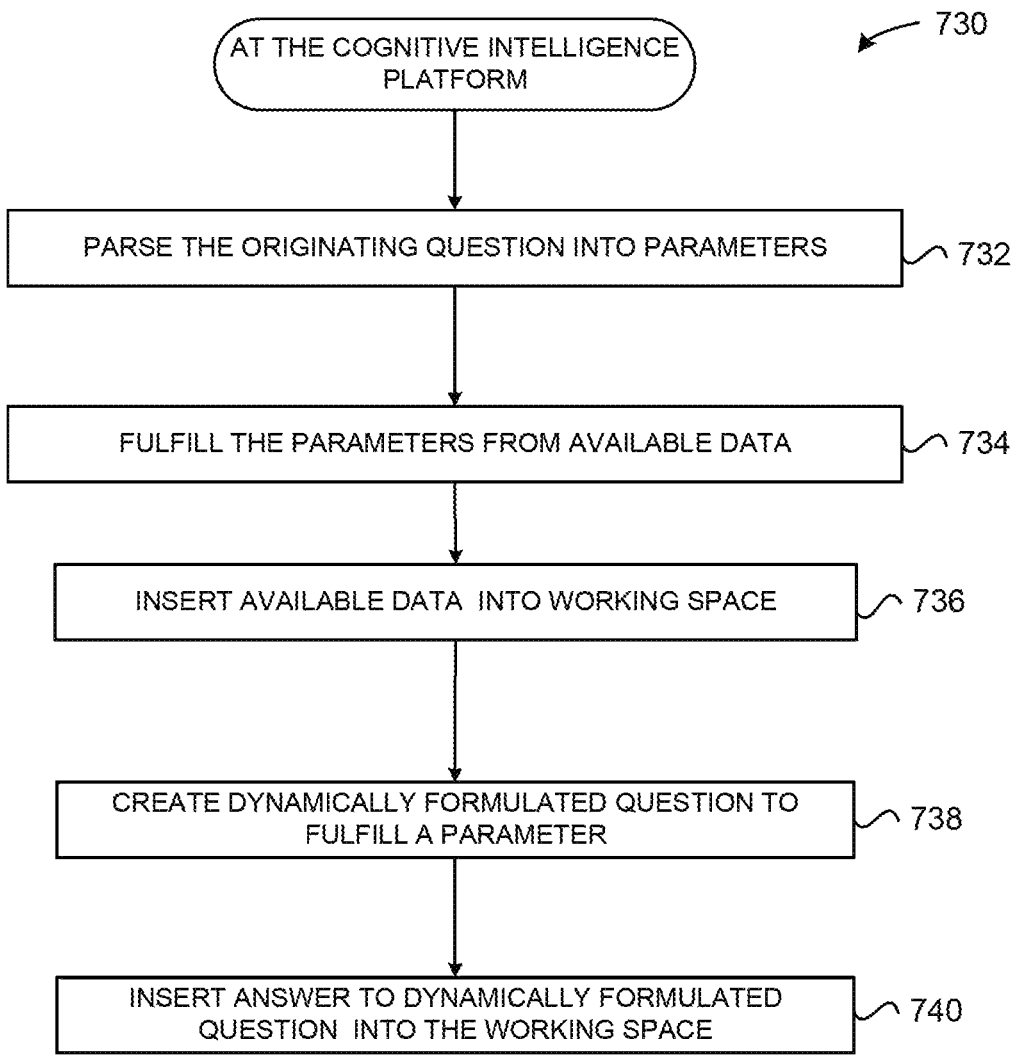
Figure 7C:
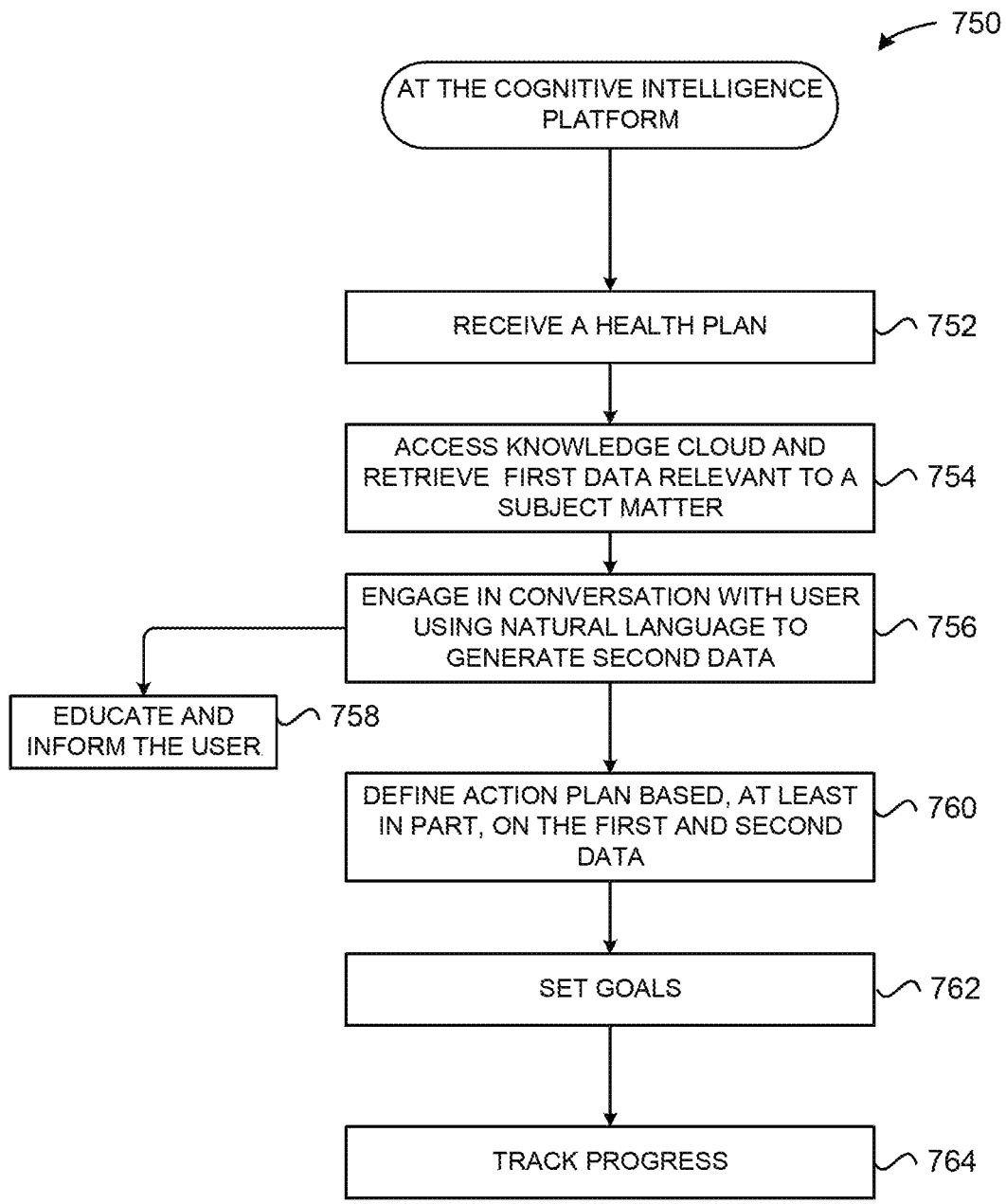

FIGS. 7A, 7B, and 7C, show methods, in accordance with various embodiments. The methods are performed at the cognitive intelligence platform. In particular, in FIG. 7A, the method begins with receiving a first data including user registration data (block 702); and providing a health assessment and receiving second data including health assessment answers (block 704). In various embodiments, the health assessment is a micro-survey with dynamically formulated questions presented to the user.

Next the method determine if the user provided data to build a profile (decision block 706). If the user did not provide data to build the profile, the method proceeds to building profile based on first and second data (block 708). If the user provided data to build the profile, the method proceeds to block 710.

At block 710, the method 700 proceeds to receiving an originating question about a specific subject matter, where the originating question is entered using natural language, and next the method proceeds to performing a round of analysis (block 712). Next, the method determines if sufficient data is present to answer originating questions (decision block 714). If no, the method proceeds to block 712 and the method performs another round of analysis. If yes, the method proceeds to setting goals (block 716), then tracking progress (block 718), and then providing updates in a news feed (block 720).

In FIG. 7B, a method 730 of performing a round of analysis is illustrated. The method begins with parsing the originating question into parameters (block 732); fulfilling the parameters from available data (block 734); inserting available data (first data) into a working space (block 736); creating a dynamically formulated question to fulfill a parameter (block 738); and inserting an answer to the dynamically formulated question into the working space (block 740).

In FIG. 7C, a method 750 is performed at the cognitive intelligence platform. The method begins with receiving a health plan (block 752); accessing the knowledge cloud and retrieving first data relevant to the subject matter (block 754); and engaging in conversation with the user using natural language to general second data (block 756). In various embodiments, the second data can include information such as a user's scheduling preferences, lifestyle choices, and education level. During the process of engaging in conversation, the method includes educating and informing the user (block 758). Next, the method includes defining an action plan based, at least in part, on the first and second data (block 760); setting goals (block 762); and tracking progress (block 764).

FIGS. 8A, 8B, 8C, and 8D illustrate aspects of interactions between a user and the cognitive intelligence platform 102, in accordance with various embodiments. As a user interacts with the GUI, the cognitive intelligence platform 102 continues to build a database of knowledge about the user based on questions asked by the user as well as answers provided by the user (e.g., available data as described in FIG. 4). In particular, FIG. 8A displays a particular screen shot 801 of the user device 104 at a particular instance in time. The screen shot 801 displays a graphical user interface (GUI) with menu items associated with a user's (e.g., Nathan) profile including Messages from the doctor (element 804), Goals (element 806), Trackers (element 808), Health Record (element 810), and Health Plans & Assessments (element 812). The menu item Health Plans & Assessments (element 812), additionally include child menu items: Health Assessments (element 812*a*), Health plans (812*b*).

The screen shot 803 displays the same GUI as in the screen shot 801, however, the user has scrolled down the menu, such that additional menu items below Health Plans & Assessments (element 812) are shown. The additional menu items include Reports (element 814), Health Team (element 816), and Purchases and Services (Element 818). Furthermore, additional menu items include Add your Health Team (element 820) and Read about improving your A1C levels (element 822).

Figure 8A:
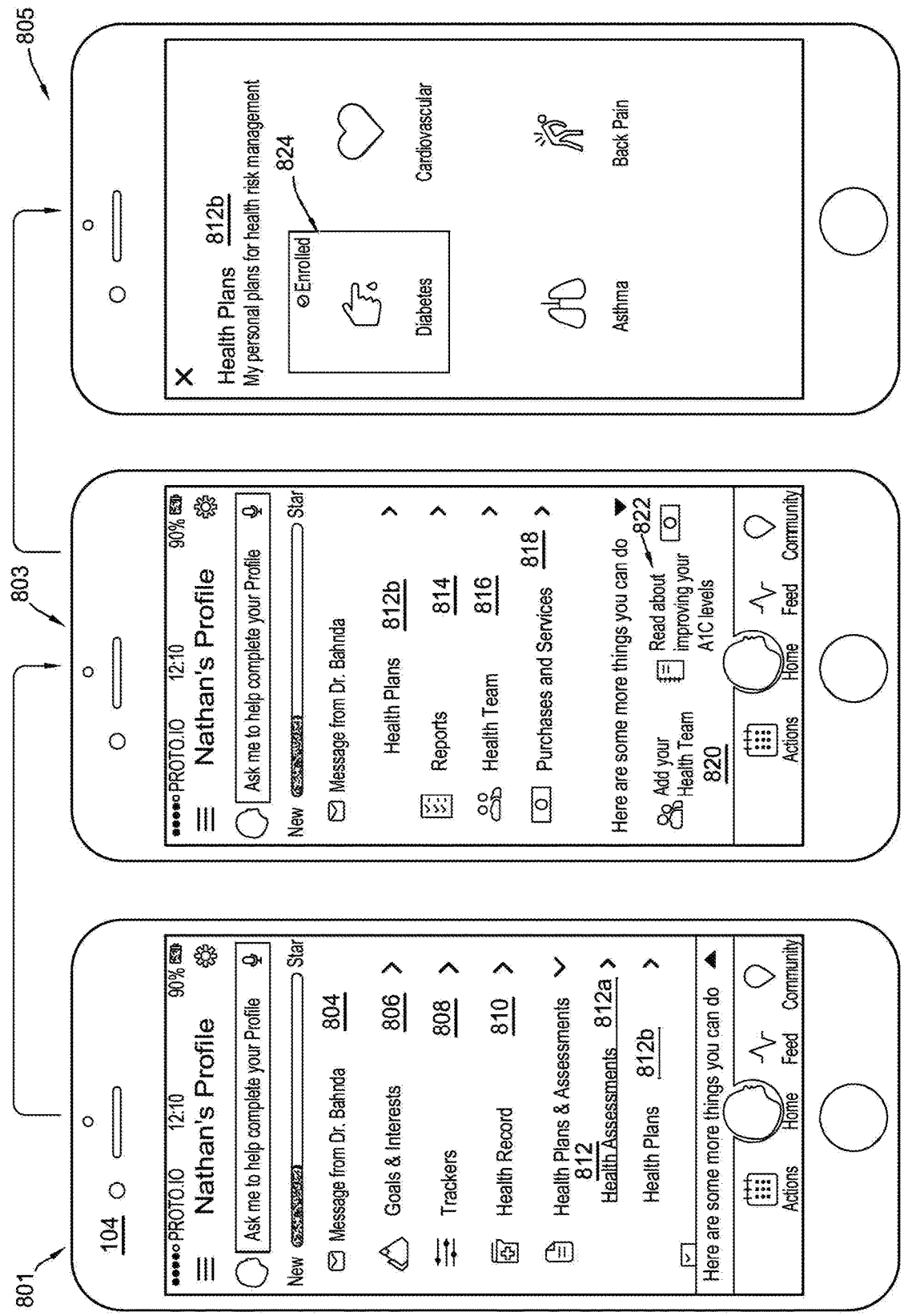
FIGS. 8A, 8B, 8C, and 8D show aspects of a user interface, in accordance with various embodiments.

For purposes of the example in FIG. 8A, the user selects the menu item Health Plans (element 812*b*). Accordingly, in response to the receiving the selection of the menu item Health Plans, types of health plans are shown, as illustrated in screen shot 805. The types of health plans shown with respect to Nathan's profile include: Diabetes (element 824), Cardiovascular, Asthma, and Back Pain. Each type of health plan leads to separate displays. For purposes of this example in FIG. 8A, the user selects the Diabetes (element 824) health plan.

Figure 8B:
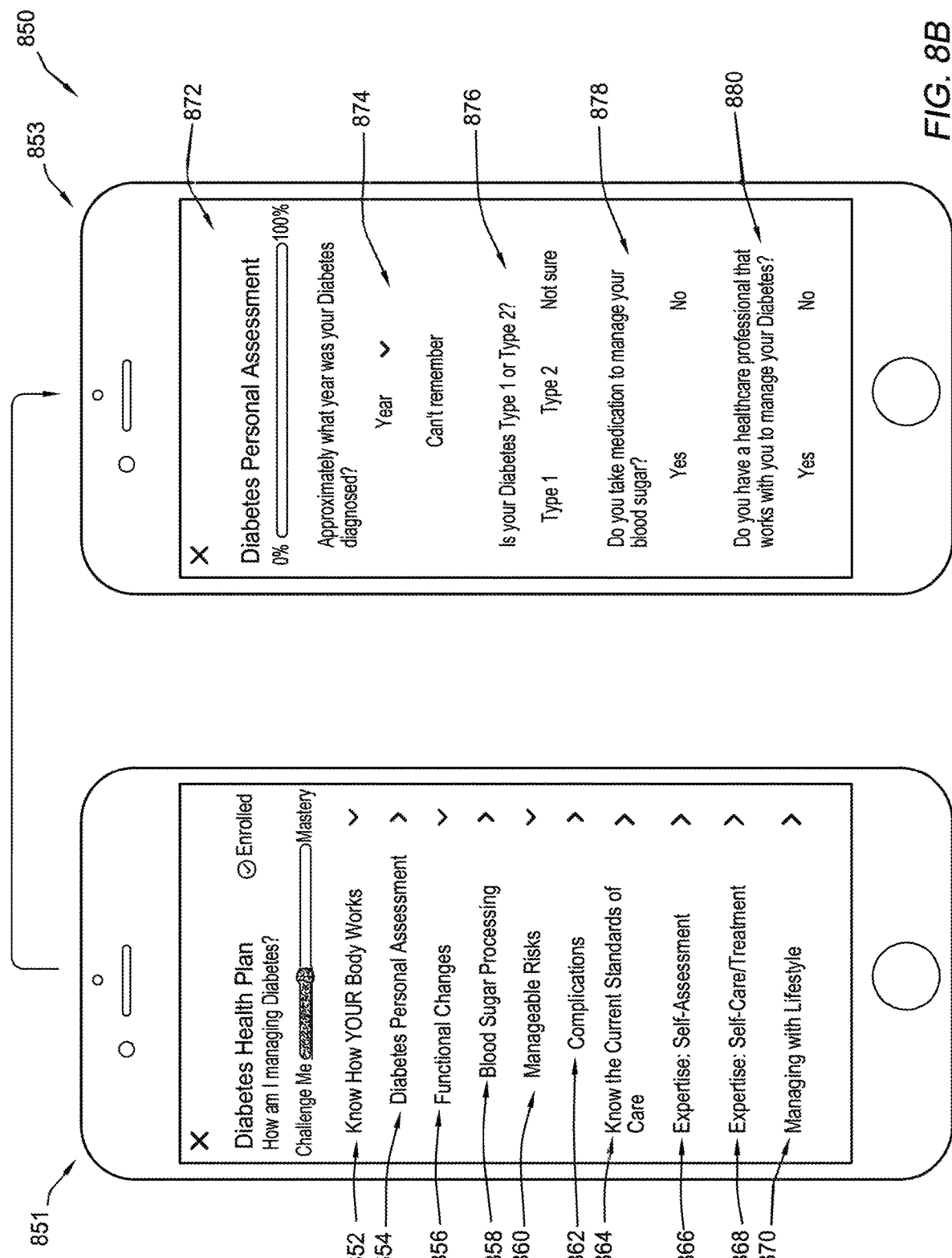

In FIG. 8B, the screenshot 851 is seen in response to the user's selection of Diabetes (element 824). Example elements displayed in screenshot 851 include: Know How YOUR Body Works (element 852); Know the Current Standards of Care (element 864); Expertise: Self-Assessment (element 866); Expertise: Self-Care/Treatment (element 868); and Managing with Lifestyle (element 870). Managing with Lifestyle (element 870) focuses and tracks actions and lifestyle actions that a user can engage in. As a user's daily routine helps to manage diabetes, managing the user's lifestyle is important. The cognitive agent 110 can align a user's respective health plan based on a health assessment at enrollment. In various embodiments, the cognitive agent 110 aligns the respective health plan with an interest of the user, a goal and priority of the user, and lifestyle factors of the user—including exercise, diet and nutrition, and stress reduction.

Each of these elements 852, 864, 866, 868, and 870 can display additional sub-elements depending on a selection of the user. For example, as shown in the screen shot 851, Know How YOUR Body Works (element 852) includes additional sub-elements: Diabetes Personal Assessment (854); and Functional Changes (856). Additional sub-elements under Functional Changes (856) include: Blood Sugar Processing (858) and Manageable Risks (860). Finally, the sub-element Manageable Risks (860) includes an additional sub-element Complications (862). For purposes of this example, the user selects the Diabetes Personal Assessment (854) and the screen shot 853 shows a GUI (872) associated with the Diabetes Personal Assessment.

The Diabetes Personal Assessment includes questions such as "Approximately what year was your Diabetes diagnosed" and corresponding elements a user can select to answer including "Year" and "Can't remember" (element 874). Additional questions include "Is your Diabetes Type 1 or Type 2" and corresponding answers selectable by a user include "Type 1," "Type 2," and "Not sure" (element 876). Another question includes "Do you take medication to manage your blood sugar" and corresponding answers selectable by a user include "Yes" and "No" (element 878). An additional question asks "Do you have a healthcare professional that works with you to manage your Diabetes" and corresponding answers selectable by the user include "Yes" and "No" (element 880).

In various embodiments, the cognitive intelligence platform 102 collects information about the user based on responses provided by the user or questions asked by the user as the user interacts with the GUI. For example, as the user views the screen shot 851, if the user asks if diabetes is curable, this question provides information about the user such as a level of education of the user.

Figure 8C:
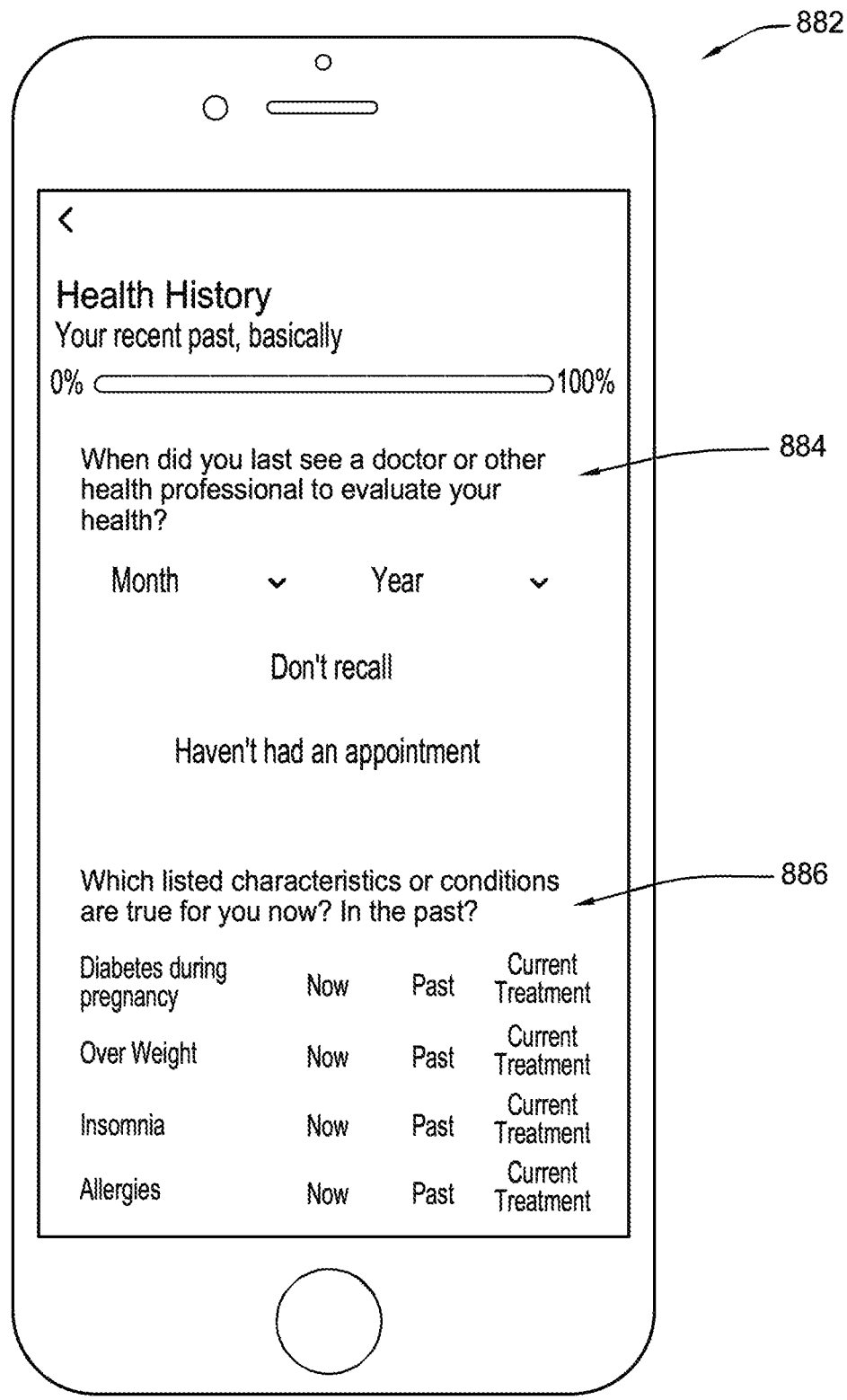

FIG. 8C illustrates aspects of an additional tool—e.g., a microsurvey—provided to the user that helps gather additional information about the user (e.g., available data). In various embodiments, a micro-survey represent a short targeted survey, where the questions presented in the survey are limited to a respective micro-theory. A microsurvey can be created by the cognitive intelligence platform 102 for several different purposes, including: completing a user profile, and informing a missing parameter during the process of answering an originating question.

In FIG. 8C, the microsurvey 882 gathers information related to health history, such as "when did you last see a doctor or other health professional to evaluate your health" where corresponding answers selectable by the user include specifying a month and year, "don't recall," and "haven't had an appointment" (element 884). An additional question asks "Which listed characteristics or conditions are true for you now? In the past?" where corresponding answers selectable by the user include "Diabetes during pregnancy," "Over Weight," "Insomnia," and "Allergies" (element 886). Each of the corresponding answer in element 886 also includes the option to indicate whether the characteristics or conditions are true for the user "Now", "Past," or "Current Treatment."

Figure 8D:
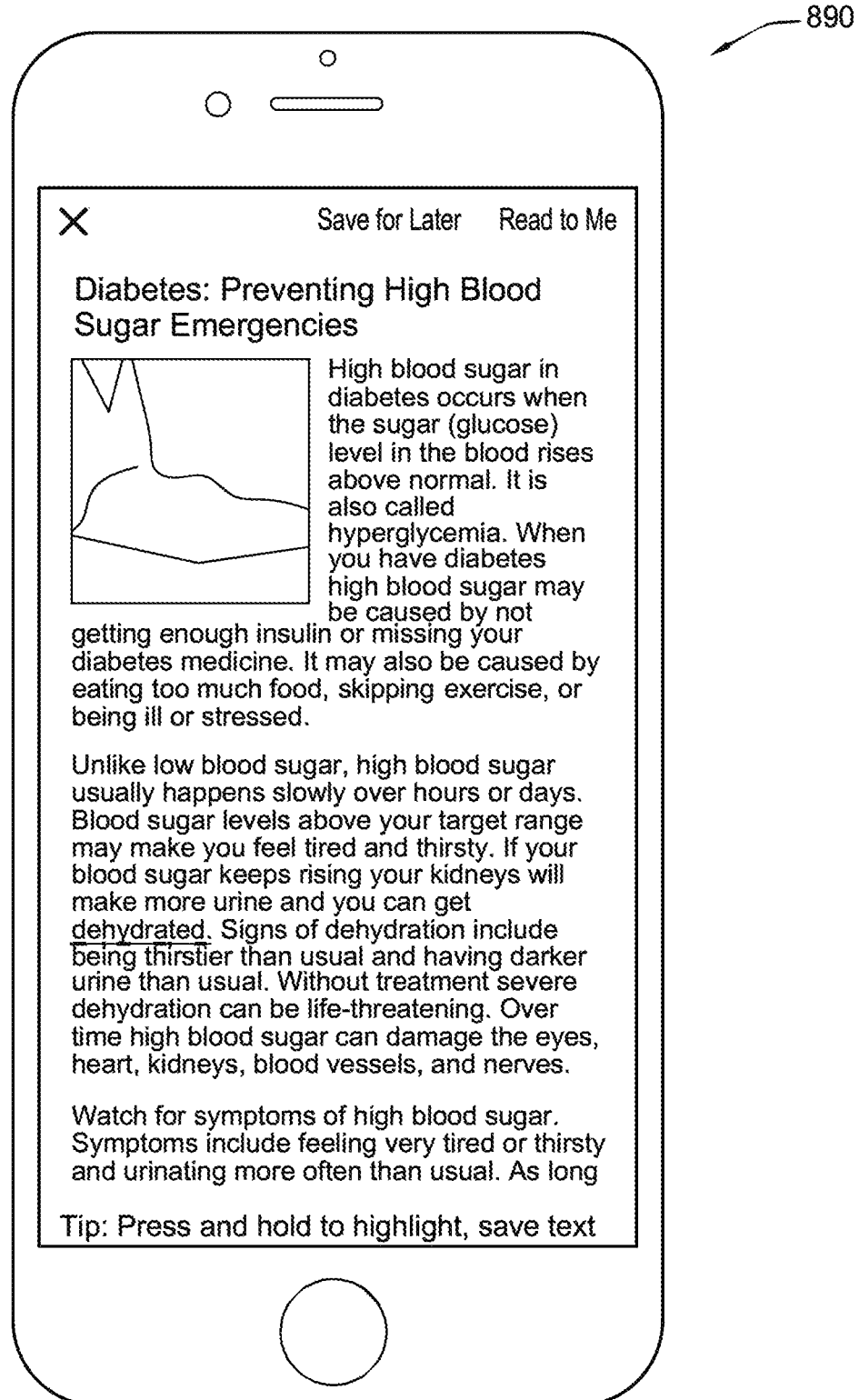

In FIG. 8D, aspects of educating a user are shown in the screen shot 890. The screen shot displays an article titled "Diabetes: Preventing High Blood Sugar Emergencies," and proceeds to describe when high blood sugar occurs and other information related to high blood sugar. The content displayed in the screen shot 890 is searchable and hearable as a podcast.

Accordingly, the cognitive agent 110 can answer a library of questions and provide content for many questions a user has as it related to diabetes. The information provided for purposes of educating a user is based on an overall health plan of the user, which is based on meta data analysis of interactions with the user, and an analysis of the education level of the user.

Figure 9A:
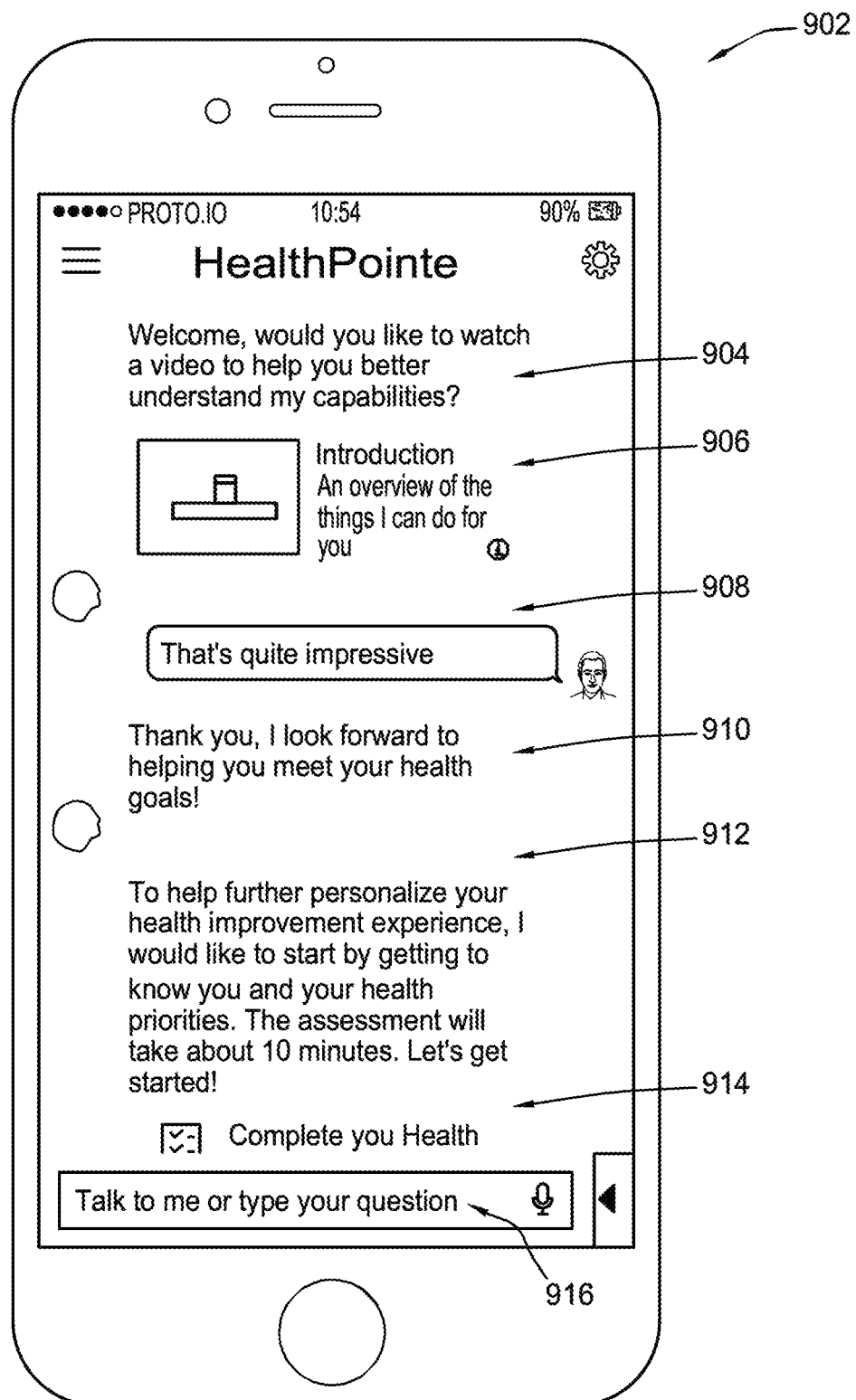
FIGS. 9A and 9B shows aspects of a conversational stream, in accordance with various embodiments.
Figure 9B:
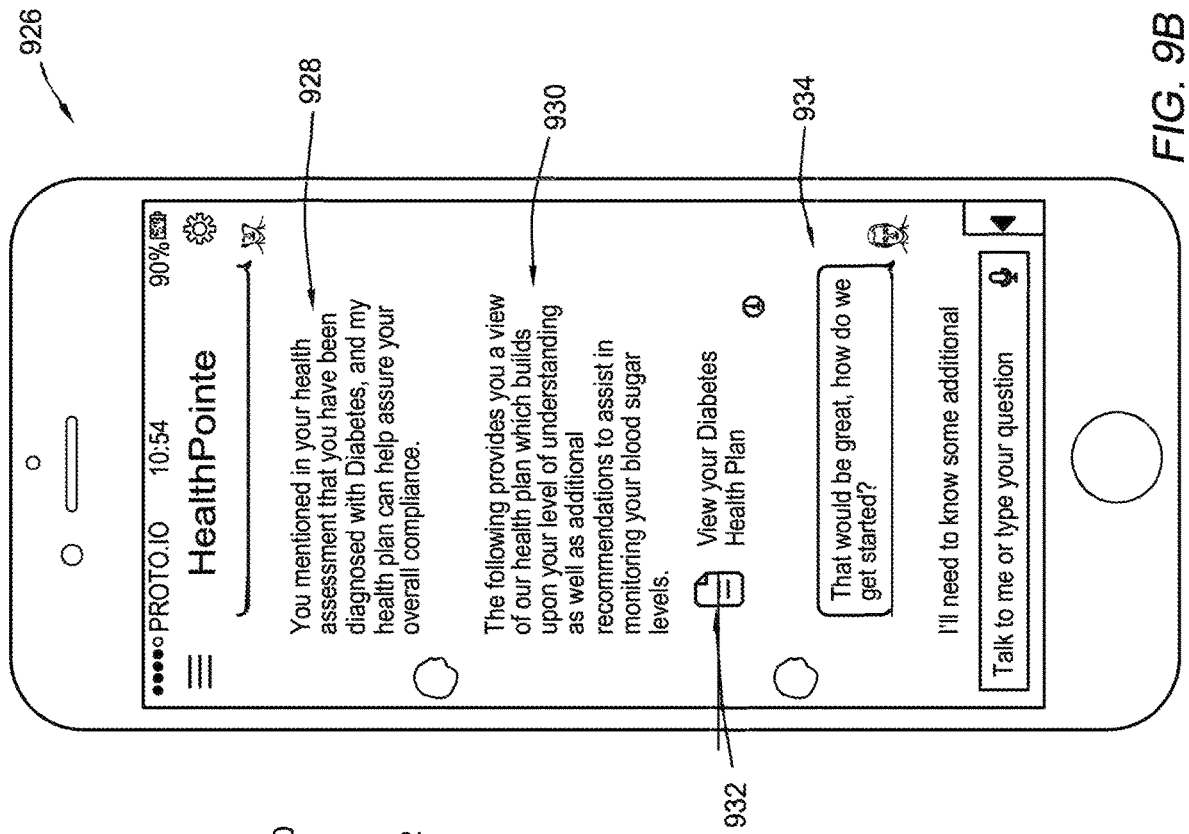
Figure 9B:
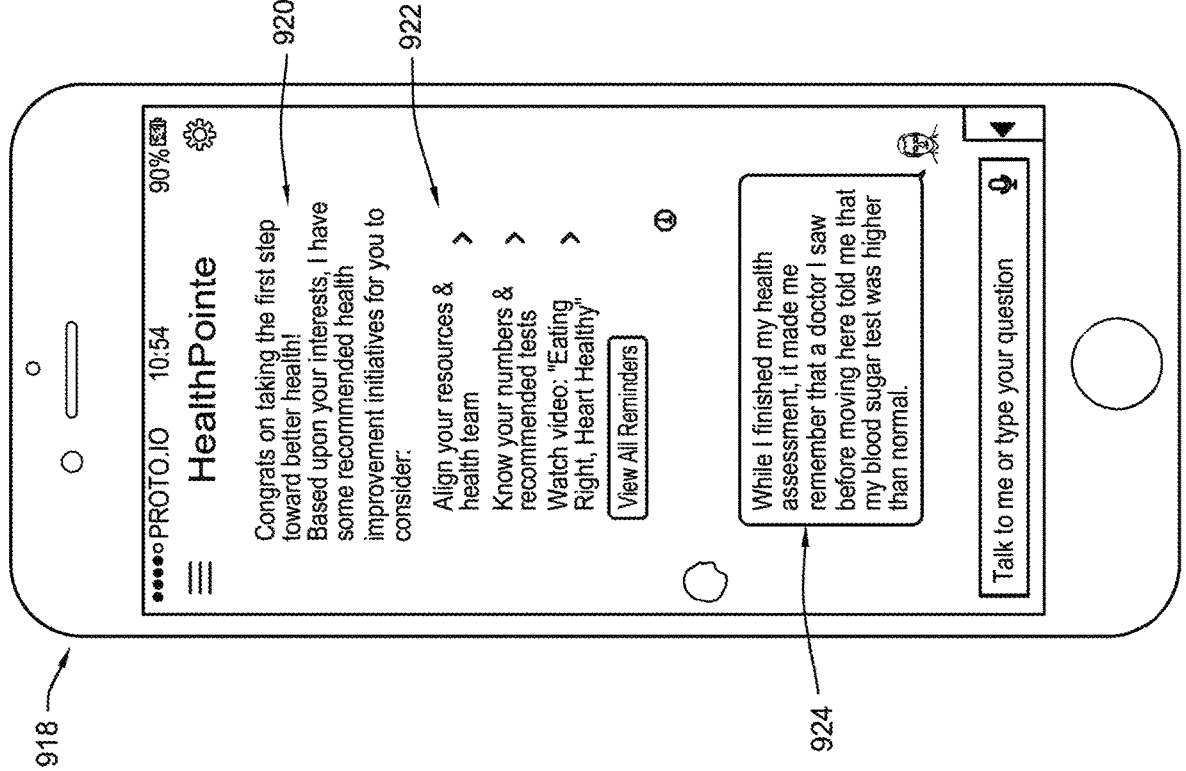

FIGS. 9A-9B illustrate aspects of a conversational stream, in accordance with various embodiments. In particular, FIG. 9A displays an example conversational stream between a user and the cognitive agent 110. The screen shot 902 is an example of a dialogue that unfolds between a user and the cognitive agent 110, after the user has registered with the cognitive intelligence platform 102. In the screen shot 902, the cognitive agent 110 begins by stating "Welcome, would you like to watch a video to help you better understand my capabilities" (element 904). The cognitive agent provides an option to watch the video (element 906). In response, the user inputs text "that's quite impressive" (element 908). In various embodiments, the user inputs text using the input box 916, which instructs the user to "Talk to me or type your question".

Next, the cognitive agent 110 says "Thank you. I look forward to helping you meet your health goals!" (element 910). At this point, the cognitive agent 110 can probe the user for additional data by offering a health assessment survey (e.g., a microsurvey) (element 914). The cognitive agent 110 prompts the user to fill out the health assessment by stating: "To help further personalize your health improvement experience, I would like to start by getting to know you and your health priorities. The assessment will take about 10 minutes. Let's get started!" (element 912).

In FIG. 9B, an additional conversational stream between the user and the cognitive agent 110 is shown. In this example conversational stream, the user previously completed a health assessment survey. The conversational stream can follow the example conversational stream discussed in FIG. 9A.

In the screen shot 918, the cognitive agent acknowledges the user's completion of the health assessment survey (element 920) and provides additional resources to the user (element 922). In element 920, the cognitive agent states: "Congrats on taking the first step toward better health! Based upon your interest, I have some recommended health improvement initiatives for you to consider," and presents the health improvement initiatives. In the example conversational stream, the user gets curious about a particular aspect of his health and states: "While I finished my health assessment, it made me remember that a doctor I saw before moving here told me that my blood sugar test was higher than normal." (element 924). After receiving the statement in element 924, the cognitive agent 110 treats the statement as an originating question and undergoes an initial round of analysis (and additional rounds of analysis as needed) as described above.

The cognitive agent 110 presents an answer as shown in screen shot 926. For example, the cognitive agent 110 states: "You mentioned in your health assessment that you have been diagnosed with Diabetes, and my health plan can help assure your overall compliance" (element 928). The cognitive agent further adds: "The following provides you a view of our health plan which builds upon your level of understanding as well as additional recommendations to assist in monitoring your blood sugar levels" (element 930). The cognitive agent 110 provides the user with the option to view his Diabetes Health Plan (element 932).

The user responds "That would be great, how do we get started" (element 934). The cognitive agent 110 receives the user's response as another originated question and undergoes an initial round of analysis (and additional rounds of analysis as needed) as described above. In the example screen shot 926, the cognitive agent 110 determines additional information is needed and prompts the user for additional information.

Figure 10:
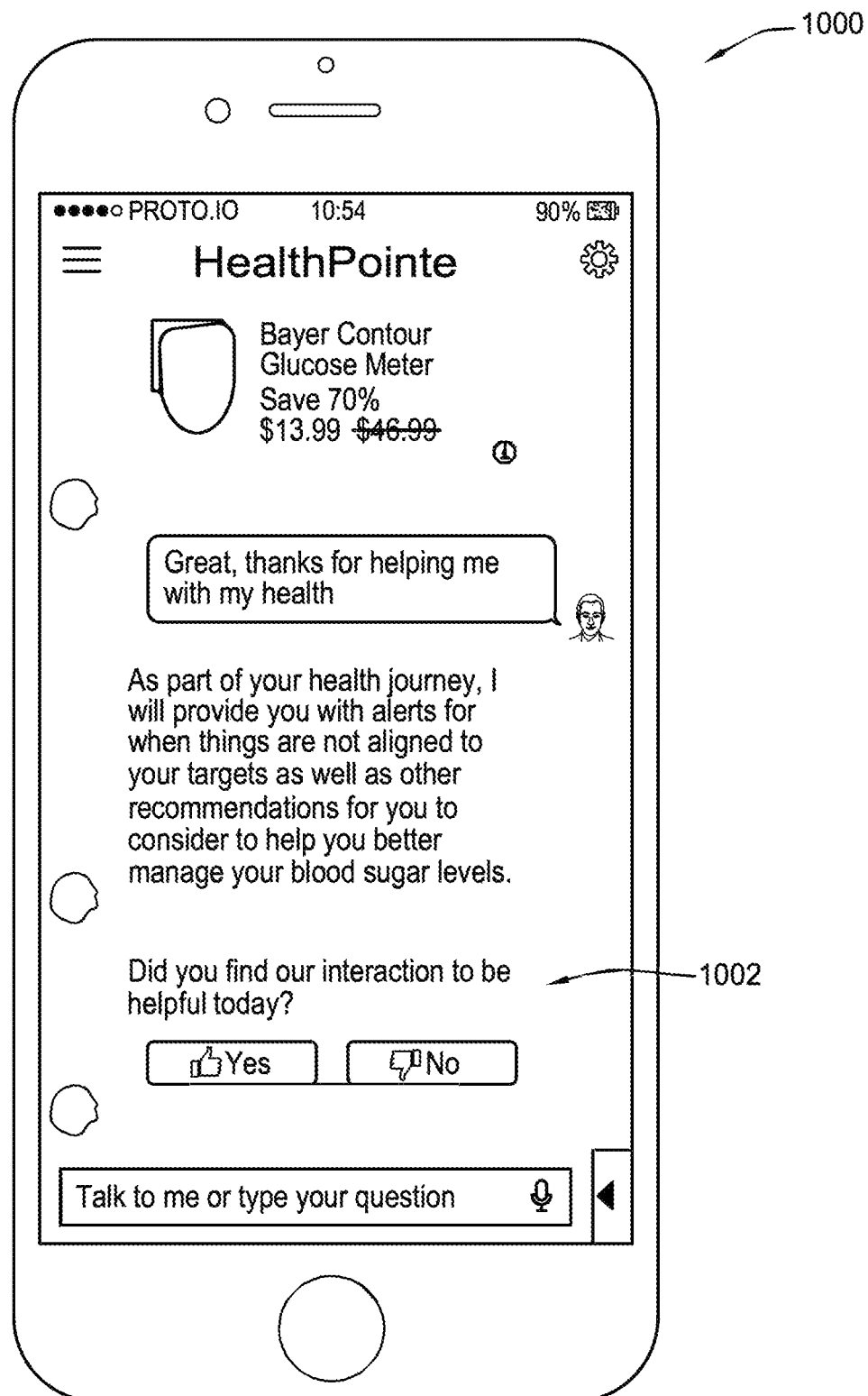
FIG. 10 shows aspects of a conversational stream, in accordance with various embodiments.

FIG. 10 illustrates an additional conversational stream, in accordance with various embodiments. In particular, in the screen shot 1000, the cognitive agent 110 elicit feedback (element 1002) to determine whether the information provided to the user was useful to the user.

Figure 11:
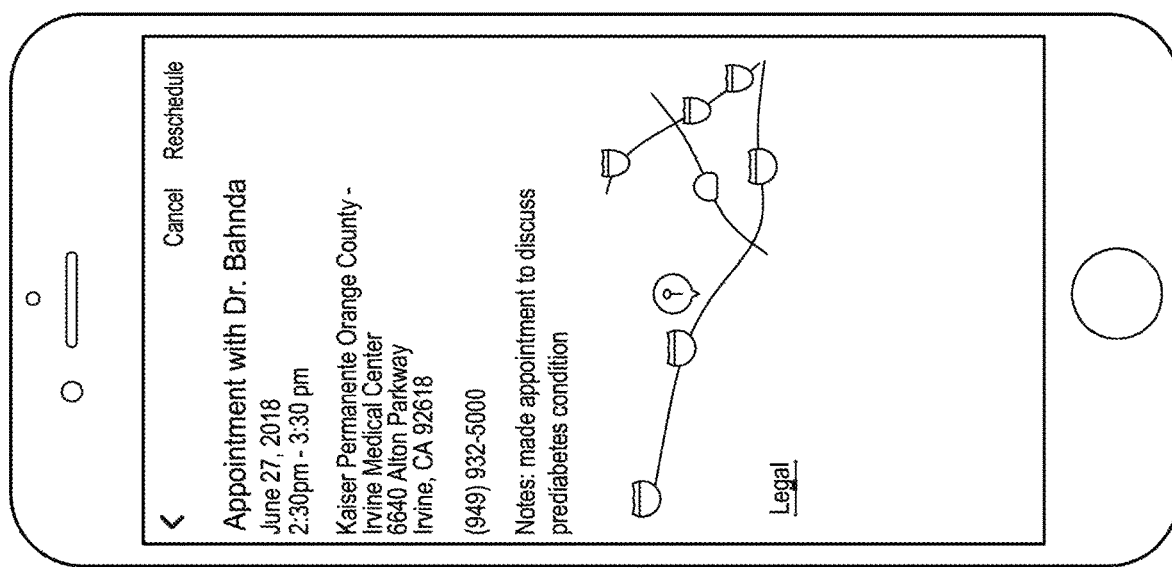
FIG. 11 shows aspects of an action calendar, in accordance with various embodiments.
Figure 11:
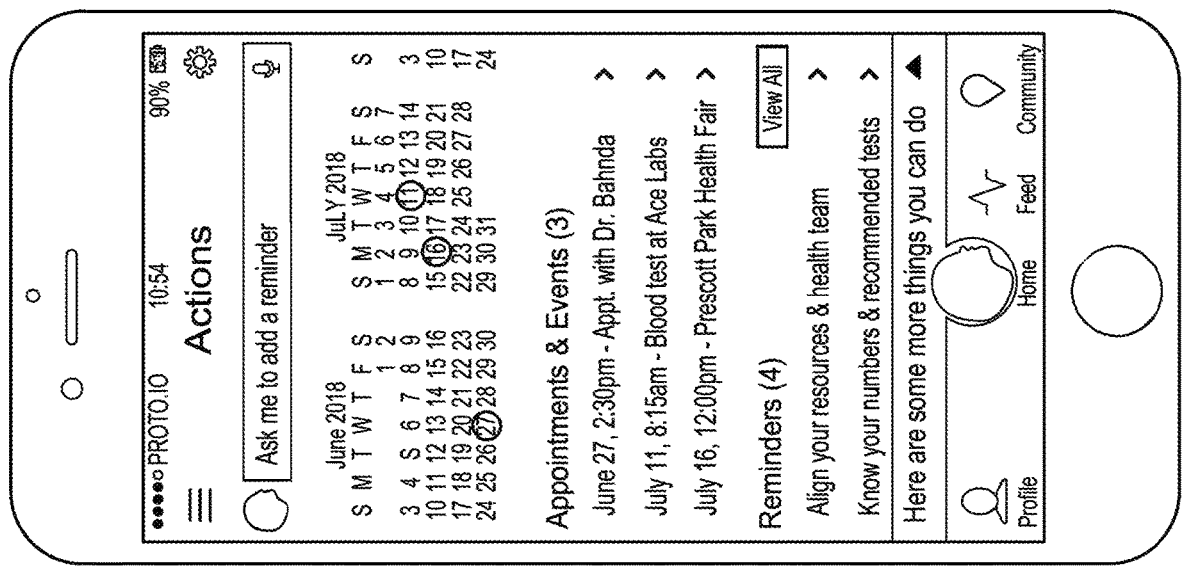

FIG. 11 illustrates aspects of an action calendar, in accordance with various embodiments. The action calendar is managed through the conversational stream between the cognitive agent 110 and the user. The action calendar aligns to care and wellness protocols, which are personalized to the risk condition or wellness needs of the user. The action calendar is also contextually aligned (e.g., what is being required or searched by the user) and hyper local (e.g., aligned to events and services provided in the local community specific to the user).

Figure 12:
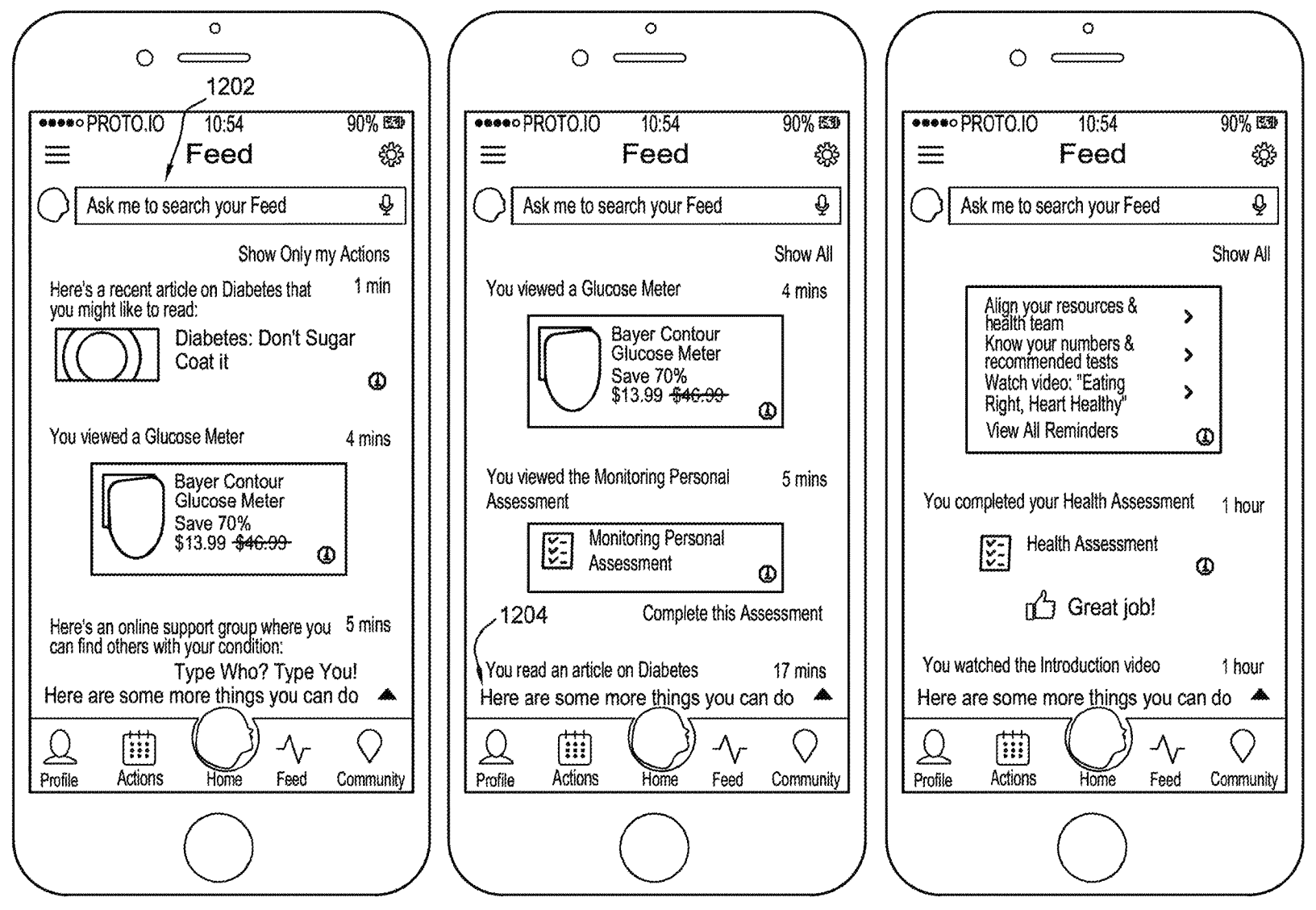

FIG. 12 illustrates aspects of a feed, in accordance with various embodiments. The feed allows a user to explore new opportunities and celebrate achieving goals (e.g., therapeutic or wellness goals). The feed provides a searchable interface (element 1202).

The feed provides an interface where the user accesses a personal log of activities the user is involved in. The personal log is searchable. For example, if the user reads an article recommended by the cognitive agent 110 and highlights passages, the highlighted passages are accessible through the search. Additionally, the cognitive agent 110 can initiate a conversational stream focused on subject matter related to the highlighted passages.

The feed provides an interface to celebrate mini achievements and successes in the user's personal goals (e.g., therapeutic or wellness goals). In the feed, the cognitive agent 110 is still available (ribbon 1204) to help search, guide, or steer the user toward a therapeutic or wellness goal.

Figure 13:
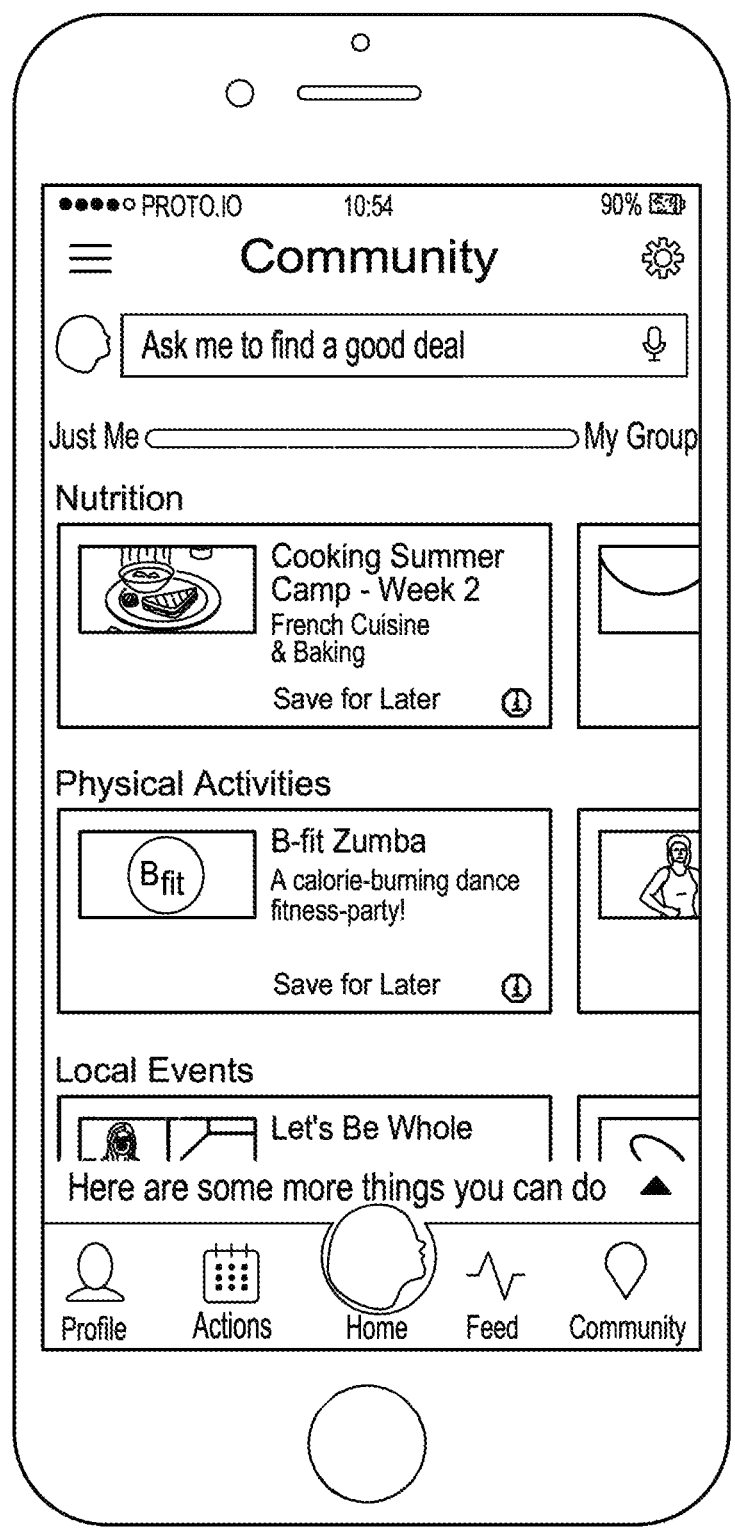
FIG. 13 shows aspects of a hyper-local community, in accordance with various embodiments.

FIG. 13 illustrates aspects of a hyper-local community, in accordance with various embodiments. A hyper-local community is a digital community that is health and wellness focused and encourages the user to find opportunities for themselves and get involved in a community that is physically close to the user. The hyper-local community allows a user to access a variety of care and wellness resources within his community and example recommendations include: Nutrition; Physical Activities; Healthcare Providers; Educations; Local Events; Services; Deals and Stores; Charities; and Products offered within the community. The cognitive agent 110 optimizes suggestions which help the user progress towards a goal as opposed to providing open ended access to hyper-local assets. The recommendations are curated and monitored for relevance to the user, based on the user's goals and interactions between the user and the cognitive agent 110.

Accordingly, the cognitive intelligence platform provides several core features including:

1) the ability to identify an appropriate action plan using narrative style interactions that generates data that includes intent and causation and using narrative style interactions;
2) monitoring: integration of offline to online clinical results across the functional medicine clinical standards;
3) the knowledge cloud that includes a comprehensive knowledge base of thousands of health related topics, an educational guide to better health aligned to western and eastern culture;
4) coaching using artificial intelligence; and
5) profile and health store that offers a holistic profile of each consumers health risks and interactions, combined with a repository of services, products, lab tests, devices, deals, supplements, pharmacy & telemedicine.

Figure 14:
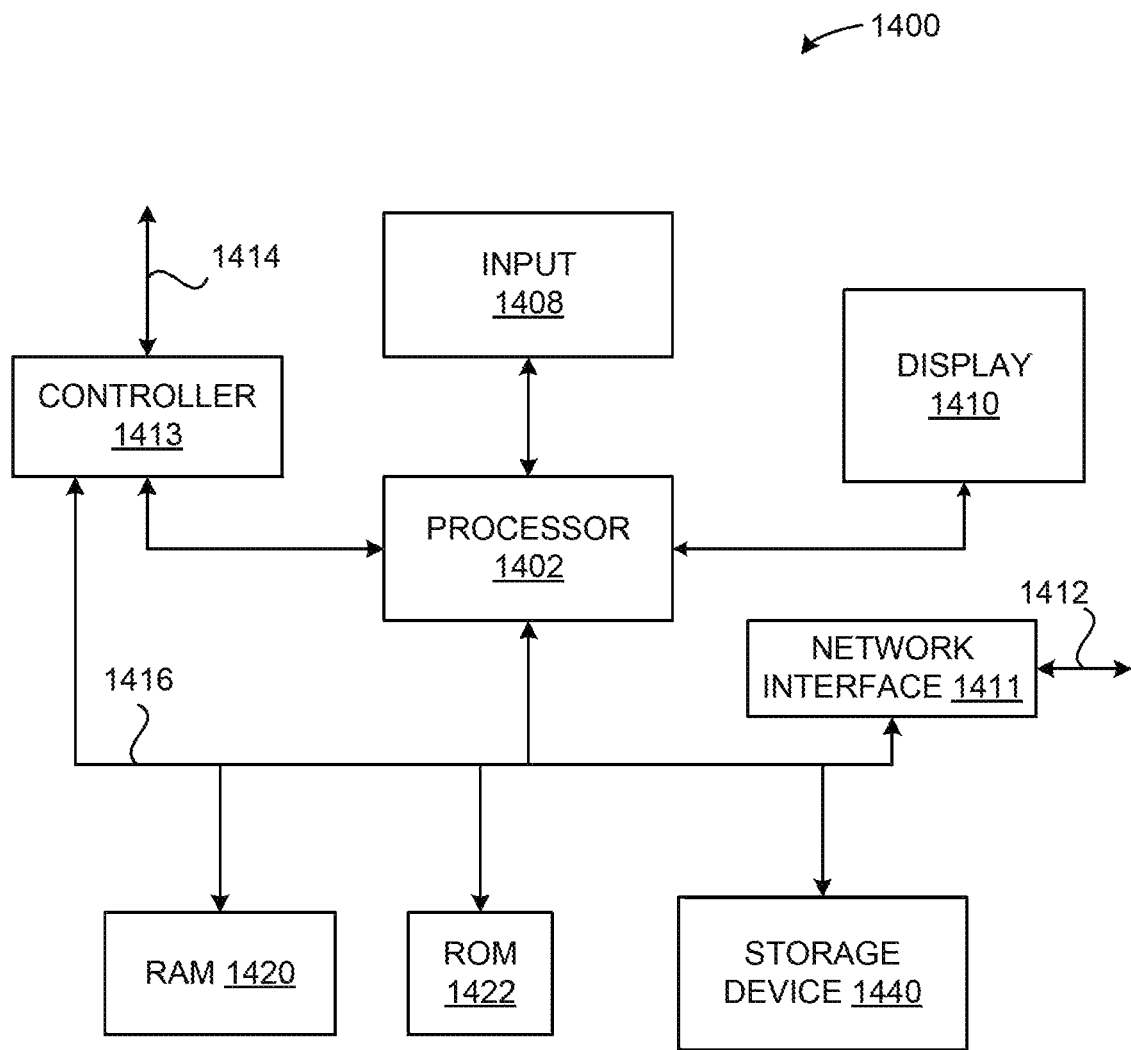
FIG. 14 illustrates a detailed view of a computing device that can represent the computing devices of FIG. 1 used to implement the various platforms and techniques described herein, according to some embodiments.

FIG. 14 illustrates a detailed view of a computing device 1400 that can be used to implement the various components described herein, according to some embodiments. In particular, the detailed view illustrates various components that can be included in the user device 104 illustrated in FIG. 1, as well as the several computing devices implementing the cognitive intelligence platform 102. As shown in FIG. 14, the computing device 1400 can include a processor 1402 that represents a microprocessor or controller for controlling the overall operation of the computing device 1400. The computing device 1400 can also include a user input device 1408 that allows a user of the computing device 1400 to interact with the computing device 1400. For example, the user input device 1408 can take a variety of forms, such as a button, keypad, dial, touch screen, audio input interface, visual/image capture input interface, input in the form of sensor data, and so on. Still further, the computing device 1400 can include a display 1410 that can be controlled by the processor 1402 to display information to the user. A data bus 1416 can facilitate data transfer between at least a storage device 1440, the processor 1402, and a controller 1413. The controller 1413 can be used to interface with and control different equipment through an equipment control bus 1414. The computing device 1400 can also include a network/bus interface 1411 that couples to a data link 1412. In the case of a wireless connection, the network/bus interface 1411 can include a wireless transceiver.

As noted above, the computing device 1400 also includes the storage device 1440, which can comprise a single disk or a collection of disks (e.g., hard drives), and includes a storage management module that manages one or more partitions within the storage device 1440. In some embodiments, storage device 1440 can include flash memory, semiconductor (solid-state) memory or the like. The computing device 1400 can also include a Random-Access Memory (RAM) 1420 and a Read-Only Memory (ROM) 1422. The ROM 1422 can store programs, utilities or processes to be executed in a non-volatile manner. The RAM 1420 can provide volatile data storage, and stores instructions related to the operation of processes and applications executing on the computing device.

Figure 15:
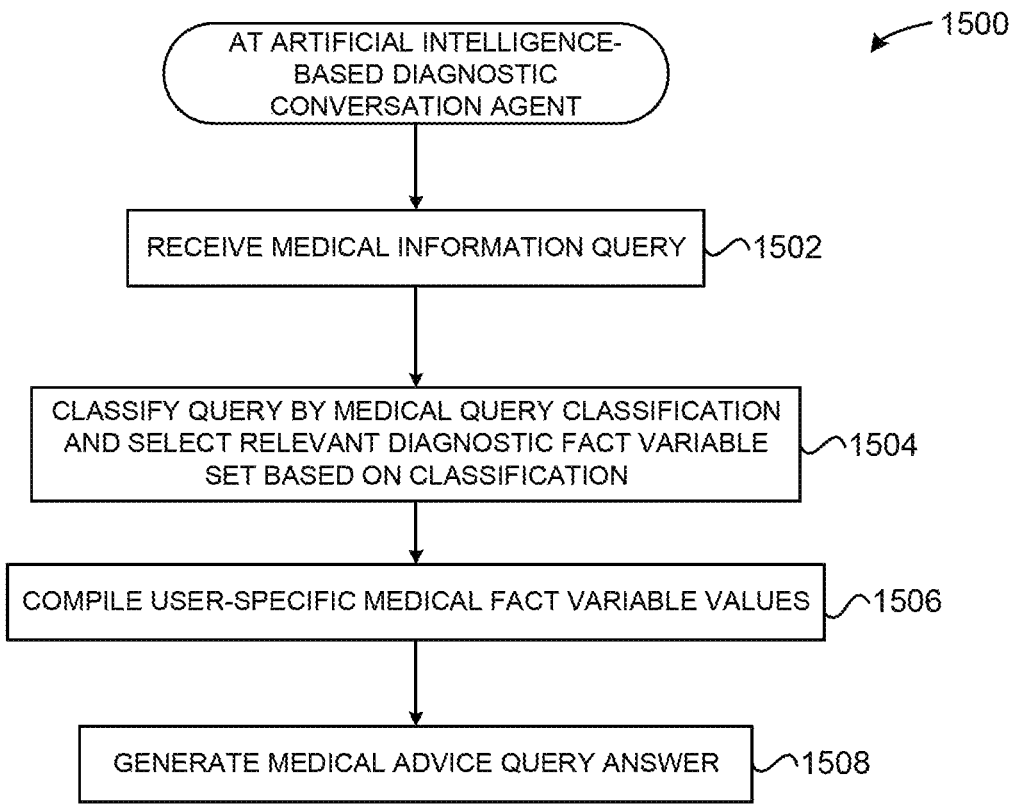
FIG. 15 shows a method, in accordance with various embodiments.

FIG. 15 shows a method (1500), in accordance with various embodiments, for answering a user-generated natural language medical information query based on a diagnostic conversational template.

In the method as shown in FIG. 15, an artificial intelligence-based diagnostic conversation agent receives a user-generated natural language medical information query as entered by a user through a user interface on a computer device (FIG. 15, block 1502). In some embodiments, the artificial intelligence-based diagnostic conversation agent is the conversation agent 110 of FIG. 1. In some embodiments the computer device is the mobile device 104 of FIG. 1. One example of a user-generated natural language medical information query as entered by a user through a user interface is the question "Is a blood sugar of 90 normal?" as shown in line 402 of FIG. 4. In some embodiments, receiving a user-generated natural language medical information query as entered by a user through a user interface on a computer device (FIG. 15, block 1502) is Step 1 as earlier discussed in the context of "Analyzing Conversational Context As Part of Conversational Analysis".

In response to the user-generated natural language medical information query, the artificial intelligence-based diagnostic conversation agent selects a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504). In some embodiments, the artificial intelligence-based diagnostic conversation agent selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504) is accomplished through one or more of Steps 2-6 as earlier discussed in the context of "Analyzing Conversational Context As Part of Conversational Analysis".

FIG. 15 further shows compiling user-specific medical fact variable values for one or more respective medical fact variables of the diagnostic fact variable set (FIG. 15, block 1506). Compiling user-specific medical fact variable values for one or more respective medical fact variables of the diagnostic fact variable set (FIG. 15, block 1506) may include one or more of Steps 2-6 as earlier discussed in the context of "Analyzing Conversational Context As Part of Conversational Analysis".

In response to the user-specific medical fact variable values, the artificial intelligence-based diagnostic conversation agent generates a medical advice query answer in response to the user-generated natural language medical information query (FIG. 15, block 1508). In some embodiments, this is Step 7 as earlier discussed in the context of "Analyzing Conversational Context As Part of Conversational Analysis".

In some embodiments, compiling user-specific medical fact variable values (FIG. 15, block 1506) includes extracting a first set of user-specific medical fact variable values from a local user medical information profile associated with the user-generated natural language medical information query and requesting a second set of user specific medical fact variable values through natural-language questions sent to the user interface on the mobile device (e.g. the microsurvey data 206 of FIG. 2 that came from the microsurvey 116 of FIG. 1). The local user medical information profile can be the profile as generated in FIG. 7A at block 708.

In some embodiments, compiling user-specific medical fact variable values (FIG. 15, block 1506) includes extracting a third set of user-specific medical fact variable values that are lab result values from the local user medical information profile associated with the user generated natural language medical information query. The local user medical information profile can be the profile as generated in FIG. 7A at block 708.

In some embodiments, compiling user-specific medical fact variable values (FIG. 15, block 1506) includes extracting a fourth set of user-specific medical variable values from a remote medical data service profile associated with the local user medical information profile. The remote medical data service profile can be the service provider data 202 of FIG. 2, which can come from the service provider 112 of FIG. 1. The local user medical information profile can be the profile as generated in FIG. 7A at block 708.

In some embodiments, compiling user-specific medical fact variable values (FIG. 15, block 1506) includes extracting a fifth set of user-specific medical variable values from demographic characterizations provided by a remote data service analysis of the local user medical information profile. The remote demographic characterizations can be the service provider data 202 of FIG. 2, which can come from the service provider 112 of FIG. 1. The local user medical information profile can be the profile as generated in FIG. 7A at block 708.

In some embodiments, generating the medical advice query answer (FIG. 15, block 1508) includes providing a treatment action-item recommendation in response to user-specific medical fact values that may be non-responsive to the medical question presented in the user-generated natural language medical information query. Such an action could define an action plan based on the data compiled (FIG. 15, block 1506), as shown in FIG. 7C, block 758.

In some embodiments, generating the medical advice query answer (FIG. 15, block 1506) includes providing a medical education media resource in response to user-specific medical fact variable values that may be non-responsive to the medical question presented in the user-generated natural language medical information query. Such an action could serve to educate and inform the user, as in block 758 of FIG. 7C.

In some embodiments, selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets (FIG. 15, block 1504) includes classifying the user-generated natural language medical information query into one of a set of domain-directed medical query classifications based on relevance to the local user medical information profile associated with the user-generated natural language medical information query. The local user medical information profile can be the profile as generated in FIG. 7A at block 708.

In some embodiments, the method (1500) for answering a user-generated natural language medical information query based on a diagnostic conversational template is implemented as a computer program product in a computer-readable medium.

In some embodiments, the system and method 1500 shown in FIG. 15 and described above is implemented on the computing device 1400 shown in FIG. 14.

Figure 16:
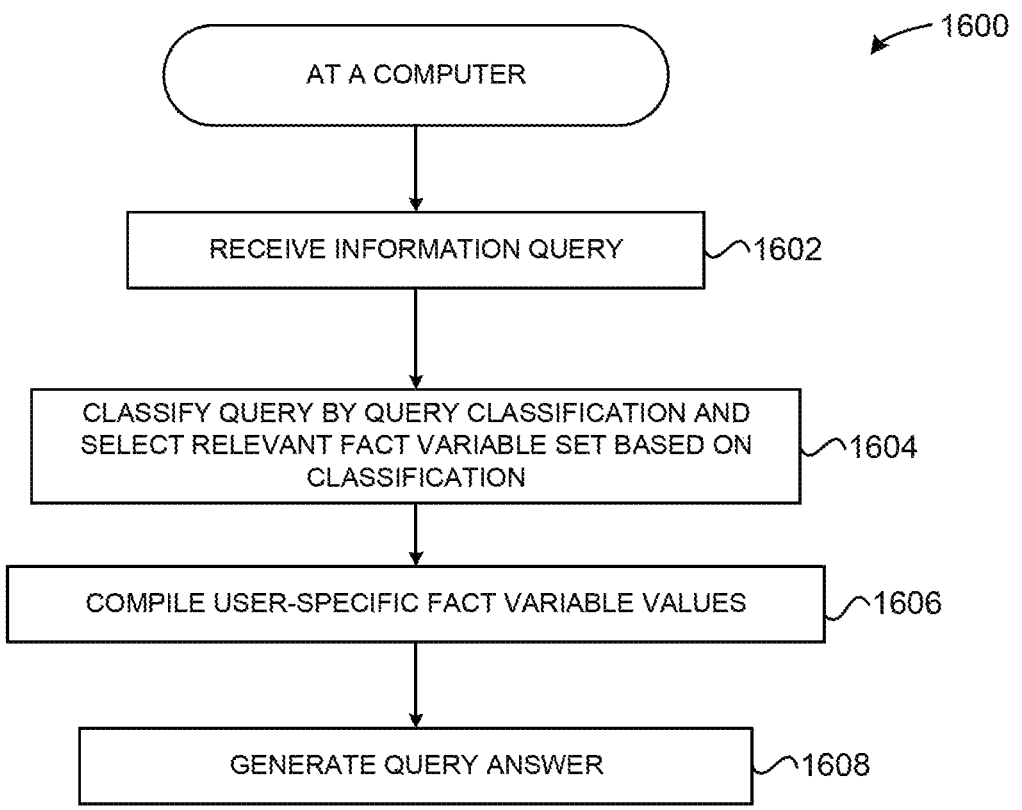
FIG. 16 shows a method, in accordance with various embodiments.

FIG. 16 shows a method (1600), in accordance with various embodiments, for answering a user-generated natural language query based on a conversational template.

In the method as shown in FIG. 16, an artificial intelligence-based conversation agent receives a user-generated natural language query as entered by a user through a user interface (FIG. 16, block 1602). In some embodiments, the artificial intelligence-based conversation agent is the conversation agent 110 of FIG. 1. In some embodiments, the user interface is on a computer device. In some embodiments the computer device is the mobile device 104 of FIG. 1. One example of a user-generated natural language query as entered by a user through a user interface is the question "Is a blood sugar of 90 normal?" as shown in line 402 of FIG. 4. In some embodiments, receiving a user-generated natural language query as entered by a user through a user interface on a computer device (FIG. 16, block 1602) is Step 1 as earlier discussed in the context of "Analyzing Conversational Context As Part of Conversational Analysis".

In response to the user-generated natural language query, the artificial intelligence-based conversation agent selects a fact variable set relevant to generating a query answer for the user-generated natural language query by classifying the user-generated natural language query into one of a set of domain-directed query classifications associated with respective fact variable sets (FIG. 16, block 1604). In some embodiments, the artificial intelligence-based conversation agent selecting a fact variable set relevant to generating a query answer for the user-generated natural language query by classifying the user-generated natural language query into one of a set of domain-directed query classifications associated with respective fact variable sets (FIG. 16, block 1604) is accomplished through one or more of Steps 2-6 as earlier discussed in the context of "Analyzing Conversational Context As Part of Conversational Analysis".

FIG. 16 further shows compiling user-specific variable values for one or more respective fact variables of the fact variable set (FIG. 16, block 1606). Compiling user-specific fact variable values for one or more respective fact variables of the fact variable set (FIG. 16, block 1606) may include one or more of Steps 2-6 as earlier discussed in the context of "Analyzing Conversational Context As Part of Conversational Analysis".

In response to the user-specific fact variable values, the artificial intelligence-based conversation agent generates a query answer in response to the user-generated natural language query (FIG. 16, block 1608). In some embodiments, this is Step 7 as earlier discussed in the context of "Analyzing Conversational Context As Part of Conversational Analysis".

In some embodiments, compiling user-specific fact variable values (FIG. 16, block 1606) includes extracting a first set of user-specific fact variable values from a local user profile associated with the user-generated natural language query and requesting a second set of user specific variable values through natural-language questions sent to the user interface on the mobile device (e.g. the microsurvey data 206 of FIG. 2 that came from the microsurvey 116 of FIG. 1). The local user profile can be the profile as generated in FIG. 7A at block 708. In some embodiments, the natural language questions sent to the user interface on the mobile device can be a part of a conversation template.

In some embodiments, compiling user-specific fact variable values (FIG. 16, block 1606) includes extracting a third set of user-specific fact variable values that are test result values from the local user profile associated with the user generated natural language query. The local user profile can be the profile as generated in FIG. 7A at block 708. In some embodiments, compiling user-specific fact variable values (FIG. 16, block 1606) includes extracting a fourth set of user-specific variable values from a remote data service profile associated with the local user profile. The remote data service profile can be the service provider data 202 of FIG. 2, which can come from the service provider 112 of FIG. 1. The local user profile can be the profile as generated in FIG. 7A at block 708.

In some embodiments, compiling user-specific fact variable values (FIG. 16, block 1606) includes extracting a fifth set of user-specific variable values from demographic characterizations provided by a remote data service analysis of the local user profile. The remote demographic characterizations can be the service provider data 202 of FIG. 2, which can come from the service provider 112 of FIG. 1. The local user profile can be the profile as generated in FIG. 7A at block 708.

In some embodiments, generating the query answer (FIG. 16, block 1608) includes providing an action-item recommendation in response to user-specific fact values that may be non-responsive to the question presented in the user-generated natural language query. Such an action could define an action plan based on the data compiled (FIG. 16, block 1606), as shown in FIG. 7C, block 758.

In some embodiments, generating the advice query answer (FIG. 16, block 1606) includes providing an education media resource in response to user-specific fact variable values that may be non-responsive to the question presented in the user-generated natural language query. Such an action could serve to educate and inform the user, as in block 758 of FIG. 7C.

In some embodiments, selecting a fact variable set relevant to generating a query answer for the user-generated natural language query by classifying the user-generated natural language query into one of a set of domain-directed query classifications associated with respective fact variable sets (FIG. 16, block 1604) includes classifying the user-generated natural language query into one of a set of domain-directed query classifications based on relevance to the local user profile associated with the user-generated natural language query. The local user profile can be the profile as generated in FIG. 7A at block 708.

In some embodiments, the method (1600) for answering a user-generated natural language query based on a conversational template is implemented as a computer program product in a computer-readable medium.

In some embodiments, the system and method shown in FIG. 16 and described above is implemented in the cognitive intelligence platform 102 shown in FIG. 1.

In the cognitive intelligence platform 102, a cognitive agent 110 is configured for receiving a user-generated natural language query at an artificial intelligence-based conversation agent from a user interface on a user device 104 (FIG. 16, block 1602).

A critical thinking engine 108 is configured for, responsive to content of the user-generated natural language query, selecting a fact variable set relevant to generating a query answer for the user-generated natural language query by classifying the user-generated natural language query into one of a set of domain-directed query classifications associated with respective fact variable sets (FIG. 16, block 1604).

Included is a knowledge cloud 106 that compiles user-specific fact variable values for one or more respective fact variables of the fact variable set (FIG. 16, block 1606).

Responsive to the fact variable values, the cognitive agent 110 is further configured for generating the query answer in response to the user-generated natural language query (FIG. 16, block 1606).

In some embodiments, the system and method 1600 shown in FIG. 16 and described above is implemented on the computing device 1400 shown in FIG. 14.

Figure 17:
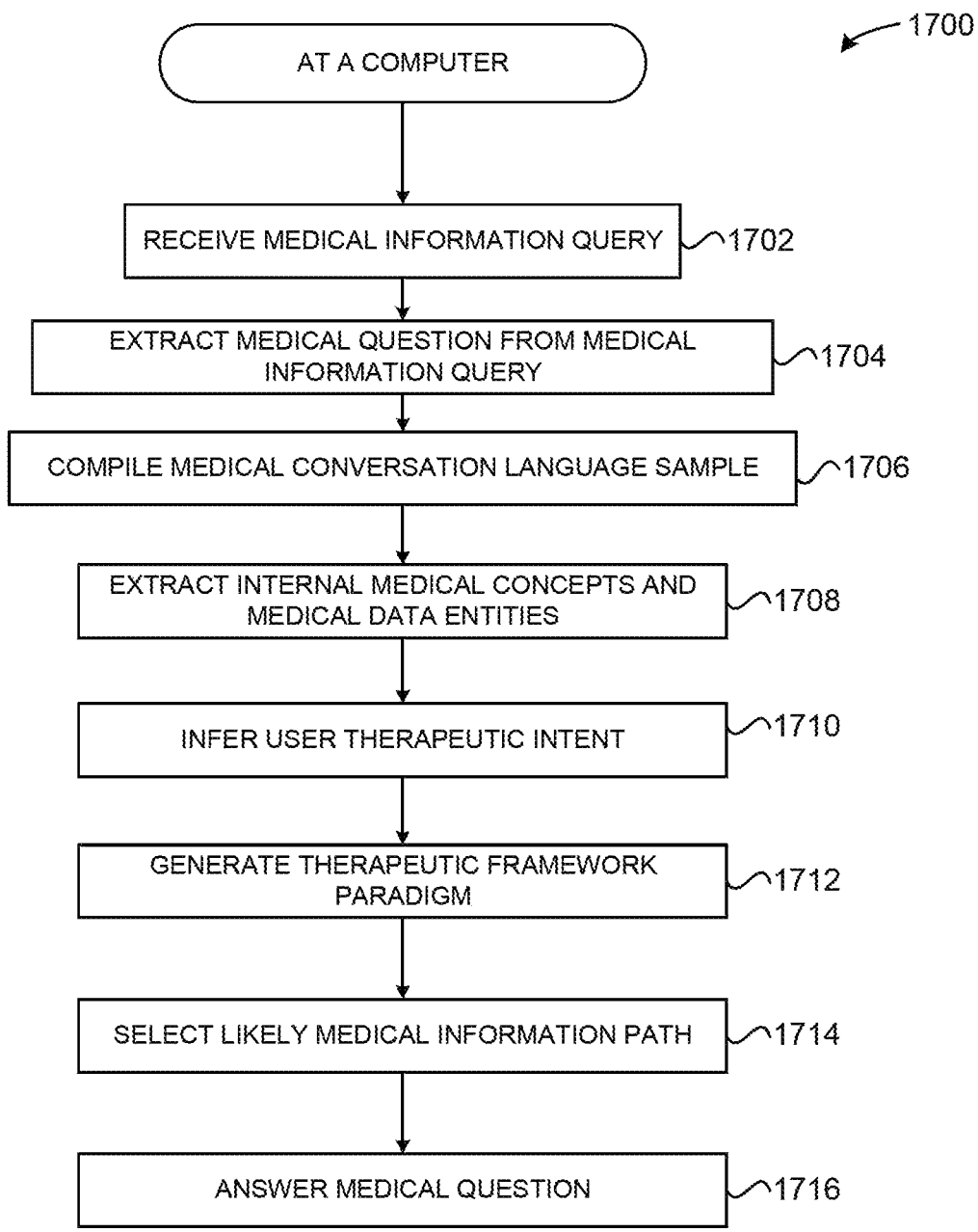
FIG. 17 shows a method, in accordance with various embodiments.

FIG. 17 shows a computer-implemented method 1700 for answering natural language medical information questions posed by a user of a medical conversational interface of a cognitive artificial intelligence system. In some embodiments, the method 1700 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14.

The method 1700 involves receiving a user-generated natural language medical information query from a medical conversational user interface at an artificial intelligence-based medical conversation cognitive agent (block 1702). In some embodiments, receiving a user-generated natural language medical information query from a medical conversational user interface at an artificial intelligence-based medical conversation cognitive agent (block 1702) is performed by a cognitive agent that is a part of the cognitive intelligence platform and is configured for this purpose. In some embodiments, the artificial intelligence-based diagnostic conversation agent is the conversation agent 110 of FIG. 1. One example of a user-generated natural language medical information query is "Is a blood sugar of 90 normal?" as shown in line 402 of FIG. 4. In some embodiments, the user interface is on the mobile device 104 of FIG. 1. In some embodiments, receiving a user-generated natural language medical information query from a medical conversational user interface at an artificial intelligence-based medical conversation cognitive agent (block 1702) is Step 1 as earlier discussed in the context of "Analyzing Conversational Context As Part of Conversational Analysis".

The method 1700 further includes extracting a medical question from a user of the medical conversational user interface from the user-generated natural language medical information query (block 1704). In some embodiments, extracting a medical question from a user of the medical conversational user interface from the user-generated natural language medical information query (block 1704) is performed by a critical thinking engine configured for this purpose. In some embodiments, the critical thinking engine is the critical thinking engine 108 of FIG. 1. In some embodiments, extracting a medical question from a user of the medical conversational user interface from the user-generated natural language medical information query (block 1704) is accomplished through one or more of Steps 2-6 as earlier discussed in the context of "Analyzing Conversational Context As Part of Conversational Analysis".

The method 1700 includes compiling a medical conversation language sample (block 1706). In some embodiments, compiling a medical conversation language sample (block 1706) is performed by a critical thinking engine configured for this purpose. In some embodiments, the critical thinking engine is the critical thinking engine 108 of FIG. 1. The medical conversation language sample can include items of health-information-related-text derived from a health-related conversation between the artificial intelligence-based medical conversation cognitive agent and the user. In some embodiments compiling a medical conversation language sample (block 1706) is accomplished through one or more of Steps 2-6 as earlier discussed in the context of "Analyzing Conversational Context As Part of Conversational Analysis".

The method 1700 involves extracting internal medical concepts and medical data entities from the medical conversation language sample (block 1708). In some embodiments, extracting internal medical concepts and medical data entities from the medical conversation language sample (block 1708) is performed by a critical thinking engine configured for this purpose. In some embodiments, the critical thinking engine is the critical thinking engine 108 of FIG. 1. The internal medical concepts can include descriptions of medical attributes of the medical data entities. In some embodiments, extracting internal medical concepts and medical data entities from the medical conversation language sample (block 1708) is accomplished through one or more of Steps 2-6 as earlier discussed in the context of "Analyzing Conversational Context As Part of Conversational Analysis".

The method 1700 involves inferring a therapeutic intent of the user from the internal medical concepts and the medical data entities (block 1710). In some embodiments, inferring a therapeutic intent of the user from the internal medical concepts and the medical data entities (block 1710) is performed by a critical thinking engine configured for this purpose. In some embodiments, the critical thinking engine is the critical thinking engine 108 of FIG. 1. In some embodiments, inferring a therapeutic intent of the user from the internal medical concepts and the medical data entities (block 1710) is accomplished as in Step 2 as earlier discussed in the context of "Analyzing Conversational Context As Part of Conversational Analysis".

The method 1700 includes generating a therapeutic paradigm logical framework 1800 for interpreting of the medical question (block 1712). In some embodiments, generating a therapeutic paradigm logical framework 1800 for interpreting of the medical question (block 1712) is performed by a critical thinking engine configured for this purpose. In some embodiments, the critical thinking engine is the critical thinking engine 108 of FIG. 1. In some embodiments, generating a therapeutic paradigm logical framework 1800 for interpreting of the medical question (block 1712) is accomplished as in Step 5 as earlier discussed in the context of "Analyzing Conversational Context As Part of Conversational Analysis".

Figure 18:
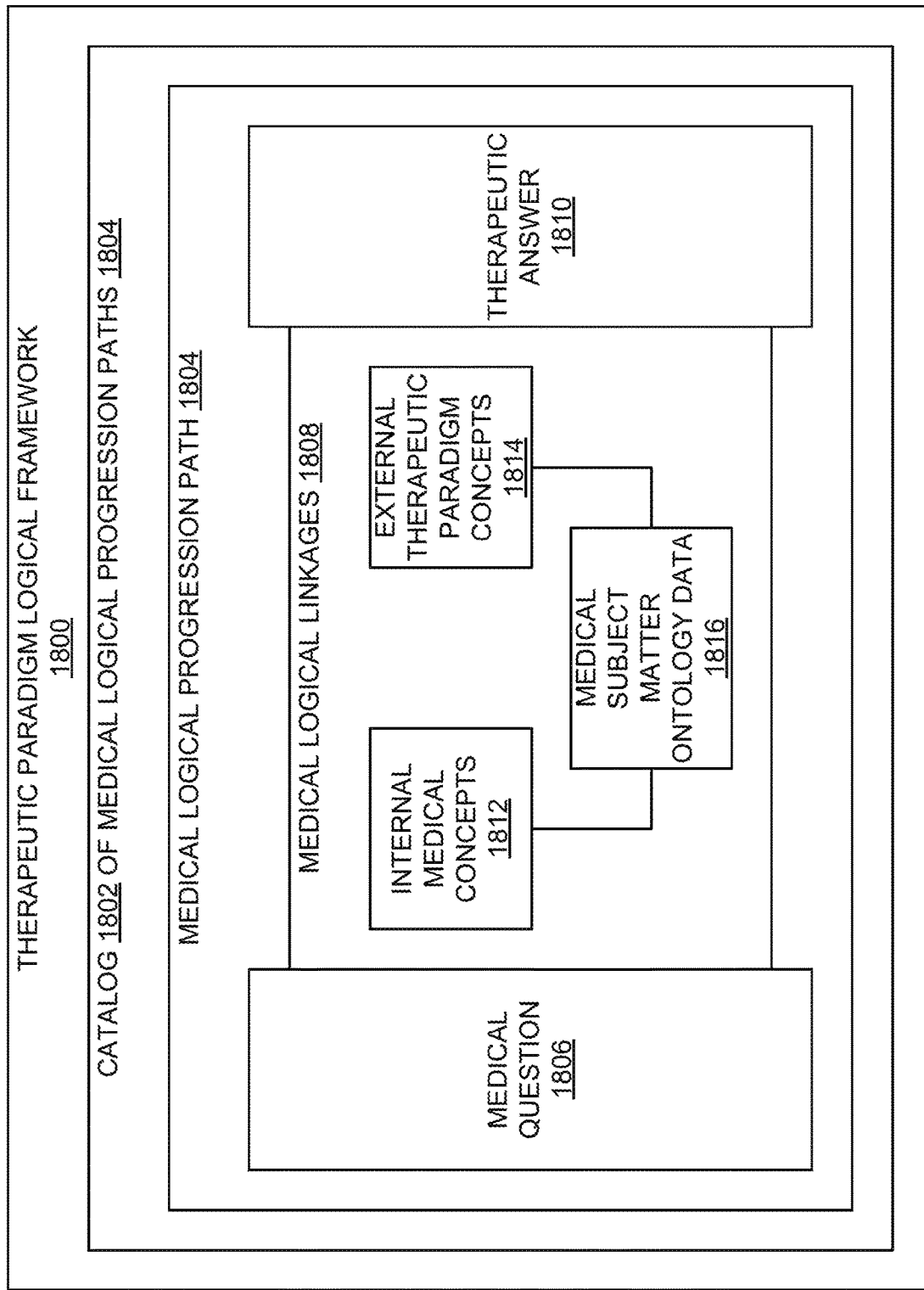
FIG. 18 shows a therapeutic paradigm logical framework, in accordance with various embodiments

FIG. 18 shows an example therapeutic paradigm logical framework 1800. The therapeutic paradigm logical framework 1800 includes a catalog 1802 of medical logical progression paths 1804 from the medical question 1806 to respective therapeutic answers 1810.

Each of the medical logical progression paths 1804 can include one or more medical logical linkages 1808 from the medical question 1806 to a therapeutic path-specific answer 1810.

The medical logical linkages 1808 can include the internal medical concepts 1812 and external therapeutic paradigm concepts 1814 derived from a store of medical subject matter ontology data 1816. In some embodiments, the store of subject matter ontology data 1816 is contained in a knowledge cloud. In some embodiments, the knowledge cloud is the knowledge cloud 102 of FIGS. 1 and 2. In some embodiments, the subject matter ontology data 1816 is the subject matter ontology data 216 of FIG. 2. In some embodiments, the subject matter ontology data 1816 includes the subject matter ontology 300 of FIG. 3.

The method 1700 shown in FIG. 17 further includes selecting a likely medical information path from among the medical logical progression paths 1804 to a likely path-dependent medical information answer based at least in part upon the therapeutic intent of the user (block 1714). In some embodiments, selecting a likely medical information path from among the medical logical progression paths 1804 to a likely path-dependent medical information answer based at least in part upon the therapeutic intent of the user (block 1714 is performed by a critical thinking engine configured for this purpose. In some embodiments, the critical thinking engine is the critical thinking engine 108 of FIG. 1. The selection can also be based in part upon the sufficiency of medical diagnostic data to complete the medical logical linkages 1808. In some embodiments, selection can also be based in part upon the sufficiency of medical diagnostic data to complete the medical logical linkages 1808 can be performed by a critical thinking engine that is further configured for this purpose. In some embodiments, the critical thinking engine is the critical thinking engine 108 of FIG. 1. The medical diagnostic data can include user-specific medical diagnostic data. The selection can also be based in part upon treatment sub-intents including tactical constituents related to the therapeutic intent of the user by the store of medical subject matter ontology data 1816. In some embodiments, selection based in part upon treatment sub-intents including tactical constituents related to the therapeutic intent of the user by the store of medical subject matter ontology data 1816 can be performed by a critical thinking engine further configured for this purpose. In some embodiments, the critical thinking engine is the critical thinking engine 108 of FIG. 1. The selection can further occur after requesting additional medical diagnostic data from the user. An example of requesting additional medical diagnostic data from the user is shown in FIG. 4 on line 406 "I need some additional information in order to answer this question, was this an in-home glucose test or was it done by a lab or testing service". In some embodiments, the process of selection after requesting additional medical diagnostic data from the user can be performed by a critical thinking engine further configured for this purpose. In some embodiments, the critical thinking engine is the critical thinking engine 108 of FIG. 1. In some embodiments, selecting a likely medical information path from among the medical logical progression paths 1804 to a likely path-dependent medical information answer based at least in part upon the therapeutic intent of the user (block 1714) is accomplished through one or more of Steps 5-6 as earlier discussed in the context of "Analyzing Conversational Context As Part of Conversational Analysis".

The method 1700 involves answering the medical question by following the likely medical information path to the likely path-dependent medical information answer (block 1716). In some embodiments, answering the medical question by following the likely medical information path to the likely path-dependent medical information answer (block 1716) is performed by a critical thinking engine configured for this purpose. In some embodiments, the critical thinking engine is the critical thinking engine 108 of FIG. 1. In some embodiments, answering the medical question by following the likely medical information path to the likely path-dependent medical information answer (block 1716) is accomplished as in Step 7 as earlier discussed in the context of "Analyzing Conversational Context As Part of Conversational Analysis".

The method 1700 can further include relating medical inference groups of the internal medical concepts. In some embodiments, relating medical inference groups of the internal medical concepts is performed by a critical thinking engine further configured for this purpose. In some embodiments, the critical thinking engine is the critical thinking engine 108 of FIG. 1. Relating medical inference groups of the internal medical concepts can be based at least in part on shared medical data entities for which each internal medical concept of a medical inference group of internal medical concepts describes a respective medical data attribute. In some embodiments, relating medical inference groups of the internal medical concepts based at least in part on shared medical data entities for which each internal medical concept of a medical inference group of internal medical concepts describes a respective medical data attribute can be performed by a critical thinking engine further configured for this purpose. In some embodiments, the critical thinking engine is the critical thinking engine 108 of FIG. 1.

In some embodiments, the method 1700 of FIG. 17 is implemented as a computer program product in a computer-readable medium.

Figure 19:
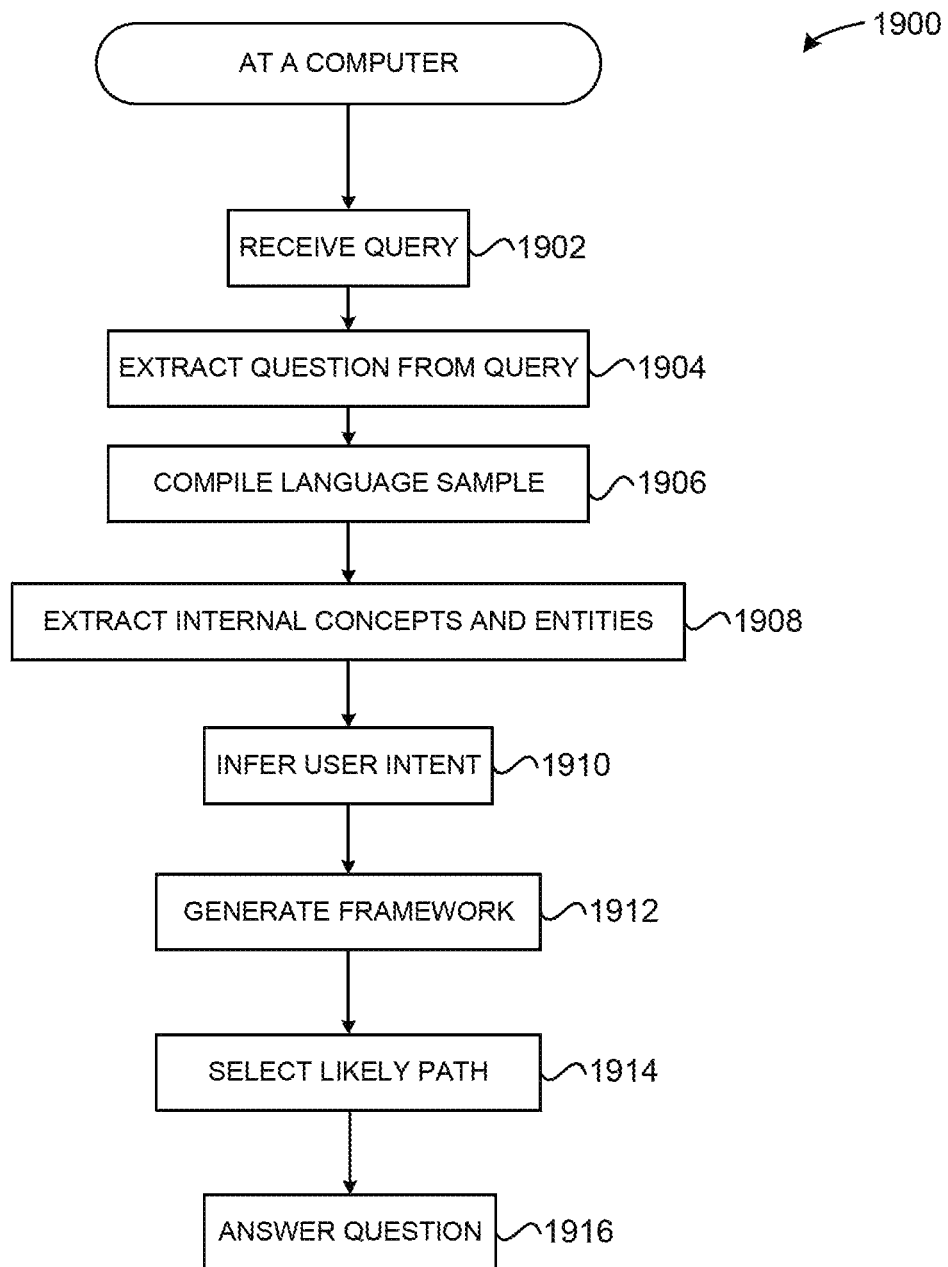
FIG. 19 shows a method, in accordance with various embodiments.

FIG. 19 shows a computer-implemented method 1900 for answering natural language questions posed by a user of a conversational interface of an artificial intelligence system. In some embodiments, the method 1900 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14.

The method 1900 involves receiving a user-generated natural language query at an artificial intelligence-based conversation agent (block 1902). In some embodiments, receiving a user-generated natural language query from a conversational user interface at an artificial intelligence-based conversation cognitive agent (block 1902) is performed by a cognitive agent that is a part of the cognitive intelligence platform and is configured for this purpose. In some embodiments, the artificial intelligence-based conversation agent is the conversation agent 110 of FIG. 1. One example of a user-generated natural language query is "Is a blood sugar of 90 normal?" as shown in line 402 of FIG. 4. In some embodiments, the user interface is on the mobile device 104 of FIG. 1. In some embodiments, receiving a user-generated natural language query from a conversational user interface at an artificial intelligence-based conversation cognitive agent (block 1902) is Step 1 as earlier discussed in the context of "Analyzing Conversational Context As Part of Conversational Analysis".

The method 1900 further includes extracting a question from a user of the conversational user interface from the user-generated natural language query (block 1904). In some embodiments, extracting a question from a user of the conversational user interface from the user-generated natural language query (block 1904) is performed by a critical thinking engine configured for this purpose. In some embodiments, the critical thinking engine is the critical thinking engine 108 of FIG. 1. In some embodiments, extracting a question from a user of the conversational user interface from the user-generated natural language query (block 1904) is accomplished through one or more of Steps 2-6 as earlier discussed in the context of "Analyzing Conversational Context As Part of Conversational Analysis".

The method 1900 includes compiling a language sample (block 1906). In some embodiments, compiling a language sample (block 1906) is performed by a critical thinking engine configured for this purpose. In some embodiments, the critical thinking engine is the critical thinking engine 108 of FIG. 1. The language sample can include items of health-information-related-text derived from a health-related conversation between the artificial intelligence-based conversation cognitive agent and the user. In some embodiments compiling a language sample (block 1906) is accomplished through one or more of Steps 2-6 as earlier discussed in the context of "Analyzing Conversational Context As Part of Conversational Analysis".

The method 1900 involves extracting internal concepts and entities from the language sample (block 1908). In some embodiments, extracting internal concepts and entities from the language sample (block 1908) is performed by a critical thinking engine configured for this purpose. In some embodiments, the critical thinking engine is the critical thinking engine 108 of FIG. 1. The internal concepts can include descriptions of attributes of the entities. In some embodiments, extracting internal concepts and entities from the language sample (block 1908) is accomplished through one or more of Steps 2-6 as earlier discussed in the context of "Analyzing Conversational Context As Part of Conversational Analysis".

The method 1900 involves inferring an intent of the user from the internal concepts and the entities (block 1910). In some embodiments, inferring an intent of the user from the internal concepts and the entities (block 1910) is performed by a critical thinking engine configured for this purpose. In some embodiments, the critical thinking engine is the critical thinking engine 108 of FIG. 1. In some embodiments, inferring an intent of the user from the internal concepts and the entities (block 1910) is accomplished as in Step 2 as earlier discussed in the context of "Analyzing Conversational Context As Part of Conversational Analysis".

The method 1900 includes generating a logical framework 2000 for interpreting of the question (block 1912). In some embodiments, generating a logical framework 2000 for interpreting of the question (block 1912) is performed by a critical thinking engine configured for this purpose. In some embodiments, the critical thinking engine is the critical thinking engine 108 of FIG. 1. In some embodiments, generating a logical framework 2000 for interpreting of the question (block 1912) is accomplished as in Step 5 as earlier discussed in the context of "Analyzing Conversational Context As Part of Conversational Analysis".

Figure 20:
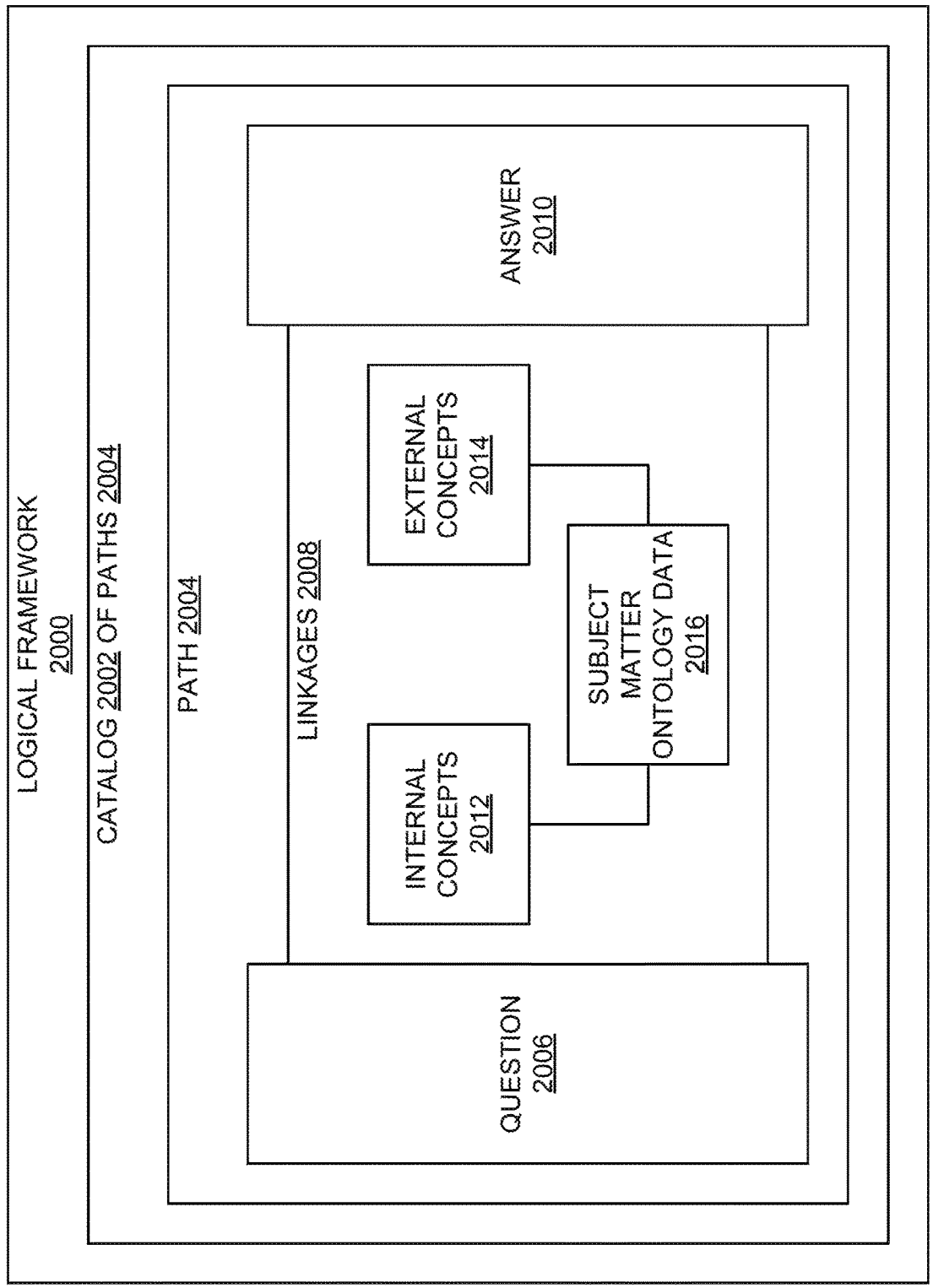
FIG. 20 shows a paradigm logical framework, in accordance with various embodiments.

FIG. 20 shows an example logical framework 2000. The logical framework 2000 includes a catalog 2002 of paths 2004 from the question 2006 to respective answers 2010.

Each of the paths 2004 can include one or more linkages 2008 from the question 2006 to a path-specific answer 2010.

The linkages 2008 can include the internal concepts 2012 and external concepts 2014 derived from a store of subject matter ontology data 2016. In some embodiments, the store of subject matter ontology data 2016 is contained in a knowledge cloud. In some embodiments, the knowledge cloud is the knowledge cloud 102 of FIGS. 1 and 2. In some embodiments, the subject matter ontology data 2016 is the subject matter ontology data 216 of FIG. 2. In some embodiments, the subject matter ontology data 2016 includes the subject matter ontology 300 of FIG. 3.

The method 1900 shown in FIG. 19 further includes selecting a likely path from among the paths 2004 to a likely path-dependent answer based at least in part upon the intent of the user (block 1914). In some embodiments, selecting a likely path from among the paths 2004 to a likely path-dependent answer based at least in part upon the intent of the user (block 1914 is performed by a critical thinking engine configured for this purpose. In some embodiments, the critical thinking engine is the critical thinking engine 108 of FIG. 1. The selection can also be based in part upon the sufficiency of data to complete the linkages 2008. In some embodiments, selection can also be based in part upon the sufficiency of data to complete the linkages 2008 can be performed by a critical thinking engine that is further configured for this purpose. In some embodiments, the critical thinking engine is the critical thinking engine 108 of FIG. 1. The data can include user-specific data. The selection can also be based in part upon treatment sub-intents including tactical constituents related to the intent of the user by the store of subject matter ontology data 2016. In some embodiments, selection based in part upon treatment sub-intents including tactical constituents related to the intent of the user by the store of subject matter ontology data 2016 can be performed by a critical thinking engine further configured for this purpose. In some embodiments, the critical thinking engine is the critical thinking engine 108 of FIG. 1. The selection can further occur after requesting additional data from the user. An example of requesting additional data from the user is shown in FIG. 4 on line 406 "I need some additional information in order to answer this question, was this an in-home glucose test or was it done by a lab or testing service". In some embodiments, the process of selection after requesting additional data from the user can be performed by a critical thinking engine further configured for this purpose. In some embodiments, the critical thinking engine is the critical thinking engine 108 of FIG. 1. In some embodiments, selecting a likely path from among the paths 2004 to a likely path-dependent answer based at least in part upon the intent of the user (block 1914) is accomplished through one or more of Steps 5-6 as earlier discussed in the context of "Analyzing Conversational Context As Part of Conversational Analysis".

The method 1900 involves answering the question by following the likely path to the likely path-dependent answer (block 1916). In some embodiments, answering the question by following the likely path to the likely path-dependent answer (block 1916) is performed by a critical thinking engine configured for this purpose. In some embodiments, the critical thinking engine is the critical thinking engine 108 of FIG. 1. In some embodiments, answering the question by following the likely path to the likely path-dependent answer (block 1916) is accomplished as in Step 7 as earlier discussed in the context of "Analyzing Conversational Context As Part of Conversational Analysis".

The method 1900 can further include relating inference groups of the internal concepts. In some embodiments, relating inference groups of the internal concepts is performed by a critical thinking engine further configured for this purpose. In some embodiments, the critical thinking engine is the critical thinking engine 108 of FIG. 1. Relating inference groups of the internal concepts can be based at least in part on shared entities for which each internal concept of an inference group of internal concepts describes a respective data attribute. In some embodiments, relating inference groups of the internal concepts based at least in part on shared entities for which each internal concept of an inference group of internal concepts describes a respective data attribute can be performed by a critical thinking engine further configured for this purpose. In some embodiments, the critical thinking engine is the critical thinking engine 108 of FIG. 1.

In some embodiments, the method 1900 of FIG. 19 is implemented as a computer program product in a computer-readable medium.

Figure 21:
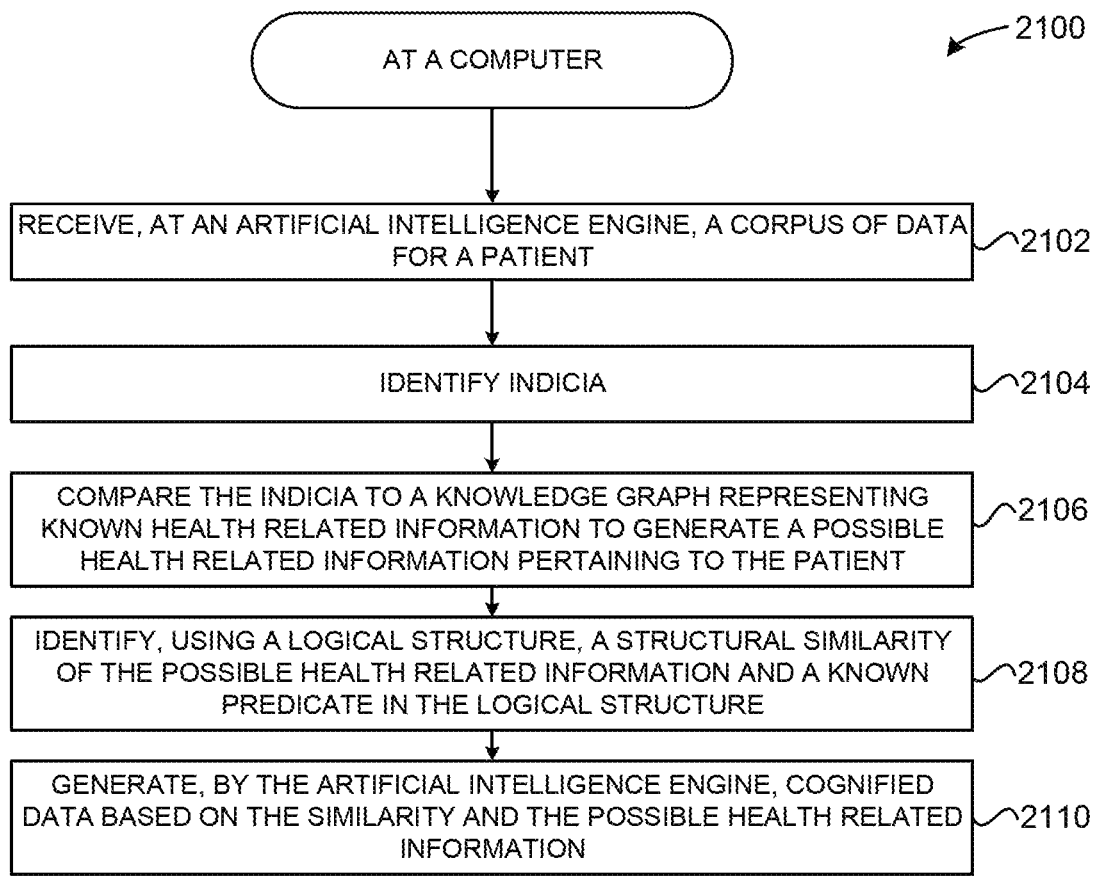
FIG. 21 shows a method for cognifying unstructured data, in accordance with various embodiments.

FIG. 21 shows a computer-implemented method 2100 for generated cognified data using unstructured data. In some embodiments, the method 2100 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2100 may include operations that are implemented in computer instructions stored in a memory and executed by a processor of a computing device.

At block 2102, the processing device may receive, at an artificial intelligence engine, a corpus of data for a patient. The corpus of data may represent unstructured data. The corpus of data may include a set of strings of characters. The corpus of data may be patient notes in an electronic medical record entered by a physician. In some embodiments, an application programming interface (API) may be used to interface with an electronic medical record system used by the physician. The API may retrieve one or more EMRs of the patient and extract the patient notes. The artificial intelligence engine may include the one or more machine learning models trained to generate cognified data based on unstructured data.

At block 2104, the processing device may identify indicia. The indicia may be identified by processing the strings of characters. The indicia may include a phrase, a predicate, a subject, an object (e.g., direct, indirect), a keyword, a cardinal, a number, a concept, an objective, a noun, a verb, or some combination thereof.

At block 2106, the processing device may compare the indicia to a knowledge graph representing known health related information to generate a possible health related information pertaining to the patient. In some embodiments, the indicia may be compared to numerous knowledge graphs each representing a different medical conditions. As discussed herein, the knowledge graphs may include respective nodes that include different known health related information about the medical conditions, and a logical structure that includes predicates that correlate the information in the respective knowledge graphs. The knowledge graphs and the logical structures may be generated by the one or more trained machine learning models using the known health related information. The knowledge graph may represent knowledge of a disease and the knowledge graph may include a set of concepts pertaining to the disease obtained from the known health related information and also includes relationships between the set of concepts. The known health related information associated with the nodes may be facts, concepts, complications, risks, causal effects, etc. pertaining to the medical conditions (e.g., diseases) represented by the knowledge graphs. The processing device may codify evidence-based health related guidelines pertaining to the diseases to generate the logical structures. The generated possible health related information may be a tag that is associated with the indicia in the unstructured data.

At block 2108, the processing device may identify, using the logical structure, a structural similarity of the possible health related information and a known predicate in the logical structure. The structural similarity may be used to identify a certain pattern. The pattern may pertain to treatment, quality of care, risk adjustment, orders, referral, education and content patterns, and the like. The structural similarity and/or the pattern may be used to cognify the corpus of data.

At block 2110, the processing device may generate, by the artificial intelligence engine, cognified data based on the structural similarity. In some embodiments, the cognified data may include a health related summary of the possible health related information. The health related summary may include conclusions, concepts, recommendations, identified gaps in the treatment plan, identified gaps in risk analysis, identified gaps in quality of care, and so forth pertaining to one or more medical conditions represented by one or more knowledge graphs that include the logic structure having the known predicate that is structurally similar to the possible health related information.

In some embodiments, generating the cognified data may include generating at least one new string of characters representing a statement pertaining to the possible health related information. Also, the artificial intelligence engine executed by the processing device may include the at least one new string of characters in the health related summary of the possible health related information. The statement may include a concept, conclusion, and/or recommendation pertaining to the possible health related information. The statement may describe an effect that results from the possible health related information.

Figure 22:
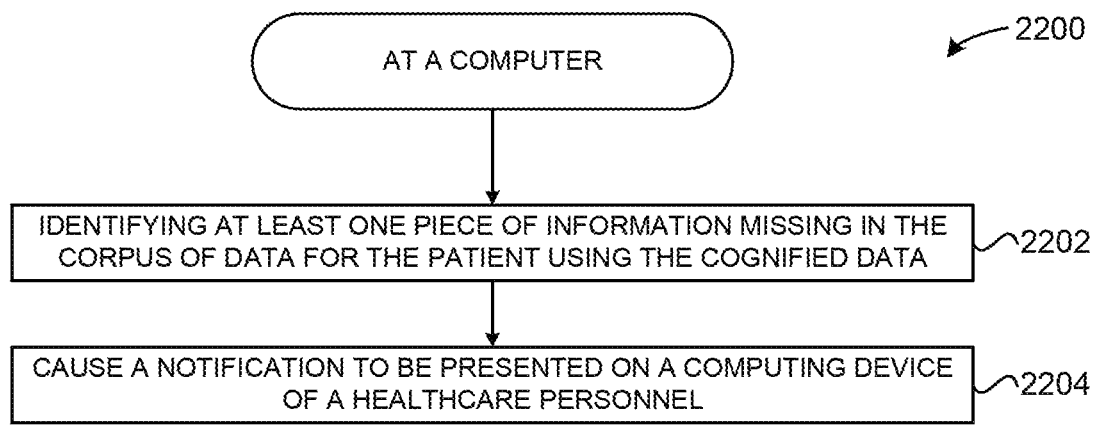
FIG. 22 shows a method for identifying missing information in a corpus of data, in accordance with various embodiments.

FIG. 22 shows a method 2200 for identifying missing information in a corpus of data, in accordance with various embodiments. In some embodiments, the method 2300 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2200 may include operations that are implemented in computer instructions stored in a memory and executed by a processor of a computing device.

At block 2202, the processing device executing the artificial intelligence engine may identify at least one piece of information missing in the corpus of data for the patient using the cognified data. The at least one piece of information pertains to a treatment gap, a risk, gap, a quality of care gap, or some combination thereof.

At block 2204, the processing device may cause a notification to be presented on a computing device of a healthcare personnel (e.g., physician). The notification may instruct entry of the at least one piece of information into the corpus of data (e.g., patient notes in the EMR). For example, if certain symptoms are described for a patient in the corpus of data and those symptoms are known to result from a certain medication currently prescribed to the patient, but the corpus of data does not indicate switching medications, then the at least one piece of information may identify a treatment gap and recommend switching medications to one that does not cause those symptoms.

Figure 23:
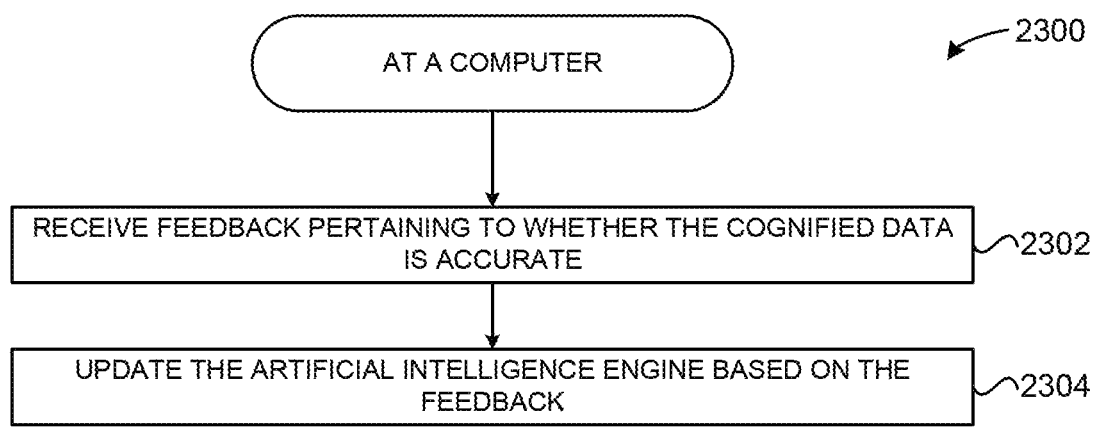
FIG. 23 shows a method for using feedback pertaining to the accuracy of cognified data to update an artificial intelligence engine, in accordance with various embodiments.

FIG. 23 shows a method 2300 for using feedback pertaining to the accuracy of cognified data to update an artificial intelligence engine, in accordance with various embodiments. In some embodiments, the method 2300 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2300 may include operations that are implemented in computer instructions stored in a memory and executed by a processor of a computing device.

At block 2302, the processing device may receive feedback pertaining to whether the cognified data is accurate. For example, the physician may be presented with the cognified data on a computing device, and the physician may review the cognified data. The physician may be presented with options to verify the accuracy of portions or all of the cognified data for the particular patient. For example, the physician may select a first graphical element (e.g., button, checkbox, etc.) next to portions of the cognified data that are accurate and may select a second graphical element next to portions of the cognified data that are inaccurate. If the second graphical element is selected, an input box may appear and a notification may be presented to provide a reason why the portion is inaccurate and to provide corrected information. The feedback may be transmitted to the cognitive intelligence platform.

At block 2304, the processing device may update the artificial intelligence engine based on the feedback. A closed-loop feedback system may be implemented using these techniques. The feedback may enhance the accuracy of the cognified data as the artificial intelligence engine continues to learn and improve.

Figure 24A:
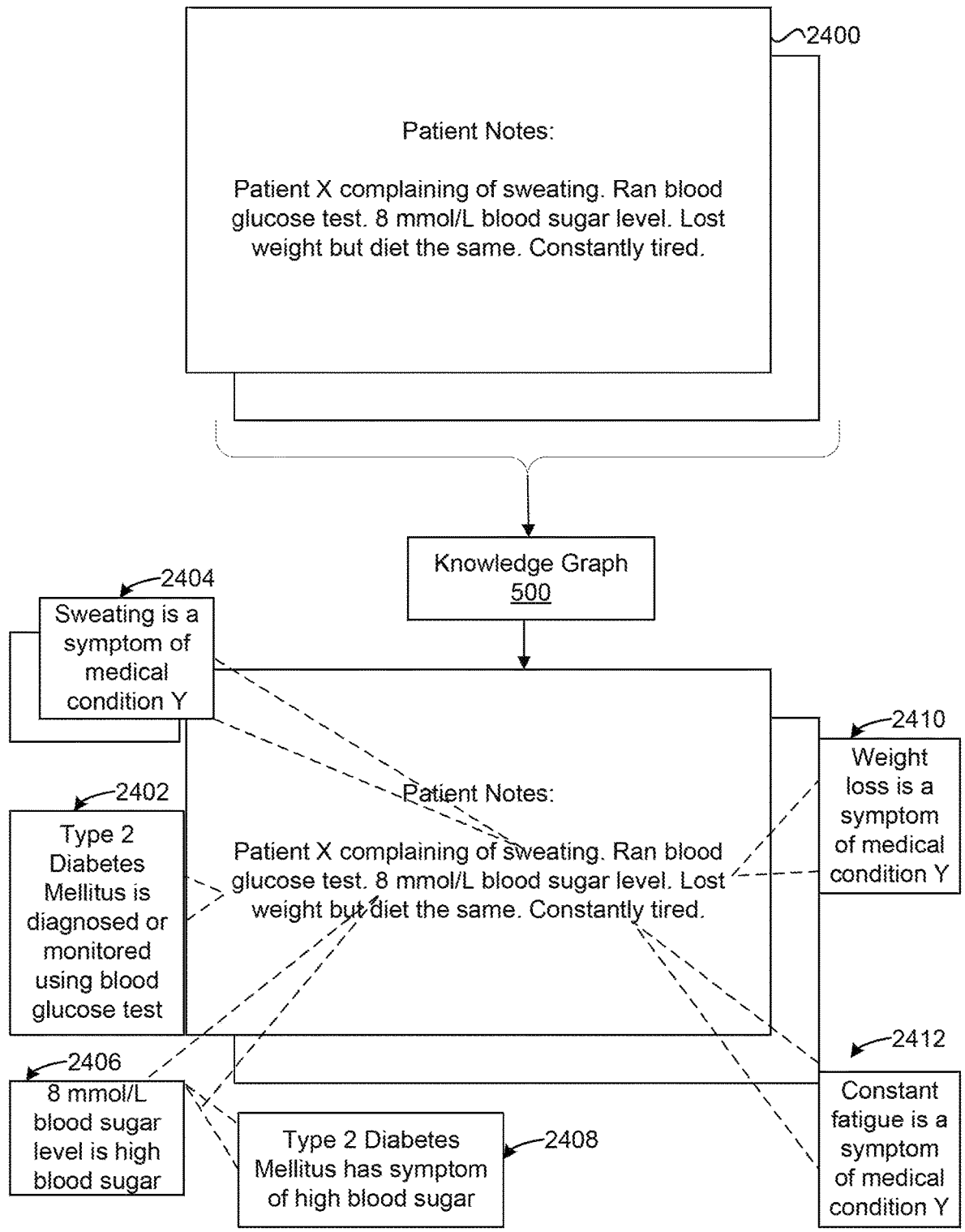
FIG. 24A shows a block diagram for using a knowledge graph to generate possible health related information, in accordance with various embodiments.

FIG. 24A shows a block diagram for using the knowledge graph 500 to generate possible health related information, in accordance with various embodiments. As depicted, a physician may have entered patient notes 2400 in one or more electronic medical records (EMRs). The EMRs may be provided directly to the cognitive intelligence engine 102 and/or retrieved using an application programming interface (API) from an EMR system used by the physician. The patient notes may be extracted from the EMRs. In some embodiments, numerous patient notes from numerous consultations may be processed, synthesized, and cognified using the disclosed techniques. In some embodiments, patient notes from a single consultation may be processed, synthesized, and cognified using the disclosed techniques. The patient notes may include a set of strings of characters that arranged in sentences, phrases, and/or paragraphs. The cognitive intelligence platform 102 may process the set of strings of characters to identify indicia comprising a phrase, a predicate, a keyword, a subject, an object, a cardinal, a number, a concept, or some combination thereof.

The cognitive intelligence platform 102, and in particular the artificial intelligence engine 109, may compare the indicia to numerous knowledge graphs 500 each representing a respective medical condition, such as diabetes, cancer, coronary artery disease, arthritis, just to name a few examples. The artificial intelligence engine 109 may be trained to generate possible health related information by constructing logical structures based on matched indicia and known health related information (health artifacts that are established based on information from a trusted source) represented in the knowledge graphs 500. The logical structures may be tagged to the indicia, as depicted in FIG. 24A.

The artificial intelligence engine 109 may identify the following example indicia: "Patient X", "sweating", "blood glucose test", "8 mmol/L blood sugar level", "lost weight", "diet the same", "constantly tired". The artificial intelligence engine 109 may match the indicia with known health related information in the knowledge graph 500. For example, in the knowledge graph 500 depicted in FIG. 5, "blood glucose test", is a known health related artifact that is used to test for Type 2 Diabetes Mellitus. Thus, various logical structures may be constructed by the artificial intelligence engine 109 that states "blood glucose test is used to test Type 2 Diabetes Mellitus", "Type 2 Diabetes Mellitus is diagnosed or monitored using blood glucose test" (tag 2402), "blood glucose test measures blood sugar level", and so forth.

The artificial intelligence engine 109 may generate other possible health related information for each of the indicia that matches known health related information in the knowledge graphs. For example, the artificial intelligence engine 109 generated example logical structure "Sweating is a symptom of medical condition Y" (tag 2404) for the indicia "sweating". The artificial intelligence engine 109 may generate other possible health related information for "sweating", such as "sweating is caused by running", "sweating is a symptom of fever". Further, the artificial intelligence engine 109 may elaborate on the generated possible health related information by generating further possible health related information. Based on generating "sweating is a symptom of medical condition Y" (where Y is the name of the medical condition), the artificial intelligence engine 109 may generate another logical structure "medical condition Y causes Z" (where Z is a health artifact such as another medical condition).

It should be understood that, although not shown, a logical structure may be included in the knowledge graph 500 that indicates "Type 2 Diabetes has normal blood sugar level 5-7 mmol/L". An example possible health related information generated by the artificial intelligence engine 109 for the indicia "8 mmol/L blood sugar level" is "8 mmol/L blood sugar level is high blood sugar" (tag 2406) based on comparing the indicia to the known health related information about acceptable blood sugar levels in the knowledge graph 500. The artificial intelligence engine 109 may generate an additional possible health information based on tag 2406, and the additional possible health information may state "Type 2 Diabetes Mellitus has symptom of high blood sugar" (tag 2408).

An example possible health related information generated by the artificial intelligence engine 109 for the indicia "lost weight" may be "Weight loss is a symptom of medical condition Y" (tag 2410) where medical condition Y is any medical condition that causes weight loss. For example, any knowledge graph that includes "weight loss", "loss of weight", or some variant thereof as a health artifact may be identified and one or more possible health related information may be generated indicating that weight loss is a symptom of the medical condition represented by that knowledge graph.

An example possible health related information generated by the artificial intelligence engine 109 for the indicia "constantly tired" may be "Constant fatigue is a symptom of medical condition Y" (tag 2412) where medical condition Y is any medical condition that causes constant fatigue. For example, any knowledge graph that includes "fatigue", "constant fatigue", or some variant thereof as a health artifact may be identified and one or more possible health related information may be generated indicating that constant fatigue is a symptom of the medical condition represented by that knowledge graph.

The knowledge graphs that include a threshold number of matches between the indicia and the known health related matches in the knowledge graphs may be selected for further processing. The threshold may be any suitable number of matches. For example, in the depicted example, the knowledge graph 500 representing Type 2 Diabetes Mellitus may be selected because 3 tags (2402, 2406, and 2408) relate to that medical condition represented in the knowledge graph 500.

Figure 24B:
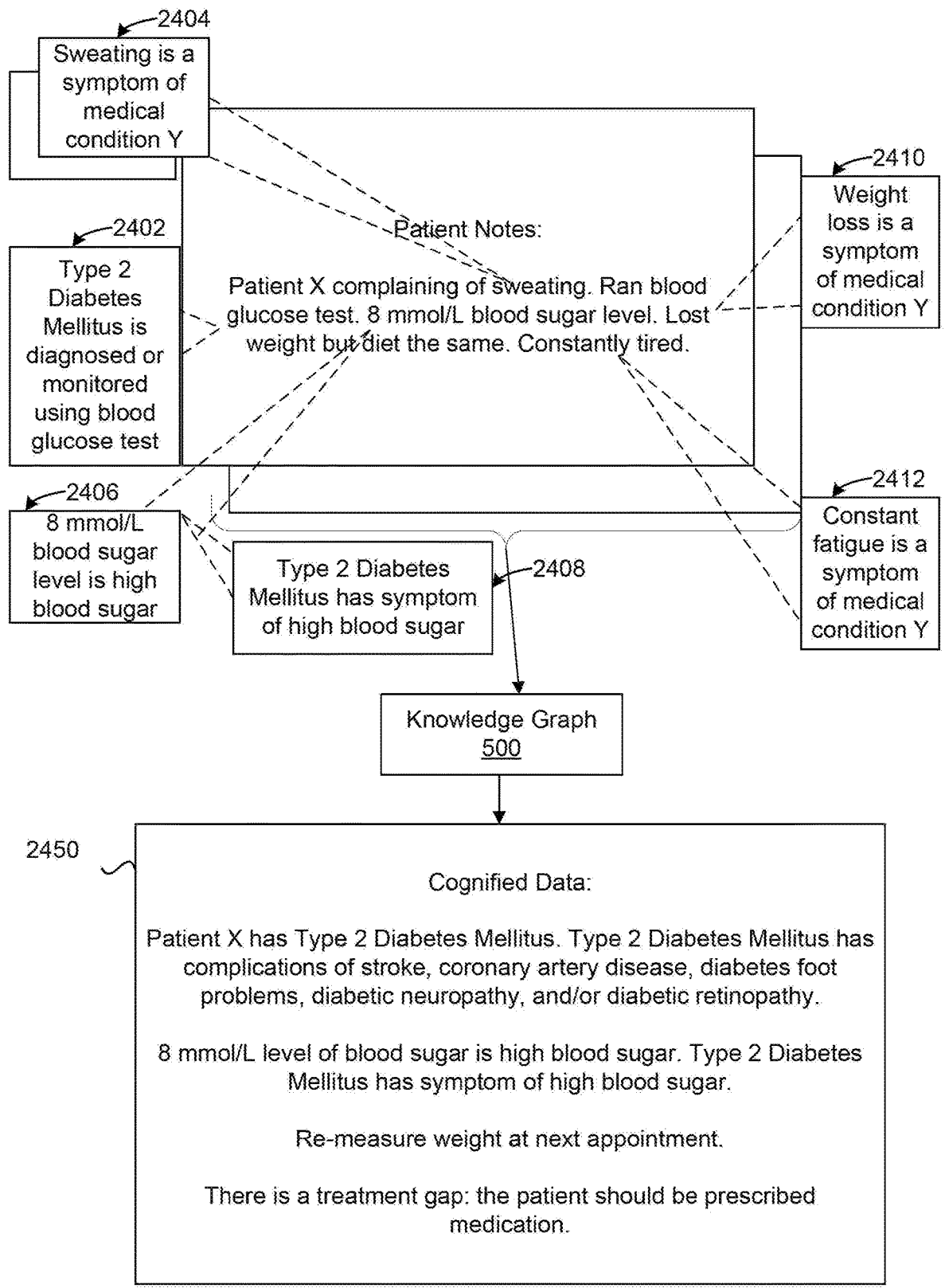
FIG. 24B shows a block diagram for using a logical structure to identify structural similarities with known predicates to generate cognified data, in accordance with various embodiments.

FIG. 24B shows a block diagram for using a logical structure to identify structural similarities with known predicates to generate cognified data, in accordance with various embodiments. The identification of structural similarities may be performed in parallel with the comparison of the indicia with the known health related information. In some embodiments, the generated possible health related information may be compared with the known predicates in the logical structures of the knowledge graphs. In some embodiments, predicates detected in the unstructured data may also be compared with the known predicates in the logical structures of the knowledge graphs. The artificial intelligence engine 500 may identify structural similarities between the possible health related information and the known predicates in the logical structures of the knowledge graphs. The artificial intelligence engine 500 may identify structural similarities between the detected predicates in the unstructured data and the known predicates in the logical structures of the knowledge graphs. In some embodiments, identifying structural similarities may refer to comparing the structure of the logical structure of the possible health related information to a known logical structure (known logical structure may refer to a logical structure established based on a trusted source), such as determining whether the subjects are the same or substantially similar, the predicates are the same or substantially similar, the objects are the same or substantially similar, and so forth.

For example, the knowledge graph 500 includes the logical structure "Type 2 Diabetes Mellitus has symptom high blood sugar". Comparing the possible health related information represented by tag 2408 "Type 2 Diabetes Mellitus has symptom of high blood sugar" to the known logical structure in the knowledge graph 500 results in identifying a structurally similarity between the two. Accordingly, the knowledge graph 500 may be selected for further processing.

In some embodiments, the structural similarities detected may be used to identify patterns. For example, a treatment pattern for diabetes may be detected if a blood glucose test is used, a patient is prescribed a certain medication, and the like. In some embodiments, gaps in the unstructured data may be identified based on the patterns detected. For example, if a person is determined to have a certain medical condition based on the treatment pattern identified, and it is known based on evidence-based guidelines that a certain medication should be prescribed for that treatment pattern, the artificial intelligence engine 109 may indicate there is a treatment gap if that medication has not been prescribed yet.

The knowledge graphs selected when comparing the indicia to the known health related information and the knowledge graphs selected when identifying structural similarities between the known logical structure and the possible health related information may be compared to determine whether there are overlaps. As discussed above, the knowledge graph 500 representing Type 2 Diabetes Mellitus overlaps as being selected during both operations. As a result, the knowledge graph 500 may be used for cognification. In some embodiments, any of the knowledge graphs selected during either operation may be used for cognification.

In some embodiments, the selected knowledge graphs may be used to generate cognified data 2450. Further, the possible health related information and the matching logical structures may be used to generate the cognified data 2450. The cognified data 2450 may include a health related summary of the possible health related information. In some embodiments, the cognified data 2450 may include conclusions, statements of facts, concepts, recommendations, identified gaps in the unstructured data that was processed, and the like.

In some embodiments, the cognified data 2450 may be used to generate a diagnosis of a medical condition for a patient. For example, if there are a threshold number of identified structural similarities between the known logical structures and the possible health related information and/or if there are a threshold number of matches between indicia and known health related information for a particular medical condition, a diagnosis may be generated for that particular medical condition. If there are numerous medical conditions identified after performing the cognification, the numerous medical conditions may be indicated as potential candidates for diagnosis. In the ongoing example, the knowledge graph 500 was selected as the overlapping knowledge graph and satisfies the threshold number of identified structural similarities and/or the threshold number of matches. Accordingly, a diagnosis that Patient X has Type 2 Diabetes Mellitus may be generated. The cognified data 2450 may include the diagnosis, as depicted.

When generating the cognified data, other health related information in the selected knowledge graph 500 that was not included in the unstructured data may be inserted. That is, sentences may be constructed using the known health related information and the predicates in the knowledge graph 50. For example, the unstructured data did not indicate any information pertaining to complications of Type 2 Diabetes Mellitus. However, as depicted in the knowledge graph 500 of FIG. 5, there is a logical structure that specifies "Type 2 Diabetes Mellitus has complications of stroke, coronary artery disease, diabetes foot problems, diabetic neuropathy, and/or diabetic retinopathy". As depicted, this construction of the logical structure is included in the cognified data 2450 by the artificial intelligence engine 109.

The cognified data 2450 may also include the tag 2406 ("8 mmol/L level of blood sugar is high blood sugar. Type 2 Diabetes Mellitus has symptom of high blood sugar") that was generated for the unstructured data based on the known health information in the knowledge graph 500. The artificial intelligence engine 109 may generate a recommendation based on the lost weight indicia indicated in the unstructured data. The recommendation may state "Re-measure weight at next appointment." In addition, as discussed above, the artificial intelligence engine 109 may identify certain gaps. For example, the diagnosis that is generated indicates that the patient has Type 2 Diabetes Mellitus. The unstructured data does not indicate that medication is prescribed. However, the knowledge graph 500 specifies that Type 2 Diabetes Mellitus is treated by "Diabetes Medicines". Accordingly, a treatment gap may be identified by the artificial intelligence engine 109 based on treatment patterns codified in the knowledge graph 500, and a statement may be constructed and inserted in the cognified data 2450. The statement may state "There is a treatment gap: the patient should be prescribed medication."

The cognified data 2450 may be transmitted by the cognitive intelligence platform 102 to a computing device of the service provider 112, such as the physician who entered the unstructured data. As depicted, the cognified data 2450 may be instilled with intelligence, knowledge, and logic using the disclosed cognification techniques. The physician may quickly review the cognified data 2450 without having to review numerous patient notes from various EMRs. In some embodiments, the physician may be presented with options to verify portions or all of the cognified data 2450 is accurate. The feedback may be transmitted to the cognitive intelligence platform 102 and the artificial intelligence engine 109 may update its various machine learning models using the feedback.

Figure 25:
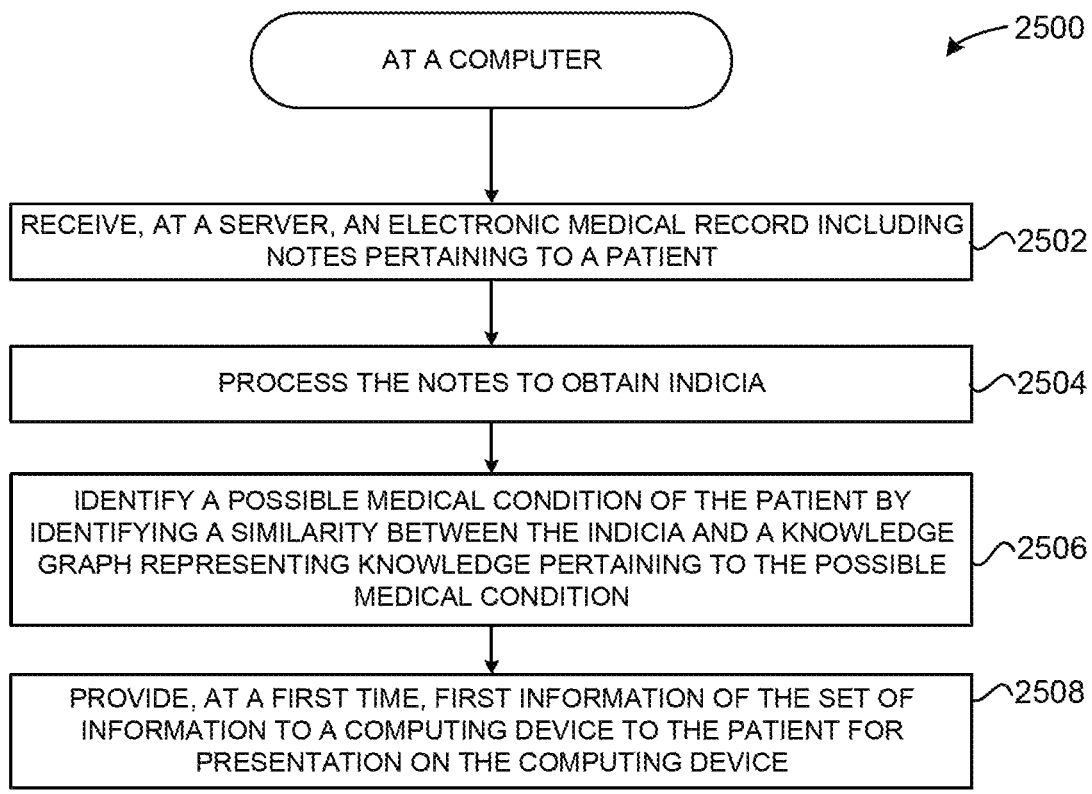
FIG. 25 shows a method for providing first information pertaining to a possible medical condition of a patient to a computing device, in accordance with various embodiments.

FIG. 25 shows a method 2500 for providing first information pertaining to a possible medical condition of a patient to a computing device, in accordance with various embodiments. In some embodiments, the method 2500 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2500 may include operations that are implemented in computer instructions stored in a memory and executed by a processor of a computing device.

At block 2502, the processing device of a server may receive an electronic medical record (EMR) including notes pertaining to a patient. The EMR may be transmitted directly to the server from a computing device of the physician that entered the notes, and/or the EMR may be obtained using an application programming interface (API) interfacing with an EMR system used by the physician that entered the notes. In some embodiments, the server may receive text input by the patient. For example, the text input by the user may include symptoms the patient is experiencing and ask a question pertaining to what medical condition the patient may have. The operations of method 2500 may be used to similarly provide information to the patient based on identifying the possible medical condition using the cognification techniques.

At block 2504, the processing device may process the notes to obtain indicia including a subject, an object, a word, a cardinal, a phrase, a concept, a sentence, a predicate, or some combination thereof. Textual analysis may be performed to extract the indicia. Processing the patient notes to obtain the indicia may further include inputting the notes into an artificial intelligence engine 109 trained to identify the indicia in text based on commonly used indicia pertaining to the possible medical condition. The artificial intelligence engine 109 may determine commonly used indicia for various medical conditions based on evidence-based guidelines, clinical trial results, physician research, or the like that are input to one or more machine learning models.

At block 2506, the processing device may identify a possible medical condition of the patient by identifying a similarity between the indicia and a knowledge graph representing knowledge pertaining to the possible medical condition. The knowledge graph may include a set of nodes representing the set of information pertaining to the possible medical condition. The set of nodes may also include relationships (e.g., predicates) between the set of information pertaining to the possible medication condition. In some embodiments, identifying the possible medical condition may include using a cognified data structure generated from the notes of the patient. The cognified data structure may include a conclusion based on a logic structure representing evidence-based guidelines pertaining to the possible medical condition.

In some embodiments, the similarity may pertain to a match between the indicia and a health artifact (known health related information) included in the knowledge graph 500. For example, "high blood pressure" may be extracted as indicia from the sentence "Patient X has high blood pressure", and "high blood pressure" is a health artifact at a node in the knowledge graph 500 representing Type 2 Diabetes Mellitus.

In some embodiments, the similarity may pertain to a structural similarity between the logical structure (e.g., "Type 2 Diabetes has symptoms of High Blood Pressure) and the indicia (e.g., "Patient X has symptoms of High Blood Pressure") that is included in the unstructured data. If the subject, predicates, and/or objects of the logical structure and the indicia match or substantially match (e.g., "has symptoms of High Blood Pressure" match between the logical structure and the indicia, also "Type 2 Diabetes has symptoms of High Blood Pressure" and "Patient X has symptoms of High Blood Pressure" substantially match), then the knowledge graph 500 including the logical structure is a candidate for a possible medical condition. In some embodiments, a combination of similarities identified between the match between the indicia and the health artifact and between the logical structure and the indicia may be used to identify a possible medical condition and/or cognify the unstructured data.

An artificial intelligence engine 109 may be used to identify the possible medical condition by identifying the similarity between the indicia and the knowledge graph. The artificial intelligence engine 109 may be trained using feedback from medical personnel. The feedback may pertain to whether output regarding the possible medical conditions from the artificial intelligence engine 109 are accurate for input including notes of patients.

At block 2508, the processing device may provide, at a first time, first information of the set of information to a computing device of the patient for presentation of the computing device, the first information being associated with a root node of the set of nodes. In some embodiments, the first information may pertain to a name of the possible medical condition. As depicted in the knowledge graph 500 of FIG. 5, the root node is associated with the name of the medical condition "Type 2 Diabetes Mellitus". In some embodiments, the first information may pertain to a definition of the possible medical condition, instead of or in addition to the name of the possible medical condition.

Figure 26:
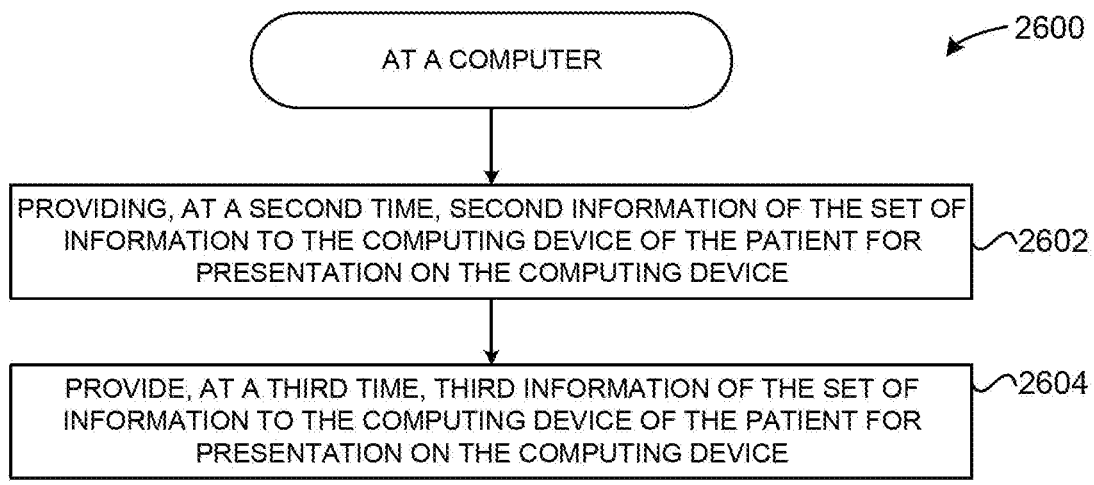
FIG. 26 shows a method for providing second and third information pertaining to a possible medical condition of a patient to a computing device, in accordance with various embodiments.

FIG. 26 shows a method 2600 for providing second and third information pertaining to a possible medical condition of a patient to a computing device, in accordance with various embodiments. In some embodiments, the method 2600 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2600 may include operations that are implemented in computer instructions stored in a memory and executed by a processor of a computing device.

At block 2602, the processing device may provide, at a second time, second information of the set of information to the computing device of the patient for presentation on the computing device. The second information may be associated with a second node of the set of nodes, and the second time may be after the first time. The second information may be different than the first information. The second information may pertain to how the possible medical condition affects people, signs and symptoms of the possible medical condition, a way to treat the possible medical condition, a progression of the possible medical condition, complications of the possible medical condition, or some combination thereof. The second time may be selected based on when the second information is relevant to a stage of the possible medical condition. The second time may be preconfigured based on an amount of time elapsed since the first time.

At block 2604, the processing device may provide, at a third time, third information of the set of information to the computing device of the patient for presentation on the computing device of the patient. The third information may be associated with a third node of the set of nodes, and the third time may be after the second time. The third information may be different than the first information and the second information. The third information may pertain to how the possible medical condition affects people, signs and symptoms of the possible medical condition, a way to treat the possible medical condition, a progression of the possible medical condition, complications of the possible medical condition, or some combination thereof. The third time may be selected based on when the third information is relevant to a stage of the possible medical condition. The third time may be preconfigured based on an amount of time elapsed since the second time.

This process may continue until each node of the knowledge graph 500 are traversed to provide relevant information to the patient at relevant times until all information associated with the set of nodes has been delivered to the computing device of the patient. In this way, the patient may not be overwhelmed with a massive amount of information at once. Further, memory resources of the computing device of the patient may be saved by regulating the amount of information that is provided.

Figure 27:
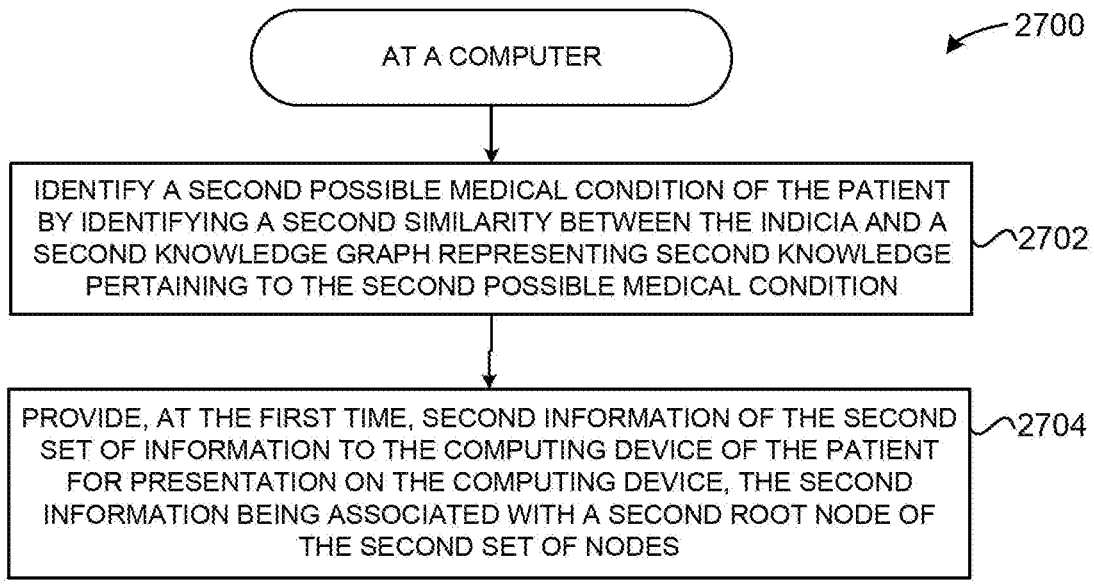
FIG. 27 shows a method for providing second information pertaining to a second possible medical condition of the patient, in accordance with various embodiments.

FIG. 27 shows a method 2700 for providing second information pertaining to a second possible medical condition of the patient, in accordance with various embodiments. In some embodiments, the method 2700 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 2700 may include operations that are implemented in computer instructions stored in a memory and executed by a processor of a computing device.

At block 2702, the processing device may identify a second possible medical condition of the patient by identifying a second similarity between the indicia and a second knowledge graph representing second knowledge pertaining to the second possible medical condition. In some embodiments, the second similarity may pertain to a match between the indicia and a health artifact (known health related information) included in the second knowledge graph. For example, "vomiting" may be extracted as indicia from the sentence "patient has symptom of vomiting", and "vomiting" is a health artifact at a node in the second knowledge graph representing the flu. In some embodiments, the second similarity may pertain to a second structural similarity between a second logical structure (e.g., "Flu has symptom of vomiting) and the possible health information (e.g., "has symptom of vomiting") that is included in the unstructured data. In some embodiments a combination of the similarities between the indicia and the health artifact and between the logical structure and the possible health information may be used to identify the second possible medical condition and/or cognify the unstructured data.

At block 2704, the processing device may provide, at the first time, second information of the second set of information to the computing device of the patient for presentation on the computing device, the second information being associated with a second root node of the second set of nodes. The second information may be provided with the first information at the first time. In some embodiments, a user interface on the computing device of the patient may present the first information and the second information concurrently on the same screen. For example, the user interface may present that the possible medical conditions include "Type 2 Diabetes Mellitus" and the "flu". It should be understood that any suitable number of possible medical conditions may be identified using the cognification techniques and the information related to those medical conditions may be provided to the computing device of the patient on a regulated basis.

In some embodiments, the patient may be presented with options to indicate whether the information provided at the various times was helpful. The feedback may be provided to the artificial intelligence engine 109 to update one or more machine learning models to improve the information that is provided to the patients.

Figure 28:
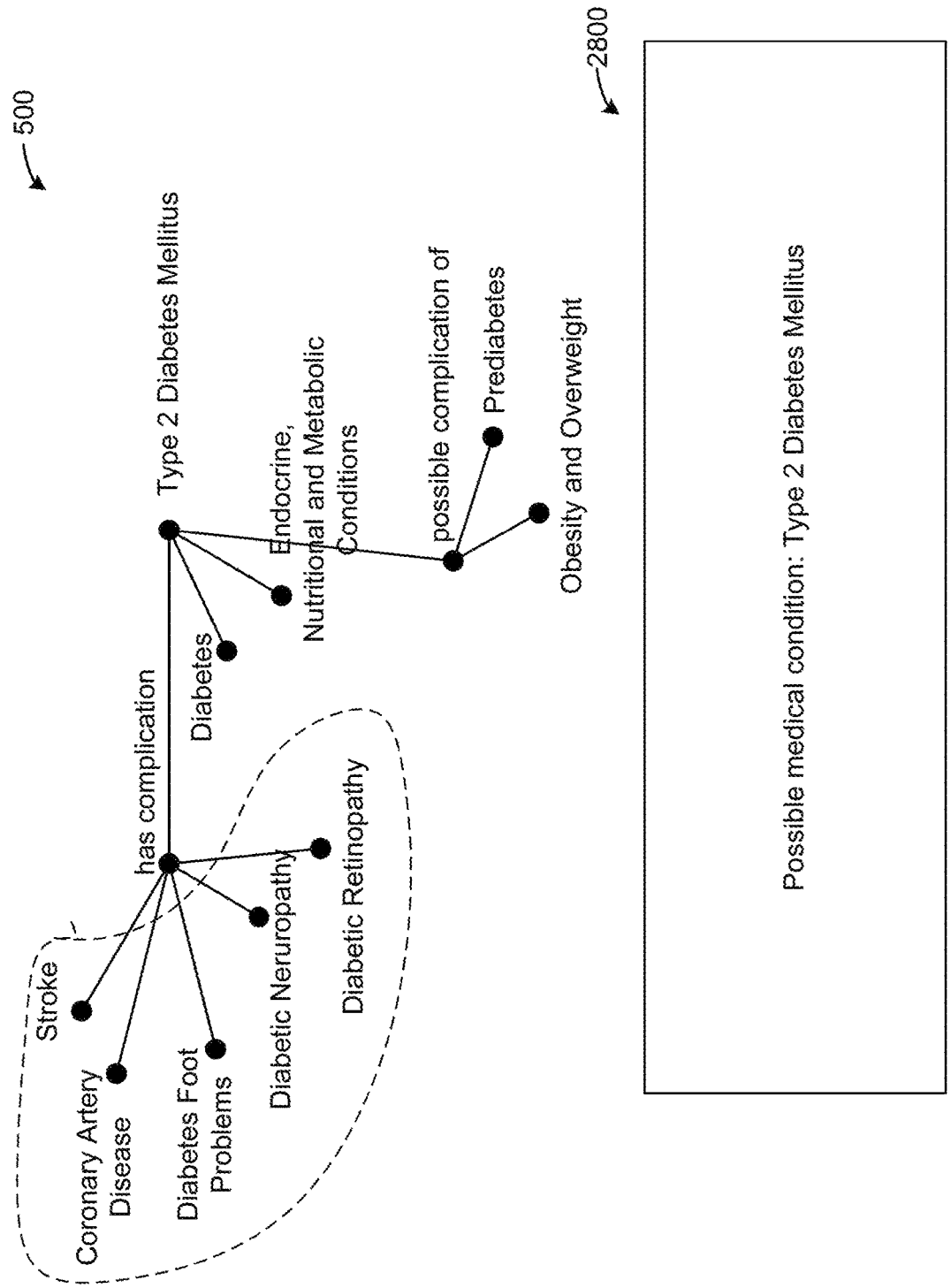
FIG. 28 shows an example of providing first information of a knowledge graph representing a possible medical condition, in accordance with various embodiments.

FIG. 28 shows an example of providing first information of a knowledge graph 500 representing a possible medical condition, in accordance with various embodiments. In the depicted example, just a portion of the knowledge graph 500 representing Type 2 Diabetes Mellitus is depicted. Based on the patient notes entered by the physician and/or the text input by the patient, the artificial intelligence engine 109 may extract indicia. Using the indicia, the artificial intelligence engine 109 may identify a possible medical condition of the patient by identifying at least one similarity between the indicia and the knowledge graph 500. It should be understood that the artificial intelligence engine 109 identified Type 2 Diabetes Mellitus as the possible medical condition based on the similarity between the indicia and the knowledge graph 500 using the cognification techniques described herein.

Accordingly, at a first time, the cognitive intelligence platform 102 may provide first information associated with the root node of the knowledge graph 500. The root node may be associated with the name "Type 2 Diabetes Mellitus" of the medical condition. A user interface 2800 of the computing device of the patient may present the first information "Possible medical condition: Type 2 Diabetes Mellitus" at the first time.

Figure 29:
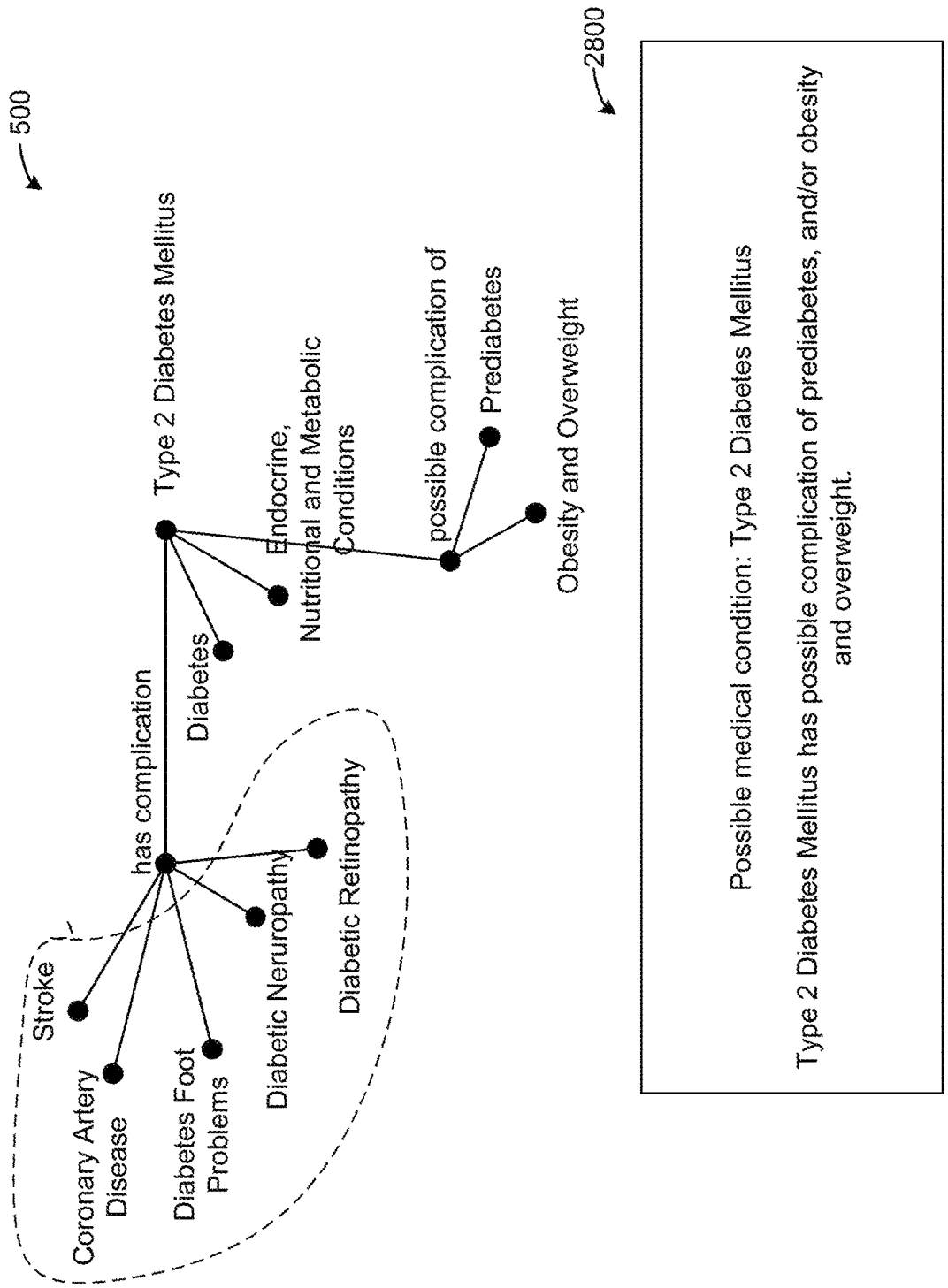
FIG. 29 shows an example of providing second information of the knowledge graph representing the possible medical condition, in accordance with various embodiments.

FIG. 29 shows an example of providing second information of the knowledge graph 500 representing the possible medical condition, in accordance with various embodiments. The second information may be provided at a second time subsequent to the first time the first information was provided. The second information may be associated with at least a second node representing a health artifact of the knowledge graph 500. The second information may be different than the first information. The second information may combine a predicate of a node that connects the second node representing the health artifact to the root node. For example, the second information may include "Type 2 Diabetes Mellitus has possible complication of prediabetes, or obesity and overweight." The second information may be presented on the user interface 2800 with the first information, as depicted. In some embodiments, just the second information may be presented on the user interface 2800 and the first information may be deleted from the user interface 2800.

Figure 30:
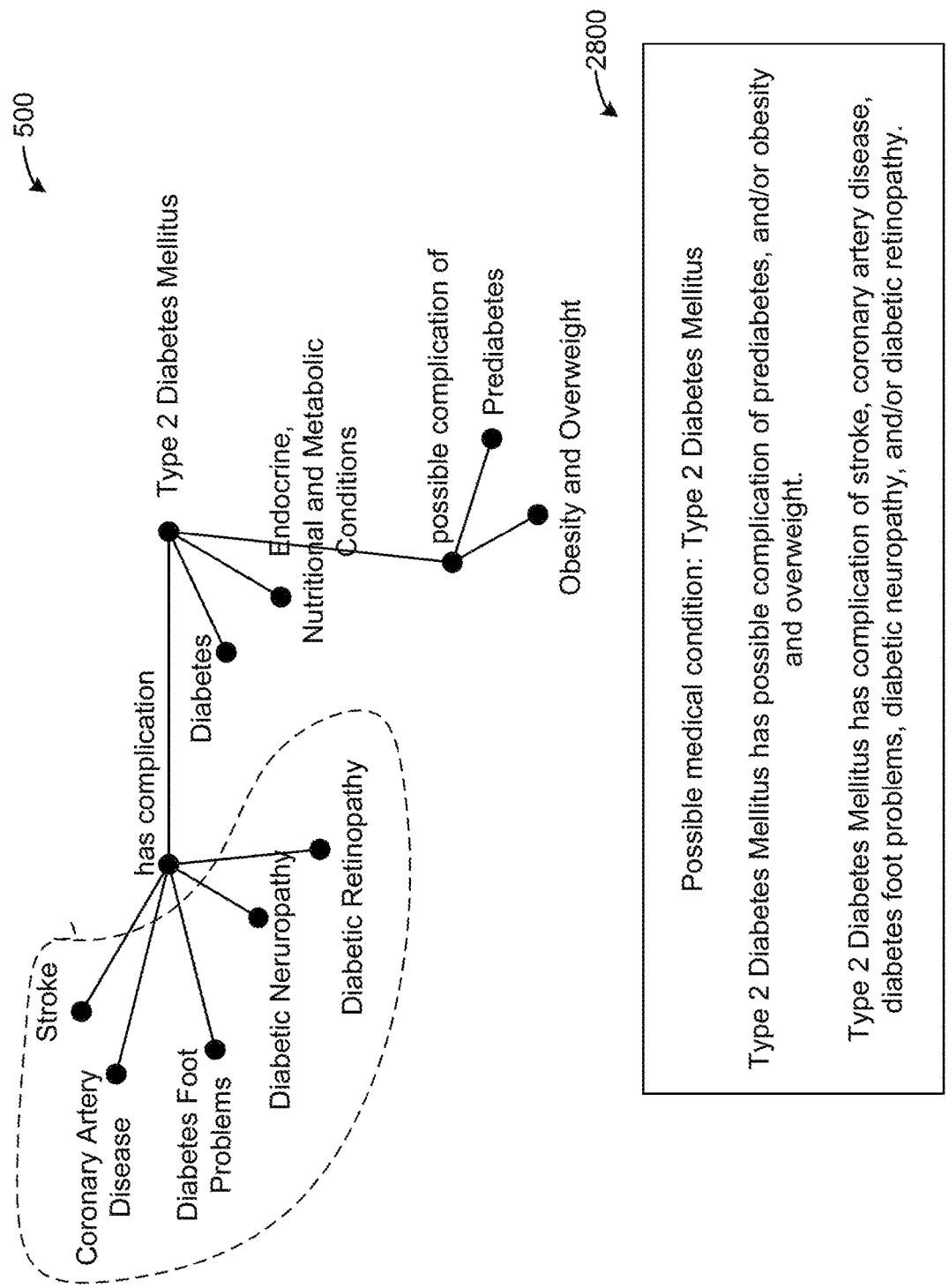
FIG. 30 shows an example of providing third information of the knowledge graph representing the possible medical condition, in accordance with various embodiments.

FIG. 30 shows an example of providing third information of the knowledge graph representing the possible medical condition, in accordance with various embodiments. The third information may be provided at a third time subsequent to the second time the second information was provided. The third information may be associated with at least a third node representing a health artifact of the knowledge graph 500. The third information may be different than the first information and the second information. The third information may combine a predicate of a node that connects the third node representing the health artifact to the root node. For example, the third information may include "Type 2 Diabetes Mellitus has complication of stroke, coronary artery disease, diabetes foot problems, diabetic neuropathy, and/or diabetic retinopathy." The third information may be presented on the user interface 2800 with the first information and/or the second information, as depicted. In some embodiments, just the third information may be presented on the user interface 2800, and the first information and the second information may be deleted from the user interface 2800. In some embodiments, any combination of the first, second, and third information may be presented on the user interface 2800.

In some embodiments, the various health artifacts represented by each node in the knowledge graph 500 may be provided to the computing device of the patient until all of the information in the knowledge graph 500 is provided. Additionally, if the knowledge graph 500 contains a link to another knowledge graph representing a related medical condition, the information included in that other knowledge graph may be provided to the patient. At any time, the patient may request to stop receiving information about the possible medical condition and no additional information will be provided. If the patient desires additional information faster, the patient may be presented with an option to obtain the next set of information at any time.

Figure 31:
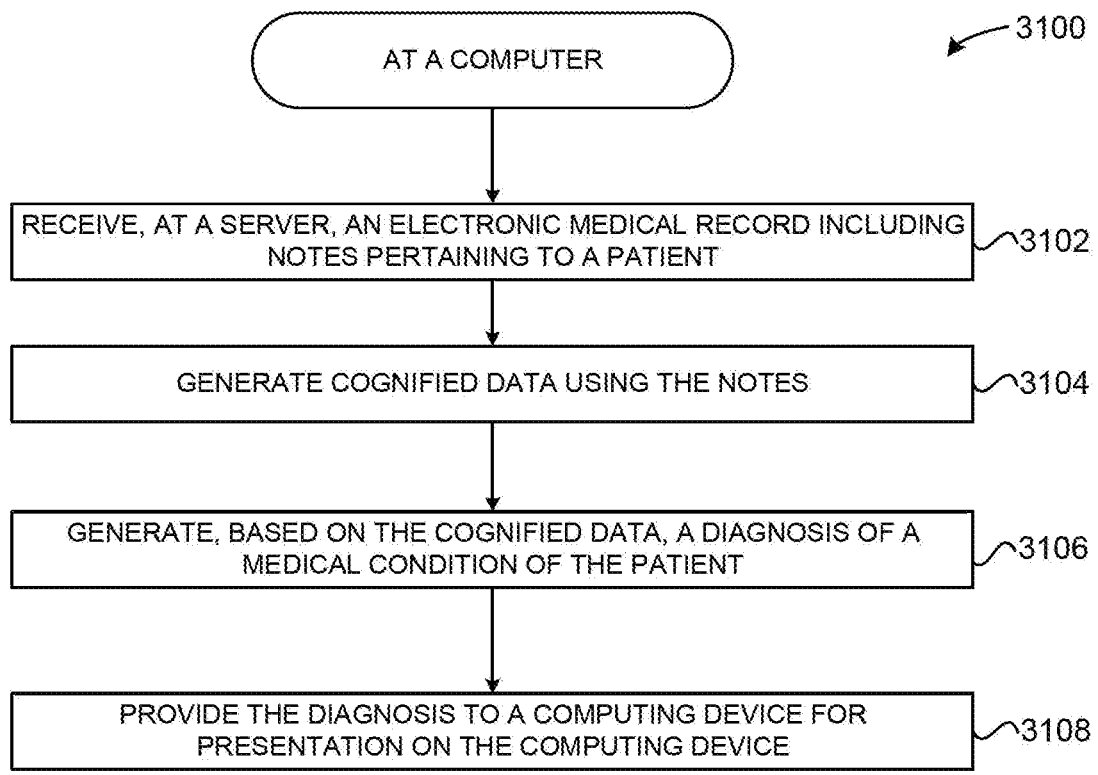
FIG. 31 shows a method for using cognified data to diagnose a patient, in accordance with various embodiments.

FIG. 31 shows a method 3100 for using cognified data to diagnose a patient, in accordance with various embodiments. In some embodiments, the method 3100 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 3100 may include operations that are implemented in computer instructions stored in a memory and executed by a processor of a computing device.

At block 3102, the processing device of a server may receive an electronic medical record including notes pertaining to a patient. The notes may include strings of characters arranged in sentences and/or paragraphs. The processing device may process the strings of characters and identify, in the notes, indicia including a phrase, a predicate, a subject, an object, a cardinal, a number, a concept, or some combination thereof. In some embodiments, the notes may be processed to obtain the indicia by inputting the notes into the artificial intelligence engine 109 trained to identify the indicia in text based on commonly used indicia pertaining to the medical condition.

At block 3104, the processing device may generate cognified data using the notes. The cognified data may include a health summary of a medical condition. Generating the cognified data may further include detecting the medical condition by identifying a similarity between the indicia and a knowledge graph. For example, in some embodiments, the similarity may pertain to a match between the indicia and a health artifact (known health related information) included in the knowledge graph 500. For example, "high blood pressure" may be extracted as indicia from the sentence "Patient X has high blood pressure", and "high blood pressure" is a health artifact at a node in the knowledge graph 500 representing Type 2 Diabetes Mellitus. In some embodiments, the similarity may pertain to a structural similarity between the logical structure (e.g., "Type 2 Diabetes has symptoms of High Blood Pressure) and possible health related information generated using the identified indicia or subjects, predicates, and/or objects (e.g., "Patient X has symptoms of High Blood Pressure") that is included in the unstructured data. In some embodiments, a combination of similarities between the indicia and the health artifact, and between the logical structure and the indicia/possible health related information may be used to detect the medical condition.

At block 3106, the processing device may generate, based on the cognified data, a diagnosis of the medical condition of the patient. The diagnosis may at least identify a type of the medical condition that is detected using the cognified data. The diagnosis may be generated if a threshold number of matches between the indicia and health artifacts in the knowledge graph are identified, and/or if a threshold number of structural similarities are identified between logical structures of the knowledge graph and indicia/possible health information generated for the unstructured data. For example, the threshold numbers may be configurable and set based on a confidence level that the health artifacts that match the indicia and/or the logical structures that are similar to the indicia/possible health related information are correlated with the particular medical condition. The threshold numbers may be based on information from trusted sources, such as physicians having medical licenses.

In some embodiments, the processing device may use an artificial intelligence engine 109 that is trained using feedback from medical personnel. The feedback may pertain to whether output regarding diagnoses from the artificial intelligence engine 109 are accurate for input including notes of patients. The cognified data may include a conclusion that is identified based on a logical structure in the knowledge graph 500, where the logical structure represents codified evidence-based guidelines pertaining to the medical condition.

At block 3108, the processing device may provide the diagnosis to a computing device of a patient and/or a physician for presentation on the computing device. The diagnosis may be included in the cognified data. The physician may review the diagnosis and may provide feedback via graphical element(s) whether the diagnosis is accurate. The feedback may be received by the artificial intelligence engine 109 and used to update the one or more machine learning models used by the artificial intelligence engine 109 to cognify data and generate diagnoses.

Figure 32:
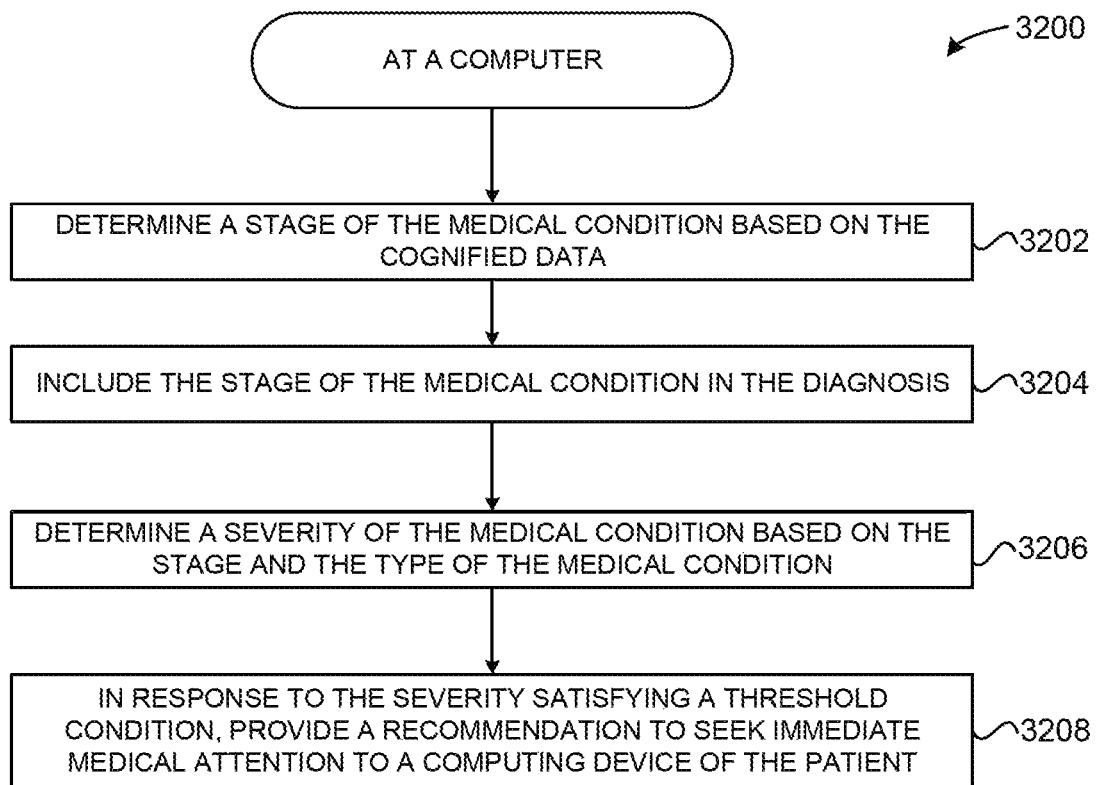
FIG. 32 shows a method for determining a severity of a medical condition based on a stage and a type of the medical condition, in accordance with various embodiments.

FIG. 32 shows a method 3200 for determining a severity of a medical condition based on a stage and a type of the medical condition, in accordance with various embodiments. In some embodiments, the method 3200 is implemented on a cognitive intelligence platform. In some embodiments, the cognitive intelligence platform is the cognitive intelligence platform 102 as shown in FIG. 1. In some embodiments, the cognitive intelligence platform is implemented on the computing device 1400 shown in FIG. 14. The method 3200 may include operations that are implemented in computer instructions stored in a memory and executed by a processor of a computing device.

At block 3202, the processing device may determine a stage of the medical condition diagnosed based on the cognified data. The stage of the medical condition may be determined based on information included in the cognified data. For example, the information in the cognified data may be indicative of the particular stage of the medical condition. Such stages may include numerical values (e.g., 1, 2, 3, 4, etc.), descriptive terms (e.g., chronic, acute, etc.), or any suitable representation capable of indicating different progressions in a range (e.g., from low to high, or from mild to severe, etc.).

The artificial intelligence engine 109 may be trained to identify the stage based on the information in the cognified data. For example, if certain symptoms are present, certain blood levels are present, certain vital signs are present, or the like for a particular medical condition, the artificial intelligence engine 109 may determine that the medical condition has reached a certain stage. The artificial intelligence engine 109 may be trained on evidence-based guidelines that correlate the various information with the particular stages. For example, it may be known that a particular stage of cancer involves symptoms such as weight loss, lack of appetite, bone pain, dry cough or shortness of breath, or some combination thereof. If those symptoms are identified for the medical condition diagnosed (cancer) for the patient, then that particular stage may be determined.

At block 3204, the processing device may include the stage of the medical condition in the diagnosis. For example, the processing device may indicate the diagnosis is the "Patient X has stage 4 breast cancer". At block 3206, the processing device may determine a severity of the medical condition based on the stage and the type of the medical condition. If the stage is relatively low and the medical condition is easily treatable, then the severity may be low. If the stage is relatively high (chronic) and the medical condition is difficult to treat (cancer), then the severity may be high.

At block 3208, in response to the severity satisfying a threshold condition, the processing device may provide a recommendation to seek immediate medical attention to a computing device of the patient. The threshold condition may be configurable. In some embodiments, the threshold condition may be set based on information from a trusted source (e.g., evidence-based guidelines, clinical trial results, physician research, and the like).

The various aspects, embodiments, implementations or features of the described embodiments can be used separately or in any combination. Various aspects of the described embodiments can be implemented by software, hardware or a combination of hardware and software. The described embodiments can also be embodied as computer readable code on a computer readable medium. The computer readable medium is any data storage device that can store data which can thereafter be read by a computer system. Examples of the computer readable medium include read-only memory, random-access memory, CD-ROMs, DVDs, magnetic tape, hard disk drives, solid-state drives, and optical data storage devices. The computer readable medium can also be distributed over network-coupled computer systems so that the computer readable code is stored and executed in a distributed fashion.

Consistent with the above disclosure, the examples of systems and method enumerated in the following clauses are specifically contemplated and are intended as a non-limiting set of examples.

Clause 1. A cognitive intelligence platform, comprising:
a first system configured to execute a knowledge cloud, the first system comprising:
a first processor; and
a first memory coupled to the first processor, the first memory storing instructions that cause the knowledge cloud to:
receive inputs from medical facilities; and
receive inputs from service providers;
a second system configured to implement a critical thinking engine, the critical thinking engine communicably coupled to the knowledge cloud, the second system comprising:
a second processor; and
a second memory coupled to the second processor, the second memory storing instructions that cause the critical thinking engine to receive inputs from the knowledge cloud; and
a third system configured to implement a cognitive agent, the cognitive agent communicably coupled to the critical thinking engine and the knowledge cloud, the third system comprising:
a third processor; and
a third memory coupled to the third processor, the third memory storing instructions that cause the cognitive agent to:
receive an originating question from a user related to a subject matter;
execute, using the critical thinking engine, a first round of analysis to generate an answer; and
provide the answer to the user including a recommendation associated with the subject matter.

Clause 2. The cognitive intelligence platform of any preceding clause, wherein the second memory stores instructions that further cause the critical thinking engine to:
receive a first information;
receive a second information that contradicts the first information; and
process the first information and second information.

Clause 3. The cognitive intelligence platform of any preceding clause, wherein the second memory stores instructions that further cause the critical thinking engine to:
parse the originating question;
retrieve data from the knowledge cloud; and
perform a causal analysis of the data in view of the originating question, wherein the causal analysis, in part, informs the answer.

Clause 4. The cognitive intelligence platform of any preceding clause, wherein the second memory stores instructions that further cause the critical thinking engine to:
receive the originating question from the cognitive agent;
assess a first chain of logic associated with the originating question;
assess a second chain of logic associated with the originating question; and
provide the answer to the cognitive agent, wherein the answer is associated with the first chain of logic.

Clause 5. The cognitive intelligence platform of any preceding clause, wherein the third memory stores instructions that further cause the cognitive agent to communicate a logical argument that leads to a conclusion, wherein the conclusion, in part, informs the recommendation associated with the subject matter.

Clause 6. The cognitive intelligence platform of any preceding clause, wherein the third memory stores instructions that further cause the cognitive agent to:
  render for display, to the user, a chain of logic that leads to the conclusion;
  receive, from the user, an adjustment to the chain of logic; and
  affect change in the critical thinking engine.

Clause 7. The cognitive intelligence platform of any preceding clause, wherein the third memory stores instructions that further cause the cognitive agent to:
  render for display a micro survey;
  receive data associated with the micro survey, wherein the data, in part, informs the recommendation associated with the subject matter.

Clause 8. The cognitive intelligence platform of any preceding clause, wherein when the cognitive agent provides the answer to the user, the third memory causes the cognitive agent to integrate data from at least three selected from the group consisting of: a micro survey, a physician's office, common sense knowledge, domain knowledge, an evidence-based medicine guideline, a clinical ontology, and curated medical advice.

Clause 9. A system comprising:
  a knowledge cloud;
  a critical thinking engine, the critical thinking engine communicably coupled to the knowledge cloud; and
  a cognitive agent, the cognitive agent communicably coupled to the critical thinking engine and the knowledge cloud, wherein the cognitive agent is configured to interact with a user using natural language.

Clause 10. The system of any preceding clause, wherein the cognitive agent interacts with the user using at least one selected from the group consisting of: touch-based input, audio input, and typed input.

Clause 11. The system of claim any preceding clause, wherein the critical thinking engine is configured to:
  receive a first information;
  receive a second information that contradicts the first information; and
  process the first information and the second information.

Clause 12. The system of any preceding clause, wherein the cognitive agent is configured to:
  receive an originating question from the user related to a subject matter;
  execute, using the critical thinking engine, a logical reasoning to generate an answer; and
  provide the answer to the user including a recommendation associated with the subject matter.

Clause 13. The system of any preceding clause, wherein the critical thinking engine is configured to:
  parse the originating question;
  retrieve data from the knowledge cloud; and
  perform a causal analysis of the data in view of the originating question, wherein the causal analysis, in part informs the answer.

Clause 14. The system of any preceding clause, wherein the critical thinking engine is configured to:
  receive the originating question from the cognitive agent;
  assess a first chain of logic associated with the originating question;
  assess a second chain of logic associated with the originating question; and
  provide the answer to the cognitive agent, wherein the answer is associated with the first chain of logic.

Clause 15. The system of any preceding clause, wherein the cognitive agent is further configured to render for display a chain of logic that leads to a conclusion, wherein the conclusion, in part, informs the answer.

Clause 16. A computer readable media storing instructions that are executable by a processor to cause a computer to execute operations comprising:
  executing a cognitive intelligence platform that further comprises:
  a knowledge cloud;
  a critical thinking engine communicably coupled to the knowledge cloud; and
  a cognitive agent communicably coupled to the critical thinking engine and the knowledge cloud, wherein the cognitive agent is configured to:
    receive an originating question from a user related to a subject matter;
    execute, using the critical thinking engine, a logical reasoning to generate an answer; and
    provide the answer to the user including a recommendation associated with the subject matter.

Clause 17. The computer-readable media of any preceding clause, wherein the cognitive agent executing within the cognitive intelligence platform is further configured to:
  render for display a micro survey;
  receive data associated with the micro survey, wherein the data, in part, informs the recommendation associated with the subject matter.

Clause 18. The computer-readable media of any preceding clause, wherein the critical thinking engine executing within the cognitive intelligence platform is further configured to:
  receive the originating question from the cognitive agent;
  assess a first chain of logic associated with the originating question to create a first answer;
  assess a second chain of logic associated with the originating question to create a second answer, wherein the first answer contradicts the second answer; and
  provide the first answer to the cognitive agent, wherein the first answer is the answer provided to the user.

Clause 19. The computer-readable media of any preceding clause, wherein the cognitive agent executing within the cognitive intelligence platform is further configured to render for display the first chain of logic to the user.

Clause 20. The computer-readable media of any preceding clause, wherein the cognitive agent executing within the cognitive intelligence platform is further configured to integrate data from at least three selected from the group consisting of: a micro survey, a physician's office, common sense knowledge, domain knowledge, an evidence-based medicine guideline, a clinical ontology, and curated medical advice.

Clause 21. A computer-implemented method for answering a user-generated natural language medical information query based on a diagnostic conversational template, the method comprising:
  receiving a user-generated natural language medical information query at an artificial intelligence-based diagnostic conversation agent from a user interface on a mobile device;
  responsive to content of the user-generated natural language medical information query, selecting a diagnostic fact variable set relevant to generating a medical advice query answer for the user-generated natural language medical information query by classifying the user-generated natural language medical information query into one of a set of domain-directed medical query classifications associated with respective diagnostic fact variable sets;

compiling user-specific medical fact variable values for one or more respective medical fact variables of the diagnostic fact variable set, wherein the compiling user-specific medical fact variable values for one or more respective medical fact variables of the diagnostic fact variable set further comprises:

extracting a first set of user-specific medical fact variable values from a local user medical information profile associated with the user-generated natural language medical information query, and requesting a second set of user-specific medical fact variable values through natural-language questions sent to the user interface on the mobile device; and responsive to the user-specific medical fact variable values, generating a medical advice query answer in response to the user-generated natural language medical information query.

Clause 22. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:

extracting a third set of user-specific medical fact variable values comprising lab result values from the local user medical information profile associated with the user-generated natural language medical information query.

Clause 23. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:

extracting a fourth set of user-specific medical fact variable values from a remote medical data service profile associated with the local user medical information profile.

Clause 24. The computer-implemented method for answering a user-generated natural language medical information query based on a diagnostic conversational template of any preceding clause, wherein the compiling user-specific medical fact variable values for one or more respective medical fact variables of the diagnostic fact variable set further comprises:

extracting a fifth set of user-specific medical fact variable values derived from demographic characterizations provided by a remote data service analysis of the local user medical information profile.

Clause 25. The computer-implemented method for answering a user-generated natural language medical information query based on a diagnostic conversational template of any preceding clause, wherein the generating the medical advice query answer in response to the user-generated natural language medical information query further comprises providing, in addition to text responsive to a medical question presented in the user-generated natural language medical information query, a treatment action-item recommendation responsive to user-specific medical fact variable values and non-responsive to the medical question presented in the user-generated natural language medical information query.

Clause 26. The computer-implemented method for answering a user-generated natural language medical information query based on a diagnostic conversational template of any preceding clause, wherein the generating the medical advice query answer in response to the user-generated natural language medical information query further comprises providing, in addition to text responsive to a medical question presented in the user-generated natural language medical information query, a medical education media resource responsive to the user-specific medical fact variable values and non-responsive to the medical question presented in the user-generated natural language medical information query.

Clause 27. The computer-implemented method for answering a user-generated natural language medical information query based on a diagnostic conversational template of any preceding clause, wherein selecting a diagnostic fact variable set relevant to generating a medical advice query answer for the user-generated natural language medical information query by classifying the user-generated natural language medical information query into one of a set of domain-directed medical query classifications associated with respective diagnostic fact variable set further comprises classifying the user-generated natural language medical information query into one of a set of domain-directed medical query classifications based on relevance to the local user medical information profile associated with the user-generated natural language medical information query.

Clause 28. A computer program product in a computer-readable medium for answering a user-generated natural language query, the computer program product in a computer-readable medium comprising program instructions which, when executed, cause a processor of a computer to perform:

receiving a user-generated natural language query at an artificial intelligence-based conversation agent from a user interface;

responsive to content of the user-generated natural language query, selecting a fact variable set relevant to generating a query answer for the user-generated natural language query by classifying the user-generated natural language query into one of a set of domain-directed query classifications associated with respective fact variable sets;

compiling user-specific fact variable values for one or more respective fact variables of the fact variable set; and responsive to the fact variable values, generating the query answer in response to the user-generated natural language query.

Clause 29. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:

extracting a first set of user-specific fact variable values from a local user profile associated with the user-generated natural language query; and requesting a second set of user-specific fact variable values through a conversational template comprising natural-language questions sent to the user interface on a mobile device.

Clause 30. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:

extracting a third set of user-specific fact variable values from a remote data service profile associated with the local user profile.

Clause 31. The computer program product in a computer-readable medium for answering a user-generated natural language query of any preceding clause, wherein the program instructions which, when executed, cause the processor of the computer to perform compiling user-specific fact variable values for one or more respective fact variables of the fact variable set further comprise program instructions which, when executed, cause the computer program product to perform:

extracting a fourth set of user-specific fact variable values derived from demographic characterizations provided by a remote data service analysis of the local user profile.

Clause 32. The computer program product in a computer-readable medium for answering a user-generated natural language query of any preceding clause, wherein program instructions which, when executed, cause the processor of the computer to perform the generating the query answer in response to the user-generated natural language query further comprise program instructions which, when executed, cause the processor of the computer to perform providing, in addition to text responsive to a question presented in the user-generated natural language query, an action-item recommendation responsive to the fact variable values and non-responsive to the question presented in the user-generated natural language query.

Clause 33. The computer program product in a computer-readable medium for answering a user-generated natural language query of any preceding clause, wherein the program instructions which, when executed, cause the processor of the computer to perform generating the query answer in response to the user-generated natural language query further comprise program instructions which, when executed, cause the processor of the computer to perform providing, in addition to text responsive to a question presented in the user-generated natural language query, an education media resource responsive to the fact variable values and non-responsive to the question presented in the user-generated natural language query.

Clause 34. The computer program product in a computer-readable medium for answering a user-generated natural language query of any preceding clause, wherein the program instructions which, when executed, cause the processor of the computer to perform selecting a fact variable set relevant to generating a query answer for the user-generated natural language query by classifying the user-generated natural language query into one of a set of domain-directed query classifications associated with respective fact variable sets further comprise program instructions which, when executed, cause the processor of the computer to perform classifying the user-generated natural language query into one of a set of domain-directed query classifications based on relevance to a local user profile associated with the user-generated natural language query.

Clause 35. A cognitive intelligence platform for answering a user-generated natural language query, the cognitive intelligence platform comprising:

a cognitive agent configured for receiving a user-generated natural language query at an artificial intelligence-based conversation agent from a user interface;

a critical thinking engine configured for, responsive to content of the user-generated natural language query, selecting a fact variable set relevant to generating a query answer for the user-generated natural language query by classifying the user-generated natural language query into one of a set of domain-directed query classifications associated with respective fact variable sets; and a knowledge cloud compiling user-specific fact variable values for one or more respective fact variables of the fact variable set; and wherein, responsive to the fact variable values, the cognitive agent is further configured for generating the query answer in response to the user-generated natural language query.

Clause 36. The cognitive intelligence platform of any preceding clause, wherein the knowledge cloud is further configured for:

extracting a first set of user-specific fact variable values from a local user profile associated with the user-generated natural language query; and requesting a second set of user-specific fact variable values through a conversational template comprising natural-language questions sent to the user interface on a mobile device.

Clause 37. The cognitive intelligence platform of any preceding clause, wherein the knowledge cloud is further configured for:

extracting a third set of user-specific fact variable values from a remote data service profile associated with the local user profile.

Clause 38. The cognitive intelligence platform of any preceding clause, wherein the knowledge cloud is further configured for:

extracting a fourth set of user-specific fact variable values derived from demographic characterizations provided by a remote data service analysis of the local user profile.

Clause 39. The cognitive intelligence platform of any preceding clause, wherein cognitive agent is further configured for providing, in addition to text responsive to a question presented in the user-generated natural language query, an action-item recommendation responsive to the fact variable values and non-responsive to the question presented in the user-generated natural language query.

Clause 40. The cognitive intelligence platform of any preceding clause, wherein the critical thinking engine is further configured for providing, in addition to text responsive to a question presented in the user-generated natural language query, an education media resource responsive to the fact variable values and non-responsive to the question presented in the user-generated natural language query.

Clause 41. A computer-implemented method for answering a user-generated natural language query, the method comprising:

receiving a user-generated natural language query at an artificial intelligence-based conversation agent from a user interface;

responsive to content of the user-generated natural language query, selecting a fact variable set relevant to generating a query answer for the user-generated natural language query by classifying the user-generated natural language query into one of a set of domain-directed query classifications associated with respective fact variable sets;

compiling user-specific fact variable values for one or more respective fact variables of the fact variable set; and responsive to the fact variable values, generating the query answer in response to the user-generated natural language query.

Clause 42. The method of any preceding clause, wherein the compiling user-specific fact variable values for one or more respective fact variables of the fact variable set further comprises:

extracting a first set of user-specific fact variable values from a local user profile associated with the user-generated natural language query; and requesting a second set of user-specific fact variable values through a conversational template comprising natural-language questions sent to the user interface on a mobile device.

Clause 43. The method of any preceding clause, wherein the compiling user-specific fact variable values for one or more respective fact variables of the fact variable set further comprises:

extracting a third set of user-specific fact variable values from a remote data service profile associated with the local user profile.

Clause 44. The method of any preceding clause, wherein the compiling user-specific fact variable values for one or more respective fact variables of the fact variable set further comprises:

extracting a fourth set of user-specific fact variable values derived from demographic characterizations provided by a remote data service analysis of the local user profile.

Clause 45. The method of any preceding clause, wherein the generating the query answer in response to the user-generated natural language query further comprises providing, in addition to text responsive to a question presented in the user-generated natural language query, an action-item recommendation responsive to the fact variable values and non-responsive to the question presented in the user-generated natural language query.

Clause 46. The method of any preceding clause, wherein the generating the query answer in response to the user-generated natural language query further comprises providing, in addition to text responsive to a question presented in the user-generated natural language query, an education media resource responsive to the fact variable values and non-responsive to the question presented in the user-generated natural language query.

Clause 47. The method of any preceding clause, wherein selecting a fact variable set relevant to generating a query answer for the user-generated natural language query by classifying the user-generated natural language query into one of a set of domain-directed query classifications associated with respective fact variable sets further comprises classifying the user-generated natural language query into one of a set of domain-directed query classifications based on relevance to a local user profile associated with the user-generated natural language query.

Clause 48. A computer-implemented method for answering natural language medical information questions posed by a user of a medical conversational interface of a cognitive artificial intelligence system, the method comprising:

receiving from a medical conversational user interface a user-generated natural language medical information query at an artificial intelligence-based medical conversation cognitive agent;

extracting from the user-generated natural language medical information query a medical question from a user of the medical conversational user interface;

compiling a medical conversation language sample, wherein the medical conversation language sample comprises items of health-information-related-text derived from a health-related conversation between the artificial intelligence-based medical conversation cognitive agent and the user;

extracting from the medical conversation language sample internal medical concepts and medical data entities present within the medical conversation language sample, wherein the internal medical concepts comprise descriptions of medical attributes of the medical data entities;

inferring a therapeutic intent of the user from the internal medical concepts and the medical data entities;

generating a therapeutic paradigm logical framework for interpreting of the medical question, wherein
the therapeutic paradigm logical framework comprises a catalog of medical logical progression paths from the medical question to respective therapeutic answers,
each of the medical logical progression paths comprises one or more medical logical linkages from the medical question to a therapeutic path-specific answer, and
the medical logical linkages comprise the internal medical concepts and external therapeutic paradigm concepts derived from a store of medical subject matter ontology data;

selecting a likely medical information path from among the medical logical progression paths to a likely path-dependent medical information answer based upon the therapeutic intent of the user; and answering the medical question by following the likely medical information path to the likely path-dependent medical information answer.

Clause 49. The computer-implemented method for answering natural language medical information questions posed by a user of a medical conversational interface of a cognitive artificial intelligence system of any of any of the preceding clauses, further comprising relating medical inference groups of the internal medical concepts.

Clause 50. The computer-implemented method for answering natural language medical information questions posed by a user of a medical conversational interface of a cognitive artificial intelligence system of any of any of the preceding clauses, wherein the relating medical inference groups of the internal medical concepts further comprises relating groups of the internal medical concepts based at least in part on shared medical data entities for which each internal medical concept of a medical inference group of internal medical concepts describes a respective medical data attribute.

Clause 51. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages.

Clause 52. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer after requesting additional medical diagnostic data from the user.

Clause 53. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon treatment sub-intents comprising tactical constituents related to the therapeutic intent of the user by the store of medical subject matter ontology data.

Clause 54. The computer-implemented method for answering natural language medical information questions posed by a user of a medical conversational interface of a cognitive artificial intelligence system of any of the preceding clauses, wherein selecting a likely medical information path from among the medical logical progression paths to a likely path-dependent medical information answer based upon the intent further comprises selecting a likely medical information path from among the medical logical progression paths to a likely path-dependent medical information answer based in part upon the therapeutic intent of the user and in part upon sufficiency of medical diagnostic data to complete the medical logical linkages, wherein the medical diagnostic data to complete the medical logical linkages includes user-specific medical diagnostic data.

Clause 55. A cognitive intelligence platform for answering natural language questions posed by a user of a conversational interface of an artificial intelligence system, the cognitive intelligence platform comprising:
 a cognitive agent configured for receiving from a user interface a user-generated natural language query, wherein the cognitive agent is an artificial intelligence-based conversation agent;
 a knowledge cloud containing a store of subject matter ontology data;
 a critical thinking engine configured for:
  extracting from the user-generated natural language query a question from a user of the user interface,
  compiling a language sample, wherein the language sample comprises items of text derived from a conversation between the artificial intelligence-based conversation agent and the user,
  extracting from the language sample internal concepts and entities present within the language sample, wherein the internal concepts comprise descriptions of attributes of the entities,
  inferring an intent of the user from the internal concepts and the entities,
  generating a logical framework for interpreting of the question, wherein
   the logical framework comprises a catalog of paths from the question to respective answers,
   each of the paths comprises one or more linkages from the question to a path-specific answer, and
   the linkages comprise the internal concepts and external concepts derived from the store of subject matter ontology data,
  selecting a likely path from among the paths to a likely path-dependent answer based upon the intent, and
  answering the question by following the likely path to the likely path-dependent answer.

Clause 56. The cognitive intelligence platform for answering natural language questions posed by a user of a conversational interface of an artificial intelligence system of any of the preceding clauses, wherein the critical thinking engine is further configured for relating groups of the internal concepts.

Clause 57. The cognitive intelligence platform for answering natural language questions posed by a user of a conversational interface of an artificial intelligence system of any of the preceding clauses, wherein the critical thinking engine is further configured for relating groups of the internal concepts by relating groups of the internal concepts based at least in part on shared entities for which each internal concept of a group of internal concepts describes a respective attribute.

Clause 58. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages.

Clause 59. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer after requesting additional data from the user.

Clause 60. The cognitive intelligence platform for answering natural language questions posed by a user of a conversational interface of an artificial intelligence system of 8, wherein the critical thinking engine is further configured for selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

Clause 61. The cognitive intelligence platform for answering natural language questions posed by a user of a conversational interface of an artificial intelligence system of any of the preceding clauses, wherein the critical thinking engine is further configured for selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

Clause 62. A computer program product in a computer-readable medium for answering natural language questions posed by a user of a conversational interface of an artificial intelligence system, the computer program product in a computer-readable medium comprising instructions, which, when executed, cause a processor of a computer to perform:
receiving from a user interface a user-generated natural language query at an artificial intelligence-based conversation agent;
extracting from the user-generated natural language query a question from a user of the user interface;
compiling a language sample, wherein the language sample comprises items of text derived from a conversation between the artificial intelligence-based conversation agent and the user;
extracting from the language sample internal concepts and entities present within the language sample, wherein the internal concepts comprise descriptions of attributes of the entities;
inferring an intent of the user from the internal concepts and the entities;
generating a logical framework for interpreting of the question, wherein
the logical framework comprises a catalog of paths from the question to respective answers,
each of the paths comprises one or more linkages from the question to a path-specific answer, and
the linkages comprise the internal concepts and external concepts derived from a store of subject matter ontology data;
selecting a likely path from among the paths to a likely path-dependent answer based upon the intent; and
answering the question by following the likely path to the likely path-dependent answer.

Clause 63. The computer program product in a computer-readable medium for answering natural language questions posed by a user of a conversational interface of an artificial intelligence system of any of the preceding clauses, further comprising instructions, which, when executed, cause the processor of the computer to perform relating groups of the internal concepts.

Clause 64. The computer program product in a computer-readable medium for answering natural language questions posed by a user of a conversational interface of an artificial intelligence system of any of the preceding clauses, wherein the instructions, which, when executed, cause the processor of the computer to perform relating groups of the internal concepts further comprise instructions, which, when executed, cause the processor of the computer to perform relating groups of the internal concepts based at least in part on shared entities for which each internal concept of a group of internal concepts describes a respective attribute.

Clause 65. The computer program product in a computer-readable medium for answering natural language questions posed by a user of a conversational interface of an artificial intelligence system of any of the preceding clauses, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon the intent and in part upon sufficiency of data to complete the linkages.

Clause 66. The computer program product in a computer-readable medium for answering natural language questions posed by a user of a conversational interface of an artificial intelligence system of any of the preceding clauses, wherein instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer after requesting additional data from the user.

Clause 67. The computer program product in a computer-readable medium for answering natural language questions posed by a user of a conversational interface of an artificial intelligence system of any of the preceding clauses, wherein the instructions, which, when executed, cause the processor of the computer to perform selecting a likely path from among the paths to a likely path-dependent answer based upon the intent further comprise instructions, which, when executed, cause the processor of the computer to perform selecting a likely path from among the paths to a likely path-dependent answer based in part upon sub-intents comprising tactical constituents related to the intent by the store of subject matter ontology data.

Clause 68. A method for answering natural language questions posed by a user of a conversational interface of an artificial intelligence system, the method comprising:
receiving from a user interface a user-generated natural language query at an artificial intelligence-based conversation agent;
extracting from the user-generated natural language query a question from a user of the user interface;
compiling a language sample, wherein the language sample comprises items of text derived from a conversation between the artificial intelligence-based conversation agent and the user;
extracting from the language sample internal concepts and entities present within the language sample, wherein the internal concepts comprise descriptions of attributes of the entities;
inferring an intent of the user from the internal concepts and the entities;
generating a logical framework for interpreting of the question, wherein
the logical framework comprises a catalog of paths from the question to respective answers,
each of the paths comprises one or more linkages from the question to a path-specific answer, and
the linkages comprise the internal concepts and external concepts derived from a store of subject matter ontology data;
selecting a likely path from among the paths to a likely path-dependent answer based upon the intent; and
answering the question by following the likely path to the likely path-dependent answer.

Clause 69. The method for answering natural language questions posed by a user of a conversational interface of an artificial intelligence system of any of the preceding clauses, further comprising relating groups of the internal concepts.

Clause 70. The method for answering natural language questions posed by a user of a conversational interface of an artificial intelligence system of any of the preceding clauses, wherein the relating groups of the internal concepts further comprises relating groups of the internal concepts based at least in part on shared entities for which each internal concept of a group of internal concepts describes a respective attribute.

Clause 71. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon the intent and in part upon sufficiency of data to complete the linkages.

Clause 72. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer after requesting additional data from the user.

Clause 73. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon sub-intents comprising tactical constituents related to the intent by the store of subject matter ontology data.

Clause 74. The method for answering natural language questions posed by a user of a conversational interface of an artificial intelligence system of any of the preceding clauses, wherein selecting a likely path from among the paths to a likely path-dependent answer based upon the intent further comprises selecting a likely path from among the paths to a likely path-dependent answer based in part upon the intent and in part upon sufficiency of data to complete the linkages, wherein the data to complete the linkages includes user-specific data.

Clause 75. A computer-implemented method for providing therapeutic medical action recommendations in response to a medical information natural language conversation stream, the computer-implemented method comprising:
  receiving segments of a medical information natural language conversation stream at an artificial intelligence-based health information conversation agent from a medical information conversation user interface;
  responsive to medical information content of a user medical information profile associated with the medical information natural language conversation stream, defining a desired clinical management outcome objective relevant to health management criteria and related health management data attributes of the user medical information profile;
  identifying a set of potential therapeutic interventions correlated to advancement of the clinical management outcome objective;
  selecting from among the set of potential therapeutic interventions correlated to advancement of the clinical management outcome objective a medical intervention likely to advance the clinical management outcome objective;
  presenting in the medical information natural language conversation stream a therapeutic advice conversation stream segment designed to stimulate execution of the medical intervention likely to advance the clinical management outcome objective; and
  presenting to the user in the medical information natural language conversation stream a therapeutic advice conversation stream segment explaining a correlation between the medical intervention likely to advance the clinical management outcome objective and achievement of the clinical management outcome objective.

Clause 76. The computer-implemented method for providing therapeutic medical action recommendations in response to a medical information natural language conversation stream of any preceding clause, wherein the selecting from among the set of potential therapeutic interventions correlated to advancement of the clinical management outcome objective a medical intervention likely to advance the clinical management outcome objective further comprises:
  selecting from among the set of potential therapeutic interventions correlated to advancement of the clinical management outcome objective the medical intervention likely to advance the clinical management outcome objective based on a set of factors comprising likelihood of patient compliance with the a recommendation for the a medical intervention likely to advance the clinical management outcome objective and a statistical likelihood that the action will materially advance the clinical management outcome objective.

Clause 77. The computer-implemented method for providing therapeutic medical action recommendations in response to a medical information natural language conversation stream any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining a cost-benefit analysis comparing likely results of performance of the action likely to advance the clinical management outcome objective and likely results of non-performance of the action likely to advance the clinical management outcome objective.

Clause 78. The computer-implemented method for providing therapeutic medical action recommendations in response to a medical information natural language conversation stream of any preceding clause, wherein the selecting from among the set of potential therapeutic interventions correlated to advancement of the clinical management outcome objective a medical intervention likely to advance the clinical management outcome objective further comprises:
  selecting from among the set of potential therapeutic interventions correlated to advancement of the clinical management outcome objective the medical intervention likely to advance the clinical management outcome objective based on a set of factors comprising likelihood total expected cost expectation associated with the recommendation for the a medical intervention likely to advance the clinical management outcome objective.

Clause 79. The computer-implemented method for providing therapeutic medical action recommendations in response to a medical information natural language conversation stream of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a conversation stream reinforcing the recommendation after expiration of a delay period.

Clause 80. The computer-implemented method for providing therapeutic medical action recommendations in response to a medical information natural language conversation stream of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining reasons for selection of the clinical management outcome objective.

Clause 81. The computer-implemented method for providing therapeutic medical action recommendations in response to a medical information natural language conversation stream of any preceding clause, wherein the presenting to the user in the medical information natural language conversation stream a therapeutic advice conversation stream segment designed to stimulate execution of the action likely to advance the clinical management outcome objective further comprises notifying third party service providers of the clinical management outcome objective and the recommendation.

Clause 82. A computer program product in a non-transitory computer-readable medium for providing therapeutic medical action recommendations in response to a medical information natural language conversation stream, the computer program product in a non-transitory computer-readable medium comprising instructions which, when executed cause a processor of a computer to perform:
  receiving segments of a medical information natural language conversation stream at an artificial intelligence-based health information conversation agent from a medical information conversation user interface;
  responsive to medical information content of a user medical information profile associated with the medical information natural language conversation stream, defining a clinical management outcome objective relevant to health management criteria and related health management data attributes of the profile;
  selecting a medical intervention likely to advance the clinical management outcome objective; and
  presenting to the user in the medical information natural language conversation stream a therapeutic advice conversation stream segment designed to stimulate execution of the action likely to advance the clinical management outcome objective.

83. The computer program product in a non-transitory computer-readable medium of any preceding clause, wherein the instructions which, when executed cause the processor of the computer to perform selecting a medical intervention likely to advance the clinical management outcome objective further comprise instructions which, when executed cause the processor of the computer to perform:
  identifying a set of potential therapeutic interventions correlated to advancement of the clinical management outcome objective; and
  selecting the action likely to advance the user outcome objective based on a set of factors comprising likelihood of performance of the action likely to advance the user outcome objective and likelihood that the action will materially advance the user outcome objective.

Clause 84. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a therapeutic advice conversation stream segment explaining a correlation between the action likely to advance the clinical management outcome objective and achievement of the clinical management outcome objective.

Clause 85. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a therapeutic advice conversation stream segment explaining a plan of subsequent actions likely to advance the clinical management outcome objective.

Clause 86. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a conversation stream reinforcing the recommendation after expiration of a delay period.

Clause 87. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform presenting to the user in the medical information natural language conversation stream a therapeutic advice conversation stream segment explaining reasons for selection of the clinical management outcome objective.

Clause 88. The computer program product in a non-transitory computer-readable medium of any preceding clause, wherein the instructions which, when executed cause the processor of the computer to perform presenting to the user in the medical information natural language conversation stream a therapeutic advice conversation stream segment designed to stimulate execution of the action likely to advance the clinical management outcome objective further comprise instructions which, when executed cause the processor of the computer to perform notifying third party service providers of the clinical management outcome objective and the recommendation.

Clause 89. A system for providing therapeutic medical action recommendations in response to a medical information natural language conversation stream, the system comprising:

a knowledge cloud configured for receiving segments of a medical information natural language conversation stream at an artificial intelligence-based health information from a medical information conversation user interface of a cognitive agent;

a critical thinking engine configured for:
responsive to medical information content of a user medical information profile associated with the medical information natural language conversation stream in the knowledge cloud, defining a clinical management outcome objective relevant to health management criteria and related health management data attributes of the profile, and
selecting a medical intervention likely to advance the clinical management outcome objective; and the cognitive agent, wherein the cognitive agent is configure for presenting to the user in the medical information natural language conversation stream a therapeutic advice conversation stream segment designed to stimulate execution of the action likely to advance the clinical management outcome objective.

Clause 90. The system of any preceding clause, wherein the selecting a medical intervention likely to advance the clinical management outcome objective further comprises:
identifying a set of potential therapeutic interventions correlated to advancement of the clinical management outcome objective; and
selecting the action likely to advance the user outcome objective based on a set of factors comprising likelihood of performance of the action likely to advance the user outcome objective and likelihood that the action will materially advance the user outcome objective.

Clause 91. The system of claim any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining a correlation between the action likely to advance the clinical management outcome objective and achievement of the clinical management outcome objective.

Clause 92. The system of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a therapeutic advice conversation stream segment explaining a plan of subsequent actions likely to advance the clinical management outcome objective.

Clause 93. The system of any preceding clause, wherein the presenting to the user in the medical information natural language conversation stream a therapeutic advice conversation stream segment designed to stimulate execution of the action likely to advance the clinical management outcome objective further comprises presenting to the user in the medical information natural language conversation stream a conversation stream reinforcing the recommendation after expiration of a delay period.

Clause 94. The system of any preceding clause, wherein the presenting to the user in the medical information natural language conversation stream a conversation stream segment designed to stimulate execution of the action likely to advance the clinical management outcome objective further comprises presenting to the user in the medical information natural language conversation stream a conversation stream segment explaining reasons for selection of the clinical management outcome objective.

Clause 95. A computer-implemented method for providing action recommendations in response to a user-generated natural language conversation stream, the method comprising:
receiving segments of a user-generated natural language conversation stream at an artificial intelligence-based conversation agent from a user interface;
responsive to content of a user profile associated with the user-generated natural language conversation stream, defining a user action outcome objective relevant to attributes of the profile;
selecting an action likely to advance the user action outcome objective; and
presenting to the user in the user-generated natural language conversation stream a conversation stream segment designed to motivate performance of the action likely to advance the user action outcome objective.

Clause 96. The method of any preceding clause, wherein the selecting an action likely to advance the user action outcome objective further comprises:
identifying a set of actions correlated to advancement of the user action outcome objective; and
selecting the action likely to advance the user outcome objective based on a set of factors comprising likelihood of performance of the action likely to advance the user outcome objective and likelihood that the action will materially advance the user outcome objective.

Clause 97. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream segment explaining a correlation between the action likely to advance the user action outcome objective and achievement of the user action outcome objective.

Clause 98. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream segment explaining a plan of subsequent actions likely to advance the user action outcome objective.

Clause 99. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream reinforcing the recommendation after expiration of a delay period.

Clause 100. The method of any preceding clause, wherein the presenting to the user in the user-generated natural language conversation stream a conversation stream segment designed to motivate performance of the action likely to advance the user action outcome objective further comprises presenting to the user in the user-generated natural language conversation stream a conversation stream segment explaining reasons for selection of the user action outcome objective.

Clause 101. The method of any preceding clause, wherein the presenting to the user in the user-generated natural language conversation stream a conversation stream segment designed to motivate performance of the action likely to advance the user action outcome objective further comprises notifying third party service providers of the user action outcome objective and the recommendation.

Clause 102. A method comprising:
receiving, at an artificial intelligence engine, a corpus of data for a patient, wherein the corpus of data includes a plurality of strings of characters;
identifying, in the plurality of strings of characters, indicia comprising a phrase, a predicate, a keyword, a subject, an object, a cardinal, a number, a concept, or some combination thereof;
comparing the indicia to a knowledge graph representing known health related information to generate a possible health related information pertaining to the patient;
identifying, using a logical structure, a structural similarity of the possible health related information and a known predicate in the logical structure; and
generating, by the artificial intelligence engine, cognified data based on the structural similarity.

Clause 103. The method of any preceding clause, further comprising generating the knowledge graph using the known health related information, wherein the knowledge graph represents knowledge of a disease and the knowledge graph comprises a plurality of concepts pertaining to the disease obtained from the known health related information, and the knowledge graph comprises relationships between the plurality of concepts.

Clause 104. The method of any preceding clause, wherein the cognified data comprises a health related summary of the possible health related information.

Clause 105. The method of any preceding clause, wherein generating, by the artificial intelligence engine, the cognified data further comprises:
generating at least one new string of characters representing a statement pertaining to the possible health related information; and
including the at least one new string of characters in the health related summary of the possible health related information.

Clause 106. The method of any preceding clause, wherein the statement describes an effect that results from the possible health related information.

Clause 107. The method of any preceding clause, further comprising codifying evidence based health related guidelines pertaining to a disease to generate the logical structure.

Clause 108. The method of any preceding clause, further comprising:
identifying at least one piece of information missing in the corpus of data for the patient using the cognified data, wherein the at least one piece of information pertains to a treatment gap, a risk gap, a quality of care gap, or some combination thereof; and
causing a notification to be presented on a computing device of a healthcare personnel, wherein the notification instructs entry of the at least one piece of information.

Clause 109. The method of any preceding clause, wherein using the logical structure to identify the structural similarity of the indicia and the known predicate in the logical structure further comprises identifying, based on the structural similarity of the indicia and the known predicate in the logical structure, a treatment pattern, a referral pattern, a quality of care pattern, a risk adjustment pattern, or some combination thereof in the corpus of data.

Clause 110. The method of any preceding clause, further comprising:
receiving feedback pertaining to whether the cognified data is accurate; and
updating the artificial intelligence engine based on the feedback.

Clause 111. The method of any preceding clause, a tangible, non-transitory computer-readable medium storing instructions that, when executed, cause a processing device to execute an artificial intelligence engine to:
receive a corpus of data for a patient, wherein the corpus of data includes a plurality of strings of characters;
identify, in the plurality of strings of characters, indicia comprising a phrase, a predicate, a keyword, a cardinal, a number, a concept, or some combination thereof;
compare the indicia to a knowledge graph representing known health related information to generate a possible health related information pertaining to the patient;
identify, using a logical structure, a structural similarity of the indicia and a known predicate in the logical structure; and
generate cognified data based on the similarity and the possible health related information.

Clause 112. The computer-readable medium of any preceding clause, wherein the artificial intelligence engine is further to generate the knowledge graph using the known health related information, wherein the knowledge graph represents knowledge of a disease and the knowledge graph comprises a plurality of concepts pertaining to the disease obtained from the known health related information, and the knowledge graph comprises relationships between the plurality of concepts.

Clause 113. The computer-readable medium of any preceding clause, wherein the cognified data comprises a health related summary of the possible health related information.

Clause 114. The computer-readable medium of any preceding clause, wherein generating, based on the pattern, the cognified data further comprises:
generating at least one new string of characters representing a statement pertaining to the possible health related information; and
including the at least one new string of characters in the health related summary of the possible health related information.

Clause 115. The computer-readable medium of any preceding clause, wherein the statement describes an effect that results from the possible health related information Clause 116. The computer-readable medium of any preceding clause, wherein the artificial intelligence engine is further to codify evidence based health related guidelines pertaining to a disease to generate the logical structure.

Clause 117. The computer-readable medium of any preceding clause, wherein the artificial intelligence engine is further to:
identify at least one piece of information missing in the corpus of data for the patient using the cognified data, wherein the at least one piece of information pertains to a treatment gap, a risk gap, a quality of care gap, or some combination thereof; and
cause a notification to be presented on a computing device of a healthcare personnel, wherein the notification instructs entry of the at least one piece of information.

Clause 118. The computer-readable medium of any preceding clause, wherein using the logical structure to identify the structural similarity of the indicia and the known predicate in the logical structure further comprises identifying, based on the structural similarity of the indicia and the known predicate in the logical structure, a treatment pattern, a referral pattern, a quality of care pattern, a risk adjustment pattern, or some combination thereof in the corpus of data.

Clause 119. The computer-readable medium of any preceding clause, wherein the artificial intelligence engine is further to:
  receive feedback pertaining to whether the cognified data is accurate; and
  update the artificial intelligence engine based on the feedback.

Clause 120. a system, comprising:
  a memory device storing instructions; and
  a processing device operatively coupled to the memory device, wherein the processing device executes the instructions to:
  receive, at an artificial intelligence engine, a corpus of data for a patient, wherein the corpus of data includes a plurality of strings of characters;
  identify, in the plurality of strings of characters, indicia comprising a phrase, a predicate, a keyword, a cardinal, a number, a concept, or some combination thereof;
  compare the indicia to a knowledge graph representing known health related information to generate a possible health related information pertaining to the patient;
  identify, using a logical structure, a structural similarity of the indicia and a known predicate in the logical structure; and
  generate, by the artificial intelligence engine, cognified data based on the similarity and the possible health related information.

Clause 121. The system of any preceding claim, wherein the processing device is further to:
  receive feedback pertaining to whether the cognified data is accurate; and
  update the artificial intelligence engine based on the feedback.

Clause 122. A method for controlling distribution of a plurality of information pertaining to a medical condition, the method comprising:
  receiving, at a server, an electronic medical record comprising notes pertaining to a patient;
  processing the notes to obtain indicia comprising a word, a cardinal, a phrase, a sentence, a predicate, or some combination thereof;
  identifying a possible medical condition of the patient by identifying a similarity between the indicia and a knowledge graph representing knowledge pertaining to the possible medical condition, wherein the knowledge graph comprises a plurality of nodes representing the plurality of information pertaining to the possible medical condition; and
  providing, at a first time, first information of the plurality of information to a computing device of the patient for presentation on the computing device, the first information being associated with a root node of the plurality of nodes.

Clause 123. The method of any preceding claim, further comprising providing, at a second time, second information of the plurality of information to the computing device of the patient for presentation on the computing device, the second information being associated with a second node of the plurality of nodes, and the second time being after the first time.

Clause 124. The method of any preceding claim, wherein the second information pertains to how the possible medical condition affects people, signs and symptoms of the possible medical condition, a way to treat the possible medical condition, a progression of the possible medical condition, or some combination thereof.

Clause 125. The method of any preceding claim, wherein the second time is selected based on when the second information is relevant to a stage of the possible medical condition.

Clause 126. The method of any preceding claim, further comprising providing, at a third time, third information of the plurality of information to the computing device of the patient for presentation on the computing device, the third information being associated with a third node of the plurality of nodes, and the third time being after the second time.

Clause 127. The method of any preceding claim, wherein identifying the possible medical condition by identifying the similarity between the indicia and the knowledge graph further comprises using an artificial intelligence engine that is trained using feedback from medical personnel, wherein the feedback pertains to whether output regarding possible medical conditions from the artificial intelligence engine is accurate for input comprising notes of patients.

Clause 128. The method of any preceding claim, wherein the first information pertains to a name of the possible medical condition, a definition of the possible medical condition, or some combination thereof.

Clause 129. The method of any preceding claim, wherein identifying the possible medical condition by identifying the similarity between the indicia and the knowledge graph further comprises using a cognified data structure generated from the notes of the patient, wherein the cognified data structure includes a conclusion based on a logical structure representing codified evidence based guidelines pertaining to the possible medical condition.

Clause 130. The method of any preceding claim, wherein processing the patient notes to obtain the indicia further comprises inputting the notes into an artificial intelligence engine trained to identify the indicia in text based on commonly used indicia pertaining to the possible medical condition.

Clause 131. The method of any preceding claim, further comprising:
  identifying a second possible medical condition of the patient by identifying a second similarity between the indicia and a second knowledge graph representing second knowledge pertaining to the second possible medical condition, wherein the second knowledge graph comprises a second plurality of nodes representing a second plurality of information pertaining to the second possible medical condition; and
  providing, at the first time, second information of the second plurality of information to the computing device of the patient for presentation on the computing device, the second information being associated with a second root node of the second plurality of nodes.

Clause 132. A tangible, non-transitory computer-readable medium storing instructions that, when executed, cause a processing device to:
  receive an electronic medical record comprising notes pertaining to a patient;

process the notes to obtain indicia comprising a word, a cardinal, a phrase, a sentence, a predicate, or some combination thereof;

identify a possible medical condition of the patient by identifying a similarity between the indicia and a knowledge graph representing knowledge pertaining to the possible medical condition, wherein the knowledge graph comprises a plurality of nodes representing the plurality of information pertaining to the possible medical condition; and provide, at a first time, first information of the plurality of information to a computing device of the patient for presentation on the computing device, the first information being associated with a root node of the plurality of nodes.

Clause 133. The computer-readable medium of any preceding clause, wherein the processing device is further to provide, at a second time, second information of the plurality of information to the computing device of the patient for presentation on the computing device, the second information being associated with a second node of the plurality of nodes, and the second time being after the first time.

Clause 134. The computer-readable medium of any preceding clause, wherein the second information pertains to how the possible medical condition affects people, signs and symptoms of the possible medical condition, a way to treat the possible medical condition, a progression of the possible medical condition, or some combination thereof.

Clause 135. The computer-readable medium of any preceding clause, wherein the second time is selected based on when the second information is relevant to a stage of the possible medical condition.

Clause 136. The computer-readable medium of any preceding clause, further comprising providing, at a third time, third information of the plurality of information to the computing device of the patient for presentation on the computing device, the third information being associated with a third node of the plurality of nodes, and the third time being after the second time.

Clause 137. The computer-readable medium of any preceding clause, wherein detecting the possible medical condition by identifying the similarity between the indicia and the knowledge graph further comprises using an artificial intelligence engine that is trained using feedback from medical personnel, wherein the feedback pertains to whether output regarding possible medical conditions from the artificial intelligence engine is accurate.

Clause 138. The computer-readable medium of any preceding clause, wherein the first information pertains to a name of the possible medical condition, a definition of the possible medical condition, or some combination thereof.

Clause 139. The computer-readable medium of any preceding clause, wherein detecting the possible medical condition by identifying the similarity between the indicia and the knowledge graph further comprises using a cognified data structure generated from the notes of the patient, wherein the cognified data structure includes a conclusion about the predicate that is identified in a logic structure representing codified evidence based guidelines pertaining to the possible medical condition.

Clause 140. The computer-readable medium of any preceding clause, wherein processing the patient notes to obtain the indicia further comprises inputting the notes into an artificial intelligence engine trained to identify the indicia in text based on commonly used indicia pertaining to the possible medical condition.

Clause 141. a system, comprising:
a memory device storing instructions;
a processing device communicatively coupled to the memory device, the processing device executes the instructions to:
receive, at a server, an electronic medical record comprising notes pertaining to a patient;
process the notes to obtain indicia comprising a word, a cardinal, a phrase, a sentence, a predicate, or some combination thereof;
identify a possible medical condition of the patient by identifying a similarity between the indicia and a knowledge graph representing knowledge pertaining to the possible medical condition, wherein the knowledge graph comprises a plurality of nodes representing the plurality of information pertaining to the possible medical condition; and
provide, at a first time, first information of the plurality of information to a computing device of the patient for presentation on the computing device, the first information being associated with a root node of the plurality of nodes.

Clause 142. A method for diagnosing a medical condition through cognification of unstructured data, the method comprising:
receiving, at a server, an electronic medical record comprising notes pertaining to a patient;
generating cognified data using the notes, wherein the cognified data comprises a health summary of the medical condition;
generating, based on the cognified data, a diagnosis of the medical condition of the patient, wherein the diagnosis at least identifies a type of the medical condition; and
providing the diagnosis to a computing device for presentation on the computing device.

Clause 143. The method of any preceding clause, further comprising identifying, in the notes, indicia comprising a phrase, a predicate, a keyword, a cardinal, a number, a concept, or some combination thereof;

Clause 144. The method of any preceding clause, wherein generating the cognified data further comprises detecting the medical condition by identifying a similarity between the indicia and a knowledge graph.

Clause 145. The method of any preceding clause, further comprising using an artificial intelligence engine that is trained using feedback from medical personnel, wherein the feedback pertains to whether output regarding diagnoses from the artificial intelligence engine are accurate for input comprising notes of patients.

Clause 146. The method of any preceding clause, wherein the cognified data includes a conclusion that is identified based on a logic structure representing codified evidence based guidelines pertaining to the medical condition.

Clause 147. The method of any preceding clause, further comprising processing the notes to obtain indicia by inputting the notes into an artificial intelligence engine trained to identify the indicia in text based on commonly used indicia pertaining to the medical condition.

Clause 148. The method of any preceding clause, wherein generating the diagnosis further comprises:
determining a stage of the medical condition based on the cognified data; and
including the stage of the medical condition in the diagnosis.

Clause 149. The method of any preceding clause, further comprising:
determining a severity of the medical condition based on the stage and the type of the medical condition;

in response to the severity satisfying a threshold condition, providing a recommendation to seek immediate medical attention to a computing device of the patient.

Clause 150. A tangible, non-transitory computer-readable medium storing instructions that, when executed, cause a processing device to:
receive, at a server, an electronic medical record comprising notes pertaining to a patient;
generate cognified data using the notes, wherein the cognified data comprises a health summary of the medical condition;
generate, based on the cognified data, a diagnosis of the medical condition of the patient, wherein the diagnosis at least identifies a type of the medical condition; and
provide the diagnosis to a computing device for presentation on the computing device.

Clause 151. The computer-readable medium of any preceding clause, wherein the processing device is further to identify, in the notes, indicia comprising a phrase, a predicate, a keyword, a cardinal, a number, a concept, or some combination thereof;

Clause 152. The computer-readable medium of any preceding clause, wherein generating the cognified data further comprises detecting the medical condition by identifying a similarity between the indicia and a knowledge graph.

Clause 153. The computer-readable medium of any preceding clause, wherein the processing device is further to use an artificial intelligence engine that is trained using feedback from medical personnel, wherein the feedback pertains to whether output regarding diagnoses from the artificial intelligence engine are accurate for input comprising notes of patients.

Clause 154. The computer-readable medium of any preceding clause, wherein the cognified data includes a conclusion about a predicate in the notes that is identified in a logic structure representing codified evidence based guidelines pertaining to the medical condition.

Clause 155. The computer-readable medium of any preceding clause, wherein the processing device is further to process the patient notes to obtain indicia by inputting the notes into an artificial intelligence engine trained to identify the indicia in text based on commonly used indicia pertaining to the medical condition.

Clause 156. The computer-readable medium of any preceding clause, wherein generating the diagnosis further comprises:
determining a stage of the medical condition based on the cognified data; and
including the stage of the medical condition in the diagnosis.

Clause 157. The computer-readable medium of any preceding clause, wherein the processing device is further to:
determine a severity of the medical condition based on the stage and the type of the medical condition;
in response to the severity satisfying a threshold condition, provide a recommendation to seek immediate medical attention to a computing device of the patient.

Clause 158. A system, comprising:
a memory device storing instructions; and
a processing device communicatively coupled to the memory device, the processing device executes the instructions to:
receive, at a server, an electronic medical record comprising notes pertaining to a patient;
generate cognified data using the notes, wherein the cognified data comprises a health summary of the medical condition;
generate, based on the cognified data, a diagnosis of the medical condition of the patient, wherein the diagnosis at least identifies a type of the medical condition; and
provide the diagnosis to a computing device for presentation on the computing device.

Clause 159. The system of any preceding clause, wherein the processing device is further to identify, in the notes, indicia comprising a phrase, a predicate, a keyword, a cardinal, a number, a concept, or some combination thereof;

Clause 160. The system of any preceding clause, wherein generating the cognified data further comprises detecting the medical condition by identifying a similarity between the indicia and a knowledge graph.

Clause 161. The system of any preceding clause, wherein the processing device is further to use an artificial intelligence engine that is trained using feedback from medical personnel, wherein the feedback pertains to whether output regarding diagnoses from the artificial intelligence engine are accurate for input comprising notes of patients.

The foregoing description, for purposes of explanation, used specific nomenclature to provide a thorough understanding of the described embodiments. However, it should be apparent to one skilled in the art that the specific details are not required in order to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A method for diagnosing a medical condition through cognification of unstructured data, the method comprising:
receiving, at a server, an electronic medical record comprising notes pertaining to a patient;
processing the notes to obtain indicia by inputting the notes into an artificial intelligence engine trained to identify the indicia in text based on commonly used indicia pertaining to the medical condition;
generating, based on the indicia using the artificial intelligence engine and a knowledge graph, cognified data using the notes, wherein the cognified data comprises a health summary of the medical condition;
generating, based on the cognified data, a diagnosis of the medical condition of the patient, wherein the diagnosis at least identifies a type of the medical condition; and
providing the diagnosis to a computing device for presentation on the computing device.

2. The method of claim 1, further comprising identifying, in the notes, indicia comprising a phrase, a predicate, a keyword, a cardinal, a number, a concept, or some combination thereof.

3. The method of claim 2, wherein generating the cognified data further comprises detecting the medical condition by identifying a similarity between the indicia and the knowledge graph.

4. The method of claim 3, further comprising using an artificial intelligence engine that is trained using feedback from medical personnel, wherein the feedback pertains to whether output regarding diagnoses from the artificial intelligence engine are accurate for input comprising notes of patients.

5. The method of claim 1, wherein the cognified data includes a conclusion that is identified based on a logic structure representing codified evidence based guidelines pertaining to the medical condition.

6. The method of claim 1, wherein generating the diagnosis further comprises:
   determining a stage of the medical condition based on the cognified data; and
   including the stage of the medical condition in the diagnosis.

7. The method of claim 6, further comprising:
   determining a severity of the medical condition based on the stage and the type of the medical condition;
   in response to the severity satisfying a threshold condition, providing a recommendation to seek immediate medical attention to a computing device of the patient.

8. A tangible, non-transitory computer-readable medium storing instructions that, when executed, cause a processing device to:
   receive, at a server, an electronic medical record comprising notes pertaining to a patient;
   processing the notes to obtain indicia by inputting the notes into an artificial intelligence engine trained to identify the indicia in text based on commonly used indicia pertaining to the medical condition;
   generate, based on the indicia using the artificial intelligence engine and a knowledge graph, cognified data using the notes, wherein the cognified data comprises a health summary of the medical condition;
   generate, based on the cognified data, a diagnosis of the medical condition of the patient, wherein the diagnosis at least identifies a type of the medical condition; and
   provide the diagnosis to a computing device for presentation on the computing device.

9. The computer-readable medium of claim 8, wherein the processing device is further to identify, in the notes, indicia comprising a phrase, a predicate, a keyword, a cardinal, a number, a concept, or some combination thereof.

10. The computer-readable medium of claim 9, wherein generating the cognified data further comprises detecting the medical condition by identifying a similarity between the indicia and the knowledge graph.

11. The computer-readable medium of claim 10, wherein the processing device is further to use an artificial intelligence engine that is trained using feedback from medical personnel, wherein the feedback pertains to whether output regarding diagnoses from the artificial intelligence engine are accurate for input comprising notes of patients.

12. The computer-readable medium of claim 8, wherein the cognified data includes a conclusion about a predicate in the notes that is identified in a logic structure representing codified evidence based guidelines pertaining to the medical condition.

13. The computer-readable medium of claim 8, wherein generating the diagnosis further comprises:
   determining a stage of the medical condition based on the cognified data; and
   including the stage of the medical condition in the diagnosis.

14. The computer-readable medium of claim 13, wherein the processing device is further to:
   determine a severity of the medical condition based on the stage and the type of the medical condition;
   in response to the severity satisfying a threshold condition, provide a recommendation to seek immediate medical attention to a computing device of the patient.

15. A system, comprising:
   a memory device storing instructions; and
   a processing device communicatively coupled to the memory device, the processing device executes the instructions to:
      receive, at a server, an electronic medical record comprising notes pertaining to a patient;
      processing the notes to obtain indicia by inputting the notes into an artificial intelligence engine trained to identify the indicia in text based on commonly used indicia pertaining to the medical condition;
      generate, based on the indicia using the artificial intelligence engine and a knowledge graph, cognified data using the notes, wherein the cognified data comprises a health summary of the medical condition;
      generate, based on the cognified data, a diagnosis of the medical condition of the patient, wherein the diagnosis at least identifies a type of the medical condition; and
      provide the diagnosis to a computing device for presentation on the computing device.

16. The system of claim 15, wherein the processing device is further to identify, in the notes, indicia comprising a phrase, a predicate, a keyword, a cardinal, a number, a concept, or some combination thereof.

17. The system of claim 16, wherein generating the cognified data further comprises detecting the medical condition by identifying a similarity between the indicia and the knowledge graph.

18. The system of claim 17, wherein the processing device is further to use an artificial intelligence engine that is trained using feedback from medical personnel, wherein the feedback pertains to whether output regarding diagnoses from the artificial intelligence engine are accurate for input comprising notes of patients.

* * * * *